(12) United States Patent
Kaloun et al.

(10) Patent No.: US 10,323,043 B2
(45) Date of Patent: Jun. 18, 2019

(54) DERIVATIVES OF MACROCYCLIC N-ARYL-TRICYCLOPYRIMIDINE-2-AMINE POLYETHERS AS INHIBITORS OF FTL3 AND JAK

(71) Applicant: PIERRE FABRE MEDICAMENT, Boulogne-Billancourt (FR)

(72) Inventors: El Bachir Kaloun, Roquettes (FR); Serge Grisoni, Portet sur Garonne (FR); Anna Kruczynski, Pompertuzat (FR); Philippe Schmitt, Nailloux (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 15/508,014

(22) PCT Filed: Sep. 2, 2015

(86) PCT No.: PCT/EP2015/070072
§ 371 (c)(1),
(2) Date: Mar. 1, 2017

(87) PCT Pub. No.: WO2016/034637
PCT Pub. Date: Mar. 10, 2016

(65) Prior Publication Data
US 2017/0283432 A1 Oct. 5, 2017

(30) Foreign Application Priority Data
Sep. 2, 2014 (FR) ..................... 14 58204

(51) Int. Cl.
*C07D 498/08* (2006.01)
*C07D 519/00* (2006.01)
(52) U.S. Cl.
CPC ......... *C07D 498/08* (2013.01); *C07D 519/00* (2013.01)
(58) Field of Classification Search
CPC ............................ C07D 498/08; C07D 519/00
See application file for complete search history.

(56) References Cited

FOREIGN PATENT DOCUMENTS
WO  WO 2007/058627 A1  5/2007

OTHER PUBLICATIONS
STN Registry record of 1883671-86-0 (Year: 2016).*
French Preliminary Search Report, dated Jan. 22, 2015, for French Application No. 1458204.

Gilliland et al., "The Roles of FLT3 in Hematopoiesis and Leukemia," Blood, vol. 100. No. 5, Sep. 1, 2002 (Prepublished online as Blood First Edition Paper, May 24, 2002), pp. 1532-1542 (Total 12 pages).
Harris et al., "Improved Functional Group Compatibility in the Palladium-Catalyzed Synthesis of Aryl Amines," Organic Letters, vol. 4, No. 17, 2002 (Published on Web Jul. 30, 2002), pp. 2885-2888.
Imanishi et al., "Discovery of a Novel Series of Benzoic Acid Derivatives as Potent and Selective Human $\beta_3$-Adrenergic Receptor Agonists with Good Oral Bioavailability. 3. Phenylethanolaminotetraline (PEAT) . . . ," J. Med. Chem., vol. 51, No. 15, 2008 (Published on Web Jul. 24, 2008), pp. 4804-4822.
Kayser et al., "FLT3 Tyrosine Kinase Inhibitors in Acute Myeloid Leukemia: Clinical Implications and Limitations," Leuk Lymphoma., vol. 55, No. 2, Feb. 2014, pp. 243-255 (Total 24 pages).
Niu et al., "Copper(I)-Catalyzed Aryl Bromides to Form Intermolecular and Intramolecular Carbon-Oxygen Bonds," J. Org. Chem., vol. 74, No. 14, 2009 (Published on Web May 28, 2009), pp. 5075-5078.
Poulsen et al., "Structure-based Design of Oxygen-linked Macrocyclic Kinase Inhibitors: Discovery of SB1518 and SB1578, Potent Inhibitors of Janus Kinase 2 (JAK2) and Fms-like Tyrosine . . . ," J Comput Aided Mol Des, vol. 26, No. 4, 2012 (Published online Apr. 22, 2012), pp. 437-450, XP-35053361A.
Rodriguez et al., "Guanidine and 2-Aminoimidazoline Aromatic Derivatives as $\alpha_2$-Adrenoceptor Antagonists, 1: Toward New Antidepressants with Heteroatomic Linkers," J. Med. Chem., vol. 50, No. 18, 2007 (Published on Web Aug. 10, 2007), pp. 4516-4527.
Sonogashira et al., "A Convenient Synthesis of Acetylenes: Catalytic Substitutions of Acetylenic Hydrogen with Bromoalkenes, Iodoarenes, and Bromopyridines," Tetrahedron Letters, No. 50, 1975, pp. 4467-4470.
Weisberg et al., "Using Combination Therapy to Override Stromal-mediated Chemoresistance in Mutant FLT3-positive AML: Synergism between FLT3 Inhibitors, Dasatinib/multi-targeted Inhibitors, and JAK Inhibitors," Leukemia, vol. 26, No. 10, Oct. 2012 pp. 2233-2244 (Total 24 pages).
William et al., "Discovery of Kinase Spectrum Selective Macrocycle . . . " J. Med. Chem., vol. 55, No. 1, 2012 (Published Dec. 8, 2011), pp. 169-196, XP-55071583A.
William et al., "Discovery of the Macrocycle . . . " J. Med. Chem., vol. 54, No. 13, 2011 (Published May 23, 2011), pp. 4638-4658, XP-55163145A.
Written Opinion of the International Searching Authority and International Search Report (forms PCT/ISA/237, PCT/ISA/210 and PCT/ISA/220), dated Oct. 22, 2015, for International Application No. PCT/EP2015/070072.

* cited by examiner

*Primary Examiner* — Noble E Jarrell
(74) *Attorney, Agent, or Firm* — Birch, Stewart, Koalsch & Birch, LLP

(57) ABSTRACT

The present invention relates to a compound with the following formula (I): (I) or a salt and/or a pharmaceutically acceptable solvate thereof, in particular for use as a drug, in particular in the treatment of cancer, as well as to the pharmaceutical compositions that contain same and to the methods for preparing same.

20 Claims, No Drawings

DERIVATIVES OF MACROCYCLIC N-ARYL-TRICYCLOPYRIMIDINE-2-AMINE POLYETHERS AS INHIBITORS OF FTL3 AND JAK

The present invention relates to derivatives of macrocyclic N-aryl-tricyclopyrimidine-2-amine polyethers, and to the therapeutic use thereof, particularly in the treatment of cancer, and to the methods for synthesizing same.

Mutations of tyrosine kinase receptors play a crucial role in the pathogenesis of many cancers. For example, the FLT3 receptor is often mutated in acute myeloid leukemia (in about 30% of cases) (Gilliland et al. 2002 Blood 100: 1532-1542). Mutations that result in an increase in the kinase activity of the FLT3 receptor make the tumor cell relatively dependent on this receptor for its proliferation and survival, which thus makes this mutated receptor a relevant target in oncology. Three types of FLT3-activating mutations are identified today in acute myeloid leukemia (AML): internal tandem duplication (FLT3-ITD), which is detected in about 20% of cases, point mutations in the catalytic domain of the receptor, which constitute 6-8% of cases, and point mutations in the juxtamembrane and extracellular domains, which are rare (2%) (Kayser et al. 2014 Leukemia & Lymphoma 55: 243-255).

The new generations of FLT3 inhibitors undergoing clinical evaluation have shown encouraging results for the treatment of AML expressing a mutated form of FLT3. However, most patient responses remain insufficient as they are incomplete and transient, resulting in a relapse rate that remains too high. The causes of these relapses/resistances are many. They can bring into play secondary mutations of the FLT3 receptor or the activation of alternative signaling pathways leading to downstream reactivation of the FLT3 receptor pathway. In addition, whereas the leukemic cells circulating in the patient's blood can be relatively sensitive to the tyrosine kinase inhibitors, the leukemic cells harbored in the patient's marrow are more refractory to treatment, suggesting a role of the bone marrow (microenvironment) in therapeutic resistance (Weisberg et al. 2012 Leukemia 26: 2233-2244). This stromal microenvironment of the leukemic cells, constituted by the bone marrow, would protect the leukemic cells from the effects of tyrosine kinase inhibitors. The IL-6/JAK/STAT signaling pathway is one of the major pathways that would help confer a survival advantage on the leukemic cells expressing a mutated form of FLT3. Moreover, it has been shown that the therapeutic combination of a JAK inhibitor and an FLT3 inhibitor made it possible to increase the effects of FLT3 inhibition and to overcome the resistance induced by the stromal microenvironment (Weisberg et al. op.cit.). Generally, the JAK family of kinases is described as playing an important role in the control of proliferation, cell survival and apoptosis. These JAK kinases are the object of genetic alterations associated with many tumor pathologies, including hematological malignancies.

The present invention has made it possible, surprisingly, to identify compounds having a dual activity as inhibitor of both JAK and FLT3. These compounds further exhibit a remarkable activity.

The present invention more particularly relates to a compound of the following general formula (I):

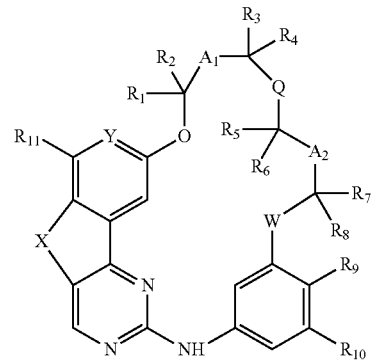

or a pharmaceutically acceptable salt and/or solvate thereof, wherein:

W represents an oxygen or sulfur atom,

X represents a saturated or unsaturated hydrocarbon chain comprising 1 to 3 carbon atoms, optionally substituted by one or more groups selected from a halogen atom, a $(C_1-C_6)$alkyl, oxo (=O), OH and $(C_1-C_6)$alkoxy group, one or more, particularly 1 or 2, carbon atoms of said chain being optionally each replaced, independently of each other, by an oxygen or sulfur atom, Y represents a nitrogen atom or a CRy group wherein Ry represents a hydrogen atom, a halogen atom, a $(C_1-C_6)$alkyl, $(C_1-C_6)$haloalkyl, $(C_1-C_6)$alkoxy, $(C_1-C_6)$haloalkoxy, OH, CN, NO$_2$, NR$_{12}$R$_{13}$, CO$_2$H or CO$_2$(($C_1$-$C_6$)alkyl) group, Q represents a single, double or triple bond, an oxygen or sulfur atom, or a $(C_1-C_6)$alkyl, S(O) or S(O)$_2$ group, $A_1$ and $A_2$ represent, independently of each other, a single bond or a $(C_1-C_6)$alkyl group optionally substituted by an OH group, or $A_1$ and $A_2$ form with Q and the carbon atoms attached to Q an optionally substituted monocyclic carbocycle or heterocycle, $R_1$, $R_2$, $R_3$, $R_4$, $R_5$, $R_6$, $R_7$, and $R_8$ represent, independently of each other, a hydrogen atom or a $(C_1-C_6)$alkyl group, $R_9$ and $R_{10}$ represent, independently of each other, a hydrogen atom, a halogen atom, an optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_1-C_6)$thioalkoxy, CN, NO$_2$, NR$_{14}$R$_{15}$, OH, SH, CO$_2$R$_{54}$, CONR$_{55}$R$_{56}$ group, an optionally substituted carbocycle or an optionally substituted heterocycle, $R_{11}$ represents a hydrogen atom, a halogen atom, or a $(C_1-C_6)$alkyl, $(C_1-C_6)$haloalkyl, $(C_1-C_6)$alkoxy or $(C_1-C_6)$haloalkoxy group, and $R_{12}$, $R_{13}$, $R_{14}$ and $R_{15}$, $R_{54}$, $R_{55}$ and $R_{56}$ represent, independently of each other, a hydrogen atom or an optionally substituted $(C_1-C_6)$alkyl, optionally substituted $(C_2-C_6)$alkenyl, or optionally substituted $(C_2-C_6)$alkynyl group, or $R_{12}$ and $R_{13}$, and/or $R_{14}$ and $R_{15}$ and/or $R_{55}$ and $R_{56}$, independently of each other, form with the nitrogen atom that bears them an optionally substituted nitrogen containing heterocycle.

The stereoisomers of the compounds of general formula (I) also form part of the present invention, as well as the mixtures thereof, in particular in the form of a racemic mixture.

The tautomers of the compounds of general formula (I) also form part of the present invention.

By "stereoisomer" is meant, within the meaning of the present invention, a geometrical isomer (or configurational isomer) or an optical isomer.

Geometrical isomers result from the different position of the substituents on a double bond which can then have a Z or E configuration, also called cis or trans.

Optical isomers result in particular from the different spatial position of the substituents on a carbon atom comprising four different substituents. This carbon atom then constitutes a chiral or asymmetrical center. Optical isomers include diastereoisomers and enantiomers. Optical isomers that are non-superimposable mirror images of each other are called "enantiomers". Optical isomers that are not superimposable mirror images of each other are called "diastereoisomers".

A mixture containing equal quantities of two individual enantiomeric forms of opposite chirality is called a "racemic mixture".

By "tautomer" is meant, within the meaning of the present invention, a constitutional isomer of the compound obtained by prototropy, i.e. by migration of a hydrogen atom and change of location of a double bond. The different tautomers of a compound are generally interconvertible and present in equilibrium in solution, in proportions that can vary according to the solvent used, the temperature or the pH.

In the present invention, by "pharmaceutically acceptable" is meant that which is useful in the preparation of a pharmaceutical composition which is generally safe, nontoxic and neither biologically nor otherwise undesirable and which is acceptable for veterinary as well as human pharmaceutical use.

By "pharmaceutically acceptable salt and/or solvate" of a compound is meant a salt and/or solvate that is pharmaceutically acceptable, as defined herein, and that has the desired pharmacological activity of the parent compound.

The pharmaceutically acceptable salts of the compounds of the present invention comprise the conventional nontoxic salts of the compounds of the invention such as those formed from organic or inorganic acids or from organic or inorganic bases. By way of example, mention may be made of the salts derived from inorganic acids such as hydrochloric, hydrobromic, phosphoric, sulfuric acids, and those derived from organic acids such as acetic, trifluoroacetic, propionic, succinic, fumaric, malic, tartaric, citric, ascorbic, maleic, glutamic, benzoic, salicylic, toluenesulfonic, methanesulfonic, stearic, lactic acids. By way of example, mention may be made of the salts derived from inorganic bases such as sodium hydroxide, potassium hydroxide or calcium hydroxide and the salts derived from organic bases such as lysine or arginine.

These salts can be synthesized from the compounds of the invention containing a base or acid moiety and the corresponding acids or bases according to conventional chemical methods.

The pharmaceutically acceptable solvates of the compounds of the present invention comprise conventional solvates such as those formed during the final step of preparation of the compounds of the invention due to the presence of solvents. By way of example, mention may be made of the solvates due to the presence of water (hydrates) or of ethanol.

The term "halogen" represents a fluorine, chlorine, bromine or iodine.

By "$(C_1\text{-}C_6)$alkyl" group is meant, in the meaning of the present invention, a linear or branched, saturated hydrocarbon chain having 1 to 6, particularly 1 to 4, carbon atoms. By way of example, mention may be made of methyl, ethyl, propyl, isopropyl, butyl, isobutyl, sec-butyl, tert-butyl, pentyl or hexyl groups.

By "$(C_2\text{-}C_6)$alkenyl" group is meant, in the meaning of the present invention, a linear or branched hydrocarbon chain having at least one double bond and having 2 to 6, particularly 2 to 4, carbon atoms. By way of example, mention may be made of ethenyl or allyl groups.

By "$(C_2\text{-}C_6)$alkynyl" group is meant, in the meaning of the present invention, a linear or branched hydrocarbon chain having at least one triple bond and having 2 to 6, particularly 2 to 4, carbon atoms. By way of example, mention may be made of ethynyl or propynyl groups.

By "$(C_1\text{-}C_6)$haloalkyl" is meant, in the meaning of the present invention, a $(C_1\text{-}C_6)$alkyl group, as defined above, wherein one or more hydrogen atoms have been each replaced by a halogen atom as defined above. It may be in particular a $CF_3$ group.

By "$(C_1\text{-}C_6)$alkoxy" group is meant, in the meaning of the present invention, a $(C_1\text{-}C_6)$alkyl group as defined above, attached to the rest of the molecule via an oxygen atom. By way of example, mention may be made of methoxy, ethoxy, propoxy, isopropoxy, butoxy or tert-butoxy groups.

By "$(C_1\text{-}C_6)$haloalkoxy" is meant, in the meaning of the present invention, a $(C_1\text{-}C_6)$haloalkyl group, as defined above, attached to the rest of the molecule via an oxygen atom. It may be in particular an $OCF_3$ group.

By "$(C_1\text{-}C_6)$thioalkoxy" group is meant, in the meaning of the present invention, a $(C_1\text{-}C_6)$alkyl group as defined above, attached to the rest of the molecule via a sulfur atom. By way of example, mention may be made of thiomethoxy, thioethoxy, thiopropoxy, thio-isopropoxy, thiobutoxy or thio-tert-butoxy groups.

By "$(C_1\text{-}C_6)$alkyl-amino" group is meant, in the meaning of the present invention, a $(C_1\text{-}C_6)$alkyl group, as defined above, attached to the rest of the molecule via an NH group. By way of example, mention may be made of methylamino, ethylamino, propylamino or butylamino groups.

By "di($(C_1\text{-}C_6)$alkyl)amino" group is meant, in the meaning of the present invention, a $(C_1\text{-}C_6)$alkyl group, as defined above, attached to the rest of the molecule via an NAlk group wherein Alk represents a $(C_1\text{-}C_6)$alkyl group as defined above. By way of example, mention may be made of dimethylamino, diethylamino, methylethylamino groups, etc.

By "carbocycle" is meant, in the meaning of the present invention, a saturated, unsaturated or aromatic monocyclic or polycyclic hydrocarbon system comprising 3 to 12 carbon atoms. The polycyclic system comprises at least 2, particularly 2 or 3, fused or bridged rings. Each ring of the monocyclic or polycyclic system comprises advantageously 3 to 8, particularly 4 to 7, in particular 5 or 6, carbon atoms. By way of example, mention may be made of an adamantyl, cyclohexyl, cyclopentyl, cyclobutyl, cyclopropyl, cyclohexenyl, phenyl, naphthyl group.

By "aryl" is meant, in the meaning of the present invention, an aromatic hydrocarbon group having preferably 6 to 10 carbon atoms, and comprising one or more fused rings, such as for example a phenyl or naphthyl group. Advantageously, it is phenyl.

By "aryl-$(C_1\text{-}C_6)$alkyl" is meant, in the meaning of the present invention, an aryl group as defined above, attached to the rest of the molecule via a $(C_1\text{-}C_6)$alkyl chain as defined above. By way of example, mention may be made of the benzyl group.

By "$(C_1\text{-}C_6)$alkyl-aryl" is meant, in the meaning of the present invention, a $(C_1\text{-}C_6)$alkyl group as defined above, attached to the rest of the molecule via an aryl group as defined above. By way of example, mention may be made of the tolyl group ($CH_3Ph$).

By "heterocycle" is meant, in the meaning of the present invention, a saturated, unsaturated or aromatic monocyclic or bicyclic hydrocarbon group, preferably saturated or unsaturated but non-aromatic, containing 3 to 12 carbon atoms, wherein 1 to 4, particularly 1 or 2, carbon atoms are each replaced, independently of each other, by a heteroatom selected from N, O and S, particularly selected from N and O. The bicyclic group comprises two fused or bridged rings. Each ring of the monocyclic group or of the bicyclic group comprises advantageously 3 to 8, particularly 4 to 7, in particular 5 or 6, carbon atoms or heteroatoms forming the ring. By way of example, mention may be made of azetidine, oxetane, thiooxetane, pyrrolidine, pyrroline, pyrrole, tetrahydrofuran, dihydrofuran, furan, tetrahydrothiophene, dihydrothiophene, thiophene, piperidine, dihydropyridine, tetrahydropyridine, pyridine, pyran, dihydropyran, tetrahydropyran, thiopyran, dihydrothiopyran, tetrahydrothiopyran, morpholine, thiomorpholine, piperazine, homopiperazine, azepine, pyrazine, pyrimidine, pyridazine, perhydropyrrolo[3,4-c]pyrrole, 2,5-diazabicyclo[4.2.0]octane, 2,5-diazabicyclo[2.2.1]heptane, 3,8-diazabicyclo[3.2.1]octane and imidazole heterocycles. Preferably, the heterocycle will be non-aromatic and can be in particular an azetidine, oxetane, thiooxetane, pyrrolidine, pyrroline, tetrahydrofuran, dihydrofuran, tetrahydrothiophene, dihydrothiophene, piperidine, dihydropyridine, tetrahydropyridine, pyran, dihydropyran, tetrahydropyran, thiopyran, dihydrothiopyran, tetrahydrothiopyran, morpholine, thiomorpholine, piperazine, homopiperazine (or diazepane), perhydropyrrolo[3,4-c]pyrrole, 2,5-diazabicyclo[4.2.0]octane, 3,8-diazabicyclo[3.2.1]octane and 2,5-diazabicyclo[2.2.1]heptane ring.

By "nitrogen containing heterocycle" is meant, in the meaning of the present invention, a heterocycle as defined above comprising at least one nitrogen atom, in particular non-aromatic, preferably saturated. It can be in particular a monocyclic group or a bicyclic group each ring of which comprises 5 to 7, preferably 5 or 6, members and optionally comprising, in addition to the nitrogen atom, another heteroatom preferably selected from oxygen and nitrogen. It will be in particular a piperidine, optionally bridged piperazine (e.g. piperazine, 2,5-diazabicyclo[4.2.0]octane, 3,8-diazabicyclo[3.2.1]octane or 2,5-diazabicyclo[2.2.1]heptane group; particularly a piperazine, 2,5-diazabicyclo[4.2.0]octane or 2,5-diazabicyclo[2.2.1]heptane), morpholine, perhydropyrrolo[3,4-c]pyrrole, diazepane (e.g. 1,3-diazepane or 1,4-diazepane) or pyrrolidine group.

By "fused" rings is meant, in the meaning of the present invention, two rings attached to each other by two adjacent carbon atoms.

By "bridged" rings is meant, in the meaning of the present invention, two rings attached to each other by two non-adjacent carbon atoms.

By "bridged piperazine" is meant, in the meaning of the present invention, a piperazine ring wherein two non-adjacent carbon atoms are connected by a saturated or unsaturated hydrocarbon chain, preferably saturated, comprising advantageously 1 to 5, particularly 1 to 3, preferably 1 or 2, carbon atoms. It can be in particular a 2,5-diazabicyclo[4.2.0]octane, a 3,8-diazabicyclo[3.2.1]octane or a 2,5-diazabicyclo[2.2.1]heptane.

By "unsaturated" group is meant, in the meaning of the present invention, a group comprising at least one C=C or C≡C bond.

By "unsaturated" ring is meant, in the meaning of the present invention, a ring comprising at least one C=C bond but non-aromatic.

By "optionally substituted" group is meant, in the meaning of the present invention, a group optionally substituted by one or more substituents. This/these substituent(s) may be selected particularly from:
  a halogen atom,
  a ($C_1$-$C_6$)alkyl group optionally substituted by one or more groups selected from a halogen atom, $OR_{16}$, $SR_{17}$, $NR_{18}R_{19}$, a carbocycle and a heterocycle,
  oxo (=O), CN, $NO_2$, $OR_{20}$, $SR_{21}$, $NR_{22}R_{23}$, $C(O)R_{24}$, $CO_2R_{25}$, $OC(O)R_{26}$, $S(O)R_{27}$, $SO_2R_{28}$, $NR_{29}C(O)R_{30}$, $C(O)NR_{31}R_{32}$, $NR_{33}CO_2R_{34}$, $OC(O)NR_{35}R_{36}$, $NR_{37}CONR_{39}R_{39}$ and $OCO_2R_{40}$ groups,
  a carbocycle optionally substituted by one or more groups selected from a halogen atom, a ($C_1$-$C_6$)alkyl group, oxo (=O), $OR_{41}$, $SR_{42}$ and $NR_{43}R_{44}$,
  a heterocycle optionally substituted by one or more groups selected from a halogen atom, a ($C_1$-$C_6$)alkyl group, oxo (=O), $OR_{45}$, $SR_{46}$ and $NR_{47}R_{48}$, and
  an —O($CH_2$)$_n$O— group wherein n represents an integer between 1 and 5, particularly between 2 and 3 (the two oxygens of this group can be attached to the same atom or to two different atoms, advantageously they are attached to the same atom, in particular to the same carbon atom, making it possible in this case to form a cyclic acetal),
wherein:
  $R_{16}$ to $R_{48}$ represent, independently of each other, a hydrogen atom, a ($C_1$-$C_6$)alkyl, aryl, aryl-($C_1$-$C_6$)alkyl, heterocycle or heterocycle-($C_1$-$C_6$)alkyl group,
  the aryl ring of these groups being optionally substituted by one or more groups selected from a halogen atom and a ($C_1$-$C_6$)alkyl group, and
  the heterocyclic ring of these groups being optionally substituted by one or more groups selected from a halogen atom, a ($C_1$-$C_6$)alkyl group, and oxo(=O), or
  —$R_{22}$ and $R_{23}$, $R_{31}$ and $R_{32}$, $R_{35}$ and $R_{36}$, $R_{38}$ and $R_{39}$, $R_{43}$ and $R_{44}$, and/or $R_{47}$ and $R_{48}$ form together, with the nitrogen atom that bears them, a nitrogen containing heterocycle optionally substituted by one or more groups selected from a halogen atom, a ($C_1$-$C_6$)alkyl group, and oxo(=O).

X will represent more particularly a saturated or unsaturated hydrocarbon chain comprising 1 to 3, particularly 1 or 2, carbon atoms, optionally substituted by one or more groups selected from a halogen atom, a ($C_1$-$C_6$)alkyl, oxo, OH and ($C_1$-$C_6$)alkoxy group, one carbon atom of said chain being optionally replaced by an oxygen or sulfur atom.

X will represent in particular a saturated or unsaturated hydrocarbon chain comprising 1 to 3, particularly 1 or 2, carbon atoms, one carbon atom of said chain being optionally replaced by an oxygen or sulfur atom.

X will represent advantageously a saturated or unsaturated hydrocarbon chain comprising 1 to 3, particularly 1 or 2, carbon atoms, and more particularly a $CH_2$—$CH_2$ or CH=CH chain.

Y will represent more particularly a nitrogen atom or a CRy group wherein Ry represents a hydrogen atom, a halogen atom, a ($C_1$-$C_6$)alkyl, ($C_1$-$C_6$)haloalkyl, ($C_1$-$C_6$)alkoxy, ($C_1$-$C_6$)haloalkoxy, $NR_{12}R_{13}$, $CO_2H$ or $CO_2$(($C_1$-$C_6$)alkyl) group, with $R_{12}$ and $R_{13}$ representing, independently of each other, a hydrogen atom or a ($C_1$-$C_6$)alkyl group optionally substituted by one or more halogen atoms, or $R_{12}$ and $R_{13}$ form with the nitrogen atom that bears them a preferably non-aromatic 5- or 6-membered heterocycle, optionally comprising another heteroatom selected from O, N and S, and particularly O and N, said heterocycle being optionally substituted by a $(C_1-C_6)$alkyl group.

Y will represent more particularly a nitrogen atom or a CRy group wherein Ry represents a hydrogen atom, a halogen atom, a $(C_1-C_6)$alkyl, $(C_1-C_6)$haloalkyl, $(C_1-C_6)$alkoxy, $(C_1-C_6)$haloalkoxy or $NR_{12}R_{13}$ group, wherein $R_{12}$ and $R_{13}$ represent, independently of each other, a hydrogen atom or a $(C_1-C_6)$alkyl group optionally substituted by one or more halogen atoms, or $R_{12}$ and $R_{13}$ form with the nitrogen atom that bears them a preferably non-aromatic 5- or 6-membered heterocycle, optionally comprising another heteroatom selected from O, N and S, and particularly O and N, said heterocycle being optionally substituted by a $(C_1-C_6)$alkyl group.

Y will represent more particularly a nitrogen atom or a CRy group wherein Ry represents a hydrogen atom, a halogen atom, a $(C_1-C_6)$alkyl, $(C_1-C_6)$alkoxy, OH, or $NR_{12}R_{13}$ group, wherein $R_{12}$ and $R_{13}$ represent, independently of each other, a hydrogen atom or a $(C_1-C_6)$alkyl group.

Y will represent in particular a CRy group wherein Ry is as defined according to one of the previous definitions. Ry will represent in particular a hydrogen atom, a halogen atom, a $(C_1-C_6)$alkyl or $(C_1-C_6)$haloalkyl group; advantageously a hydrogen atom or a halogen atom (e.g. F). Y will represent in particular a CH or CF group.

W can represent more particularly an oxygen atom.

Q will represent in particular a single or double bond, an oxygen atom, or a $(C_1-C_6)$alkyl group.

Q will represent more particularly an oxygen atom.

$A_1$ and $A_2$ represent in particular, independently of each other, a single bond or a $(C_1-C_6)$alkyl group optionally substituted by an OH group, or $A_1$ and $A_2$ form with Q and the carbon atoms attached to Q a monocyclic carbocycle or heterocycle optionally substituted by one or more groups selected from OH, $(C_1-C_6)$alkyl and oxo (=O).

The monocyclic carbocycle can be in particular a $C_3$ to $C_6$, particularly $C_5$ or $C_6$, monocyclic carbocycle, for example a cyclopropyl, a cyclobutyl, a cyclopentyl or a cyclohexyl.

The monocyclic heterocycle can be in particular a $C_3$ to $C_6$, particularly $C_5$ or $C_6$, monocyclic heterocycle, preferably non-aromatic, comprising advantageously an oxygen atom, for example an oxirane, an oxetane, a tetrahydrofuran or a tetrahydropyran.

$A_1$ and $A_2$ will represent in particular, independently of each other, a single bond or a $(C_1-C_6)$alkyl group optionally substituted by an OH group, and particularly a single bond or a $(C_1-C_6)$alkyl group.

$A_1$ and $A_2$ will each represent in particular a single bond.

$R_1$, $R_2$, $R_3$, $R_4$, $R_5$, $R_6$, $R_7$ and $R_8$ will represent more particularly a hydrogen atom.

According to a particular embodiment, W and Q each represent, independently of each other, O or S, preferably O, and $A_1$ and $A_2$ each represent a single bond.

According to another particular embodiment, W=Q=O, $A_1$ and $A_2$ each represent a single bond, and $R_1=R_2=R_3=R_4=R_5=R_6=R_7=R_8$=H.

$R_{11}$ will represent in particular a hydrogen atom, a halogen atom, a $(C_1-C_6)$alkyl or $(C_1-C_6)$alkoxy group. $R_{11}$ will represent more particularly a hydrogen atom, a halogen atom, or a $(C_1-C_6)$alkyl group. Advantageously, $R_{11}$ will represent a hydrogen atom.

$R_9$ and $R_{10}$ represent, independently of each other, a hydrogen atom, a halogen atom, an optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_1-C_6)$thioalkoxy group, CN, $NO_2$, $NR_{14}R_{15}$, OH, SH, $CO_2R_{54}$, $CONR_{55}R_{56}$, an optionally substituted carbocycle or an optionally substituted heterocycle.

$R_9$ and $R_{10}$ represent more particularly, independently of each other, a hydrogen atom, a halogen atom, an optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_1-C_6)$thioalkoxy group, $NR_{14}R_{15}$, $CONR_{55}R_{56}$, an optionally substituted carbocycle or an optionally substituted heterocycle, notably wherein $R_{15} \neq H$ and $R_{55} \neq H$.

$R_9$ and $R_{10}$ represent in particular, independently of each other, a hydrogen atom, a halogen atom, an optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_1-C_6)$thioalkoxy group, $NR_{14}R_{15}$, or an optionally substituted heterocycle, notably wherein $R_{15} \neq H$.

$R_9$ and $R_{10}$ represent in particular, independently of each other, a hydrogen atom, a halogen atom or a $(C_1-C_6)$alkyl, $(C_2-C_6)$alkenyl, $(C_2-C_6)$alkynyl, $(C_1-C_6)$alkoxy, $(C_1-C_6)$thioalkoxy, $(C_1-C_6)$alkyl-amino, di$((C_1-C_6)$alkyl)amino or heterocycle group, said group being optionally substituted.

$R_9$ and $R_{10}$ can represent more particularly, independently of each other, a hydrogen atom or an optionally substituted heterocycle.

In the preceding definitions of $R_9$ and $R_{10}$, $R_{14}$ and $R_{15}$ represent, independently of each other, a hydrogen atom or an optionally substituted $(C_1-C_6)$alkyl, optionally substituted $(C_2-C_6)$alkenyl, or optionally substituted $(C_2-C_6)$alkynyl group, or $R_{14}$ and $R_{15}$ form with the nitrogen atom that bears them an optionally substituted nitrogen containing heterocycle. In particular, $R_{14}$ can represent a hydrogen atom or a $(C_1-C_6)$alkyl group and $R_{15}$ can represent a hydrogen atom or an optionally substituted $(C_1-C_6)$alkyl, optionally substituted $(C_2-C_6)$alkenyl, or optionally substituted $(C_2-C_6)$alkynyl group, or $R_{14}$ and $R_{15}$ will form with the nitrogen atom that bears them an optionally substituted nitrogen containing heterocycle. Advantageously, $R_{14}$ will represent a hydrogen atom or a $(C_1-C_6)$alkyl group and $R_{15}$ will represent a hydrogen atom or an optionally substituted $(C_1-C_6)$alkyl group, or $R_{14}$ and $R_{15}$ will form with the nitrogen atom that bears them an optionally substituted nitrogen containing heterocycle. Preferably, the optionally substituted nitrogen containing heterocycle will be a particularly non-aromatic, preferably saturated monocyclic or bicyclic nitrogen containing heterocycle, each ring of which comprises 5 to 7, preferably 5 or 6, members, optionally comprising 1 heteroatom in addition to the nitrogen atom selected from N and O, such as an optionally bridged piperazine, piperidine, morpholine, perhydropyrrolo[3,4-c]pyrrole, diazepane (e.g. 1,3-diazepane or 1,4-diazepane) or pyrrolidine ring, the heterocycle being optionally substituted particularly by one or more groups selected from a halogen atom, a $(C_1-C_6)$alkyl group and oxo(=O).

Preferentially, the optionally bridged piperazine will be a piperazine, 2,5-diazabicyclo[4.2.0]octane, 3,8-diazabicyclo[3.2.1]octane or 2,5-diazabicyclo[2.2.1]heptane ring; particularly a piperazine, 2,5-diazabicyclo[4.2.0]octane or 2,5-diazabicyclo[2.2.1]heptane ring.

In the preceding definitions of $R_9$ and $R_{10}$, a carbocycle is more particularly a $C_3$ to $C_6$, particularly $C_5$ or $C_6$, monocyclic carbocycle, particularly non-aromatic, for example a cyclopropyl, a cyclobutyl, a cyclopentyl, a cyclohexyl or a cyclohexenyl.

In the preceding definitions of $R_9$ and $R_{10}$, a heterocycle is more particularly a saturated, unsaturated or aromatic, preferably saturated or unsaturated, monocyclic or bicyclic heterocycle, each ring having 5, 6 or 7 members, preferably 5 or 6 members, comprising 1 or 2 heteroatoms selected from N, O and S, particularly from N and O, and preferably comprising at least one nitrogen atom, the heteroatom(s) being preferably N. The heterocycle can be for example a pyrrolidine, pyrroline, pyrrole, tetrahydrofuran, dihydrofuran, furan, tetrahydrothiophene, dihydrothiophene, thiophene, piperidine, dihydropyridine, tetrahydropyridine, pyridine, pyran, dihydropyran, tetrahydropyran, thiopyran, dihydrothiopyran, tetrahydrothiopyran, morpholine, thiomorpholine, piperazine, pyrazine, pyrimidine, pyridazine, perhydropyrrolo[3,4-c]pyrrole, 2,5-diazabicyclo[4.2.0]octane, 3,8-diazabicyclo[3.2.1]octane 2,5-diazabicyclo[2.2.1]heptane or imidazole ring. The heterocycle will be in particular a pyrrolidine, pyrroline, tetrahydrofuran, dihydrofuran, tetrahydrothiophene, dihydrothiophene, piperidine, dihydropyridine, tetrahydropyridine, pyran, dihydropyran, tetrahydropyran, thiopyran, dihydrothiopyran, tetrahydrothiopyran, morpholine, thiomorpholine, piperazine, perhydropyrrolo[3,4-c]pyrrole, 2,5-diazabicyclo[4.2.0]octane, 3,8-diazabicyclo[3.2.1]octane or 2,5-diazabicyclo[2.2.1]heptane ring. The heterocycle will be in particular a pyrrolidine, pyrroline, tetrahydrofuran, dihydrofuran, piperidine, dihydropyridine, tetrahydropyridine, pyran, dihydropyran, tetrahydropyran, morpholine, piperazine or perhydropyrrolo[3,4-c]pyrrole ring. The heterocycle will be more particularly a pyrrolidine, pyrroline, piperidine, dihydropyridine, tetrahydropyridine, piperazine or perhydropyrrolo[3,4-c]pyrrole ring. The heterocycle can be advantageously a pyrrolidine, piperidine, tetrahydropyridine (particularly 1,2,3,6-tetrahydropyridine), piperazine or perhydropyrrolo[3,4-c]pyrrole ring. Advantageously, the heterocycle will be a particularly non-aromatic, preferably saturated monocyclic or bicyclic nitrogen containing heterocycle, each ring of which comprises 5 to 7, preferably 5 or 6, members, optionally comprising 1 heteroatom selected from N and O in addition to the nitrogen atom, such as an optionally bridged piperazine (e.g. piperazine, 2,5-diazabicyclo[4.2.0]octane, 3,8-diazabicyclo[3.2.1]octane or 2,5-diazabicyclo[2.2.1]heptane), piperidine, morpholine, perhydropyrrolo[3,4-c]pyrrole, diazepane (e.g. 1,3-diazepane or 1,4-diazepane), tetrahydropyridine (particularly 1,2,3,6-tetrahydropyridine) or pyrrolidine ring. It can be in particular a saturated monocyclic or bicyclic nitrogen containing heterocycle, each ring of which comprises 5 or 6 members, optionally comprising 1 heteroatom selected from N and O in addition to the nitrogen atom, such as an optionally bridged piperazine (e.g. piperazine, 2,5-diazabicyclo[4.2.0]octane, 3,8-diazabicyclo[3.2.1]octane or 2,5-diazabicyclo[2.2.1]heptane), piperidine, morpholine, perhydropyrrolo[3,4-c]pyrrole or pyrrolidine ring, particularly an optionally bridged piperazine, in particular a piperazine. The nitrogen containing heterocycle will be preferably attached to the rest of the molecule by its nitrogen atom.

In the preceding definitions of $R_9$, $R_{10}$, $R_{14}$ and $R_{15}$, an optionally substituted group or ring is a group or ring optionally substituted by one or more substituents, advantageously selected from:
  a halogen atom,
  a $(C_1-C_6)$alkyl group optionally substituted by one or more groups selected from a halogen atom, $OR_{16}$, $SR_{17}$, $NR_{18}R_{19}$, a carbocycle and a heterocycle,
  oxo (=O), CN, $NO_2$, $OR_{20}$, $SR_{21}$, $NR_{22}R_{23}$, $C(O)R_{24}$, $CO_2R_{25}$, $OC(O)R_{26}$, $S(O)R_{27}$, $SO_2R_{28}$, $NR_{29}C(O)R_{30}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups,
  a carbocycle optionally substituted by one or more groups selected from a halogen atom, a $(C_1-C_6)$alkyl group, oxo (=O), $OR_{41}$, $SR_{42}$ and $NR_{43}R_{44}$,
  a heterocycle optionally substituted by one or more groups selected from a halogen atom, a $(C_1-C_6)$alkyl group, oxo (=O), $OR_{45}$, $SR_{46}$ and $NR_{47}R_{48}$, and
  an $-O(CH_2)_nO-$ group wherein n represents an integer between 1 and 5, particularly between 2 and 3 (the two oxygens of this group can be attached to the same atom or to two different atoms, advantageously they are attached to the same atom, in particular to the same carbon atom, making it possible in this case to form a cyclic acetal),
wherein:
  $R_{16}$ to $R_{48}$ represent, independently of each other, a hydrogen atom, a $(C_1-C_6)$alkyl, aryl, aryl-$(C_1-C_6)$alkyl, heterocycle or heterocycle-$(C_1-C_6)$alkyl group,
    the aryl ring of these groups being optionally substituted by one or more groups selected from a halogen atom and a $(C_1-C_6)$alkyl group, and
    the heterocyclic ring of these groups being optionally substituted by one or more groups selected from a halogen atom, a $(C_1-C_6)$alkyl group, and oxo(=O),
  or
  $R_{22}$ and $R_{23}$, $R_{31}$ and $R_{32}$, $R_{35}$ and $R_{36}$, $R_{38}$ and $R_{39}$, $R_{43}$ and $R_{44}$, and/or $R_{47}$ and $R_{48}$ form together, with the nitrogen atom that bears them, a nitrogen containing heterocycle optionally substituted by one or more groups selected from a halogen atom, a $(C_1-C_6)$alkyl group, and oxo(=O).

In the preceding definitions of $R_9$, $R_{10}$, $R_{14}$ and $R_{15}$, the optionally substituted groups or rings are in particular optionally substituted by one or more substituents selected from:
  a halogen atom,
  a $(C_1-C_6)$alkyl group optionally substituted by one or more groups selected from a halogen atom, $OR_{16}$, $NR_{18}R_{19}$, a carbocycle and a heterocycle,
  oxo (=O), $OR_{20}$, $NR_{22}R_{23}$, $C(O)R_{24}$, $CO_2R_{25}$, $OC(O)R_{26}$, $NR_{29}C(O)R_{30}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups, and more particularly oxo (=O), $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups,
  a $C_3$ to $C_6$ carbocycle optionally substituted by one or more groups selected from a halogen atom, a $(C_1-C_6)$alkyl group, oxo (=O), $OR_{41}$ and $NR_{43}R_{44}$,
  a preferably saturated 3- to 6-membered heterocycle comprising 1 or 2 heteroatoms selected from N and O, optionally substituted by one or more groups selected from a halogen atom, a $(C_1-C_6)$alkyl group, oxo (=O), $OR_{45}$ and $NR_{47}R_{48}$, and
  an $-O(CH_2)_nO-$ group wherein n represents an integer equal to 2 or 3 (the two oxygens of this group can be attached to the same atom or to two different atoms, advantageously they are attached to the same atom, in particular to the same carbon atom, making it possible in this case to form a cyclic acetal),
wherein:
  $R_{16}$, $R_{18}$ to $R_{20}$, $R_{22}$ to $R_{26}$, $R_{29}$ to $R_{41}$, $R_{43}$ to $R_{45}$, $R_{47}$ and $R_{48}$ represent, independently of each other, a hydrogen atom, a $(C_1-C_6)$alkyl, aryl, aryl-$(C_1-C_6)$alkyl, heterocycle or heterocycle-$(C_1-C_6)$alkyl group, particularly a hydrogen atom, a $(C_1-C_6)$alkyl, aryl, or aryl-$(C_1-C_6)$ alkyl group, in particular a hydrogen atom, or a $(C_1-C_6)$alkyl group, the aryl ring of these groups being a phenyl group and, being optionally substituted by one or more groups selected from a halogen atom and a $(C_1-C_6)$alkyl group, and the heterocyclic ring of these groups being a 3- to 6-membered, particularly a 5- or 6-membered, heterocycle comprising 1 or 2 heteroatoms selected from N and O and being optionally substituted by one or more groups selected from a halogen atom, a $(C_1-C_6)$alkyl group, and oxo(=O), or $R_{22}$ and $R_{23}$, $R_{31}$ and $R_{32}$, $R_{35}$ and $R_{36}$, $R_{38}$ and $R_{39}$, $R_{43}$ and $R_{44}$, and/or $R_{47}$ and $R_{48}$ form together, with the nitrogen atom that bears them, a 5- or 6-membered nitrogen containing heterocycle, particularly non-aromatic, preferably saturated, optionally comprising 1 heteroatom in addition to the nitrogen atom selected from N and O, such as a piperazine, piperidine, morpholine or pyrrolidine ring, the heterocycle being optionally substituted by one or more groups selected from a halogen atom, a $(C_1-C_6)$alkyl group, and oxo (=O).

In the preceding definitions of $R_9$, $R_{10}$, $R_{14}$ and $R_{15}$, the optionally substituted groups or rings are advantageously optionally substituted by one or more substituents selected from:

a halogen atom, a $(C_1-C_6)$alkyl group optionally substituted by one or more groups selected from a halogen atom, $OR_{16}$ and $NR_{18}R_{19}$, oxo (=O), $R_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups, a $C_3$ to $C_6$ carbocycle optionally substituted by one or more groups selected from a halogen atom, a $(C_1-C_6)$alkyl group, oxo (=O), $OR_{41}$ and $NR_{43}R_{44}$, a preferably saturated 3- to 6-membered heterocycle comprising 1 or 2 heteroatoms selected from N and O, optionally substituted by one or more groups selected from a halogen atom, a $(C_1-C_6)$alkyl group, oxo (=O), $OR_{45}$ and $NR_{47}R_{48}$, and an —O(CH$_2$)$_n$O— group wherein n represents an integer equal to 2 or 3 (the two oxygens of this group can be attached to the same atom or to two different atoms, advantageously they are attached to the same atom, in particular to the same carbon atom, making it possible in this case to form a cyclic acetal), wherein:

$R_{16}$, $R_{18}$ to $R_{20}$, $R_{22}$, $R_{23}$, $R_{25}$, $R_{31}$ to $R_{41}$, $R_{43}$ to $R_{45}$, $R_{47}$ and $R_{48}$ represent, independently of each other, a hydrogen atom, a $(C_1-C_6)$alkyl, aryl, or aryl-$(C_1-C_6)$ alkyl group, in particular a hydrogen atom, or a $(C_1-C_6)$alkyl group, the aryl ring of these groups being preferably a phenyl group and being optionally substituted by one or more groups selected from a halogen atom and a $(C_1-C_6)$alkyl group, or $R_{22}$ and $R_{23}$, $R_{31}$ and $R_{32}$, $R_{35}$ and $R_{36}$, $R_{38}$ and $R_{39}$, and/or $R_{47}$ and $R_{48}$ form together, with the nitrogen atom that bears them, a 5- or 6-membered nitrogen containing heterocycle, particularly non-aromatic, preferably saturated, optionally comprising 1 heteroatom in addition to the nitrogen atom selected from N and O, such as a piperazine, piperidine, morpholine or pyrrolidine ring, the heterocycle being optionally substituted by one or more groups selected from a halogen atom, a $(C_1-C_6)$alkyl group, and oxo(=O).

Groups $R_9$ and $R_{10}$ can in particular represent, independently of each other:

a hydrogen or halogen atom, a $(C_1-C_6)$alkyl, $(C_2-C_6)$alkenyl, $(C_2-C_6)$alkynyl, $(C_1-C_6)$alkoxy, $(C_1-C_6)$thioalkoxy, $(C_1-C_6)$alkyl-amino or di($(C_1-C_6)$alkyl)amino group, said group being optionally substituted by one or more substituents selected from a halogen atom, $OR_{20}$, $NR_{22}R_{23}$, $C(O)R_{24}$, $CO_2R_{25}$, $OC(O)R_{26}$, $NR_{29}C(O)R_{30}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$; particularly selected from $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$, and $OCO_2R_{40}$; particularly selected from $NR_{22}R_{23}$, $NR_{33}CO_2R_{34}$ and $NR_{37}CONR_{38}R_{39}$, or a monocyclic or bicyclic heterocycle, each ring having 5, 6 or 7 members, preferably 5 or 6 members, comprising 1 or 2 heteroatoms selected from N and O, preferably saturated or containing a double bond but non-aromatic, (the heterocycle can be in particular an optionally bridged piperazine (e.g. piperazine, 2,5-diazabicyclo[4.2.0]octane, 3,8-diazabicyclo[3.2.1]octane or 2,5-diazabicyclo[2.2.1]heptane), piperidine, perhydropyrrolo[3,4-c]pyrrole, tetrahydropyridine or pyrrolidine ring; particularly a piperazine, piperidine, pyrrolidine, perhydropyrrolo[3,4-c]pyrrole or tetrahydropyridine ring) optionally substituted by one or more substituents selected from:

a halogen atom, a $(C_1-C_6)$alkyl group optionally substituted by one or more groups selected from a halogen atom, $OR_{16}$, $NR_{18}R_{19}$, a $C_3$ to $C_6$ monocyclic carbocycle (particularly saturated) and a 3- to 6-membered monocyclic heterocycle (particularly saturated); preferably optionally substituted by one or more groups selected from a halogen atom, $OR_{16}$ and $NR_{18}R_{19}$, oxo (=O), $OR_{20}$, $NR_{22}R_{23}$, $C(O)R_{24}$, $CO_2R_{25}$, $OC(O)R_{26}$, $NR_{29}C(O)R_{30}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups; and more particularly oxo (=O), $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups, a $C_3$ to $C_6$ carbocycle optionally substituted by one or more groups selected from a halogen atom, a $(C_1-C_6)$alkyl group, oxo (=O), $OR_{41}$ and $NR_{43}R_{44}$, a 3- to 6-membered heterocycle, particularly saturated or unsaturated, preferably saturated, comprising 1 or 2 heteroatoms selected from N and O, optionally substituted by one or more groups selected from a halogen atom, a $(C_1-C_6)$alkyl group, oxo (=O), $OR_{45}$ and $NR_{47}R_{48}$, and an —O(CH$_2$)$_n$O— group wherein n represents an integer equal to 2 or 3 (the two oxygens of this group can be attached to the same atom or to two different atoms, advantageously they are attached to the same atom, in particular to the same carbon atom, making it possible in this case to form a cyclic acetal), wherein:

$R_{16}$, $R_{18}$ to $R_{20}$, $R_{22}$ to $R_{26}$, $R_{29}$ to $R_{41}$, $R_{43}$ to $R_{45}$, $R_{47}$ and $R_{48}$ represent, independently of each other, a hydrogen atom, a $(C_1-C_6)$alkyl, aryl, aryl-$(C_1-C_6)$alkyl, heterocycle or heterocycle-$(C_1-C_6)$alkyl group, particularly a hydrogen atom, a $(C_1-C_6)$alkyl, aryl, or aryl-$(C_1-C_6)$ alkyl group, in particular a hydrogen atom, or a $(C_1-C_6)$alkyl group, the aryl ring of these groups being a phenyl group and being optionally substituted by one or more groups selected from a halogen atom and a $(C_1-C_6)$alkyl group, and the heterocyclic ring of these groups being a 3- to 6-membered, particularly a 5- or 6-membered, heterocycle comprising 1 or 2 heteroatoms selected from N and O, and being optionally substituted by one or more groups selected from a halogen atom, a $(C_1-C_6)$alkyl group and oxo(=O), or $R_{22}$ and $R_{23}$, $R_{31}$ and $R_{32}$, $R_{35}$ and $R_{36}$, $R_{38}$ and $R_{39}$, $R_{43}$ and $R_{44}$, and/or $R_{47}$ and $R_{48}$ form together, with the nitrogen atom that bears them, a 5- or 6-membered nitrogen containing heterocycle, preferably saturated, particularly non-aromatic, optionally comprising 1 heteroatom in addition to the nitrogen atom selected from N and O, such as a piperazine, piperidine, morpholine or pyrrolidine ring, the heterocycle being optionally substituted by one or more groups selected from a halogen atom, a $(C_1-C_6)$alkyl group, and oxo(=O).

Groups $R_9$ and $R_{10}$ can more particularly represent, independently of each other:

a hydrogen or halogen atom, a —Z—$(CH_2)_m$—$R_{49}$ group wherein Z represents a single bond, $CH_2$—$CH_2$, CH=CH, C≡C, O, S or $NR_{50}$; m represents an integer between 1 and 6, particularly between 1 and 4; $R_{50}$ represents a hydrogen atom or a $(C_1-C_6)$alkyl group; and $R_{49}$ represents a halogen atom, $OR_{20}$, $NR_{22}R_{23}$, $C(O)R_{24}$, $CO_2R_{25}$, $OC(O)R_{26}$, $NR_{29}C(O)R_{30}$, $C(O)NR_{31}R_{32}$, $NR_{33}CO_2R_{34}$, $OC(O)NR_{35}R_{36}$, $NR_{37}CONR_{38}R_{39}$ or $OCO_2R_{40}$; particularly $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ or $OCO_2R_{40}$; particularly $NR_{22}R_{23}$, $NR_{33}CO_2R_{34}$, or $NR_{37}CONR_{38}R_{39}$, or a monocyclic or bicyclic heterocycle, each ring having 5, 6 or 7 members, preferably 5 or 6 members, comprising 1 or 2 heteroatoms selected from N and O, preferably saturated or containing a double bond, (the heterocycle can be in particular an optionally bridged piperazine (e.g. piperazine, 2,5-diazabicyclo[4.2.0]octane, 3,8-diazabicyclo[3.2.1]octane or 2,5-diazabicyclo[2.2.1]heptane), piperidine, perhydropyrrolo[3,4-c]pyrrole, tetrahydropyridine or pyrrolidine ring; particularly a piperazine, piperidine, pyrrolidine, perhydropyrrolo[3,4-c]pyrrole or tetrahydropyridine ring) optionally substituted by one or more substituents selected from:

a halogen atom, a $(C_1-C_6)$alkyl group optionally substituted by one or more groups selected from a halogen atom, $OR_{16}$, $NR_{18}R_{19}$, a $C_3$ to $C_6$ monocyclic carbocycle (particularly saturated) and a 3- to 6-membered monocyclic heterocycle (particularly saturated); preferably optionally substituted by one or more groups selected from a halogen atom, $OR_{16}$ and $NR_{18}R_{19}$, oxo (=O), $OR_{20}$, $NR_{22}R_{23}$, $C(O)R_{24}$, $CO_2R_{25}$, $OC(O)R_{26}$, $NR_{29}C(O)R_{30}$, $C(O)NR_{31}R_{32}$, $NR_{33}CO_2R_{34}$, $OC(O)NR_{35}R_{36}$, $NR_{37}CONR_{38}R_{39}$ or $OCO_2R_{40}$ groups; and more particularly oxo (=O), $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ or $OCO_2R_{40}$ groups, a $C_3$ to $C_6$ carbocycle optionally substituted by one or more groups selected from a halogen atom, a $(C_1-C_6)$alkyl group, oxo (=O), $OR_{41}$ and $NR_{43}R_{44}$, a 3- to 6-membered heterocycle, particularly saturated or unsaturated, preferably saturated, comprising 1 or 2 heteroatoms selected from N and O, optionally substituted by one or more groups selected from a halogen atom, a $(C_1-C_6)$alkyl group, oxo (=O), $OR_{45}$ and $NR_{47}R_{48}$, and an —$O(CH_2)_nO$— group wherein n represents an integer equal to 2 or 3 (the two oxygens of this group can be attached to the same atom or to two different atoms, advantageously they are attached to the same atom, in particular to the same carbon atom, making it possible in this case to form a cyclic acetal), wherein:

$R_{16}$, $R_{18}$ to $R_{20}$, $R_{22}$ to $R_{26}$, $R_{29}$ to $R_{41}$, $R_{43}$ to $R_{45}$, $R_{47}$ and $R_{48}$ represent, independently of each other, a hydrogen atom, a $(C_1-C_6)$alkyl, aryl, aryl-$(C_1-C_6)$alkyl, heterocycle or heterocycle-$(C_1-C_6)$alkyl group, particularly a hydrogen atom, a $(C_1-C_6)$alkyl, aryl, or aryl-$(C_1-C_6)$ alkyl group, in particular a hydrogen atom, or a $(C_1-C_6)$alkyl group, the aryl ring of these groups being a phenyl group and being optionally substituted by one or more groups selected from a halogen atom and a $(C_1-C_6)$alkyl group, and the heterocyclic ring of these groups being a 3- to 6-membered, particularly a 5- or 6-membered, heterocycle comprising 1 or 2 heteroatoms selected from N and O, and being optionally substituted by one or more groups selected from a halogen atom, a $(C_1-C_6)$alkyl group and oxo(=O), or $R_{22}$ and $R_{23}$, $R_{31}$ and $R_{32}$, $R_{35}$ and $R_{36}$, $R_{38}$ and $R_{39}$, $R_{43}$ and $R_{44}$, and/or $R_{47}$ and $R_{48}$ form together, with the nitrogen atom that bears them, a 5- or 6-membered nitrogen containing heterocycle, particularly non-aromatic, preferably saturated, optionally comprising 1 heteroatom in addition to the nitrogen atom selected from N and O, such as a piperazine, piperidine, morpholine or pyrrolidine ring, the heterocycle being optionally substituted by one or more groups selected from a halogen atom, a $(C_1-C_6)$alkyl group, and oxo (=O).

According to a particular embodiment of the invention, at least one of $R_9$ and $R_{10}$, and preferably $R_9$, does not represent a hydrogen atom. According to another particular embodiment of the invention, at least one of $R_9$ and $R_{10}$, and preferably $R_9$, does not represent a hydrogen atom or a halogen atom. In these two cases, $R_9$ and $R_{10}$ can be defined according to any one of the preceding embodiments, except that one of the two groups cannot represent a hydrogen atom, in particular cannot represent a hydrogen or halogen atom.

According to still another embodiment of the invention, one of $R_9$ and $R_{10}$ (preferably $R_{10}$) represents a hydrogen atom and the other (preferably $R_9$) does not represent a hydrogen atom, and particularly does not represent a hydrogen atom or a halogen atom. The $R_9$ or $R_{10}$ group not representing a hydrogen atom or a halogen atom can be defined according to any one of the preceding embodiments, except for hydrogen or even halogen.

$R_{10}$ will represent more particularly a hydrogen atom. $R_9$ can then be as defined according to any one of the preceding embodiments, and preferably will not be a hydrogen atom, particularly will not be a hydrogen atom or a halogen atom.

According to a first particular embodiment, X represents a CH$_2$—CH$_2$ or CH=CH chain, Y=CRy, W=Q=O, A$_1$ and A$_2$ each represent a single bond, and R$_1$=R$_2$=R$_3$=R$_4$=R$_5$=R$_6$=R$_7$=R$_8$=R$_{11}$=H.

The compounds of formula (I) thus correspond to the compounds of the following formula (Ia):

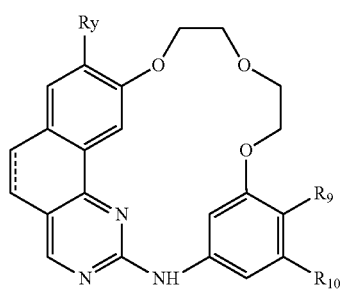

(Ia)

and the pharmaceutically acceptable salts and/or solvates thereof,
wherein:
- === represents a single bond or a double bond,
- Ry is as defined above and advantageously represents a hydrogen atom, a halogen atom, a (C$_1$-C$_6$)alkyl or (C$_1$-C$_6$)haloalkyl group; particularly a hydrogen atom or a halogen atom (e.g. F), and
- R$_9$ and R$_{10}$ are as defined according to any one of the embodiments described above for R$_9$ and R$_{10}$.

According to a second particular embodiment, X represents a CH$_2$—CH$_2$ or CH=CH chain, Y=CRy, W=Q=O, A$_1$ and A$_2$ each represent a single bond, and R$_1$=R$_2$=R$_3$=R$_4$=R$_5$=R$_6$=R$_7$=R$_8$=R$_{10}$=R$_{11}$=H.

The compounds of formula (I) thus correspond to the compounds of the following formula (Ib):

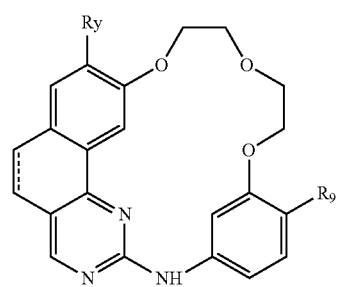

(Ib)

and the pharmaceutically acceptable salts and/or solvates thereof,
wherein:
- === represents a single bond or a double bond,
- Ry is as defined above and advantageously represents a hydrogen atom, a halogen atom, a (C$_1$-C$_6$)alkyl or (C$_1$-C$_6$)haloalkyl group; particularly a hydrogen atom or a halogen atom (e.g. F), and
- R$_9$ is as defined according to any one of the embodiments described above for R$_9$.

According to a particularly advantageous embodiment, the compound according to the invention is a compound of formula (Ib) wherein R$_9$ represents an optionally substituted heterocycle.

Advantageously, the heterocycle will be a particularly non-aromatic, preferably saturated monocyclic or bicyclic nitrogen containing heterocycle, each ring of which comprises 5 to 7, preferably 5 or 6, members, optionally comprising 1 heteroatom selected from N and O in addition to the nitrogen atom, such as an optionally bridged piperazine (e.g. piperazine, 2,5-diazabicyclo[4.2.0]octane, 3,8-diazabicyclo[3.2.1]octane or 2,5-diazabicyclo[2.2.1]heptane), piperidine, morpholine, perhydropyrrolo[3,4-c]pyrrole, diazepane (e.g. 1,3-diazepane or 1,4-diazepane), tetrahydropyridine (particularly 1,2,3,6-tetrahydropyridine) or pyrrolidine ring. It can be in particular a saturated monocyclic or bicyclic nitrogen containing heterocycle, each ring of which comprises 5 or 6 members, optionally comprising 1 heteroatom selected from N and O in addition to the nitrogen atom, such as an optionally bridged piperazine (e.g. piperazine, 2,5-diazabicyclo[4.2.0]octane, 3,8-diazabicyclo[3.2.1]octane or 2,5-diazabicyclo[2.2.1]heptane), piperidine, morpholine, perhydropyrrolo[3,4-c]pyrrole or pyrrolidine ring, particularly an optionally bridged piperazine, in particular a piperazine. The nitrogen containing heterocycle will be preferably attached to the rest of the molecule by its nitrogen atom.

The heterocycle will be in particular optionally substituted by one or more substituents selected from:
- a halogen atom,
- a (C$_1$-C$_6$)alkyl group optionally substituted by one or more groups selected from a halogen atom, OR$_{16}$, SR$_{17}$, NR$_{18}$R$_{19}$, a carbocycle and a heterocycle,
- oxo (=O), CN, NO$_2$, OR$_{20}$, SR$_{21}$, NR$_{22}$R$_{23}$, C(O)R$_{24}$, CO$_2$R$_{25}$, OC(O)R$_{26}$, S(O)R$_{27}$, SO$_2$R$_{28}$, NR$_{29}$C(O)R$_{30}$, C(O)NR$_{31}$R$_{32}$, NR$_{33}$CO$_2$R$_{34}$, OC(O)NR$_{35}$R$_{36}$, NR$_{37}$CONR$_{38}$R$_{39}$ and OCO$_2$R$_{40}$ groups,
- a carbocycle optionally substituted by one or more groups selected from a halogen atom, a (C$_1$-C$_6$)alkyl group, oxo (=O), OR$_{41}$, SR$_{42}$ and NR$_{43}$R$_{44}$,
- a heterocycle optionally substituted by one or more groups selected from a halogen atom, a (C$_1$-C$_6$)alkyl group, oxo (=O), OR$_{45}$, SR$_{46}$ and NR$_{47}$R$_{48}$, and
- an —O(CH$_2$)$_n$O— group wherein n represents an integer between 1 and 5, particularly between 2 and 3 (the two oxygens of this group can be attached to the same atom or to two different atoms, advantageously they are attached to the same atom, in particular to the same carbon atom, making it possible in this case to form a cyclic acetal), wherein:
- R$_{16}$ to R$_{48}$ represent, independently of each other, a hydrogen atom, a (C$_1$-C$_6$)alkyl, aryl, aryl-(C$_1$-C$_6$)alkyl, heterocycle or heterocycle-(C$_1$-C$_6$)alkyl group,
  - the aryl ring of these groups being optionally substituted by one or more groups selected from a halogen atom and a (C$_1$-C$_6$)alkyl group, and
  - the heterocyclic ring of these groups being optionally substituted by one or more groups selected from a halogen atom, a (C$_1$-C$_6$)alkyl group, and oxo(=O), or
- R$_{22}$ and R$_{23}$, R$_{31}$ and R$_{32}$, R$_{35}$ and R$_{36}$, R$_{38}$ and R$_{39}$, R$_{43}$ and R$_{44}$, and/or R$_{47}$ and R$_{48}$ form together, with the nitrogen atom that bears them, a nitrogen containing heterocycle optionally substituted by one or more groups selected from a halogen atom, a (C$_1$-C$_6$)alkyl group, and oxo(=O).

The heterocycle will be advantageously optionally substituted by one or more substituents selected from:
- a halogen atom,
- a $(C_1-C_6)$alkyl group optionally substituted by one or more groups selected from a halogen atom, $OR_{16}$, $NR_{18}R_{19}$, a carbocycle and a heterocycle,
- oxo (=O), $OR_{20}$, $NR_{22}R_{23}$, $C(O)R_{24}$, $CO_2R_{25}$, $OC(O)R_{26}$, $NR_{29}C(O)R_{30}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups, and more particularly oxo (=O), $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups,
- a $C_3$ to $C_6$ carbocycle optionally substituted by one or more groups selected from a halogen atom, a $(C_1-C_6)$ alkyl group, oxo (=O), $OR_{41}$ and $NR_{43}R_{44}$,
- a 3- to 6-membered heterocycle comprising 1 or 2 heteroatoms selected from N and O, preferably saturated, optionally substituted by one or more groups selected from a halogen atom, a $(C_1-C_6)$alkyl group, oxo (=O), $OR_{45}$ and $NR_{47}R_{48}$, and
- an —$O(CH_2)_nO$— group wherein n represents an integer equal to 2 or 3 (the two oxygens of this group can be attached to the same atom or to two different atoms, advantageously they are attached to the same atom, in particular to the same carbon atom, making it possible in this case to form a cyclic acetal), wherein:
$R_{16}$, $R_{18}$ to $R_{20}$, $R_{22}$ to $R_{26}$, $R_{29}$ to $R_{41}$, $R_{43}$ to $R_{45}$, $R_{47}$ and $R_{48}$ represent, independently of each other, a hydrogen atom, a $(C_1-C_6)$alkyl, aryl, aryl-$(C_1-C_6)$alkyl, heterocycle or heterocycle-$(C_1-C_6)$alkyl group, particularly a hydrogen atom, a $(C_1-C_6)$alkyl, aryl, or aryl-$(C_1-C_6)$ alkyl group, in particular a hydrogen atom, or a $(C_1-C_6)$alkyl group,
the aryl ring of these groups being a phenyl group and being optionally substituted by one or more groups selected from a halogen atom and a $(C_1-C_6)$alkyl group, and
the heterocyclic ring of these groups being a 3- to 6-membered, particularly a 5- or 6-membered, heterocycle comprising 1 or 2 heteroatoms selected from N and O and being optionally substituted by one or more groups selected from a halogen atom, a $(C_1-C_6)$alkyl group, and oxo(=O), or
$R_{22}$ and $R_{23}$, $R_{31}$ and $R_{32}$, $R_{35}$ and $R_{36}$, $R_{38}$ and $R_{39}$, $R_{43}$ and $R_{44}$, and/or $R_{47}$ and $R_{48}$ form together, with the nitrogen atom that bears them, a 5- or 6-membered nitrogen containing heterocycle, particularly non-aromatic, preferably saturated, optionally comprising 1 heteroatom in addition to the nitrogen atom selected from N and O, such as a piperazine, piperidine, morpholine or pyrrolidine ring, the heterocycle being optionally substituted by one or more groups selected from a halogen atom, a $(C_1-C_6)$alkyl group, and oxo (=O).

The heterocycle will be in particular optionally substituted by one or more substituents selected from:
- a halogen atom,
- a $(C_1-C_6)$alkyl group optionally substituted by one or more groups selected from a halogen atom, $OR_{16}$ and $NR_{18}R_{19}$,
- oxo (=O), $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups,
- a $C_3$ to $C_6$ carbocycle optionally substituted by one or more groups selected from a halogen atom, a $(C_1-C_6)$ alkyl group, oxo (=O), $OR_{41}$ and $NR_{43}R_{44}$,
- a 3- to 6-membered heterocycle, preferably saturated, comprising 1 or 2 heteroatoms selected from N and O, optionally substituted by one or more groups selected from a halogen atom, a $(C_1-C_6)$alkyl group, oxo (=O), $OR_{45}$ and $NR_{47}R_{48}$, and
- an —$O(CH_2)_nO$— group wherein n represents an integer equal to 2 or 3 (the two oxygens of this group can be attached to the same atom or to two different atoms, advantageously they are attached to the same atom, in particular to the same carbon atom, making it possible in this case to form a cyclic acetal), wherein:
$R_{16}$, $R_{18}$ to $R_{20}$, $R_{22}$, $R_{23}$, $R_{25}$, $R_{31}$ to $R_{41}$, $R_{43}$ to $R_{45}$, $R_{47}$ and $R_{48}$ represent, independently of each other, a hydrogen atom, a $(C_1-C_6)$alkyl, aryl, or aryl-$(C_1-C_6)$ alkyl group, in particular a hydrogen atom, or a $(C_1-C_6)$alkyl group,
the aryl ring of these groups being preferably a phenyl group and being optionally substituted by one or more groups selected from a halogen atom and a $(C_1-C_6)$alkyl group, or
$R_{22}$ and $R_{23}$, $R_{31}$ and $R_{32}$, $R_{35}$ and $R_{36}$, $R_{38}$ and $R_{39}$, and/or $R_{47}$ and $R_{48}$ form together, with the nitrogen atom that bears them, a 5- or 6-membered nitrogen containing heterocycle, particularly non-aromatic, preferably saturated, optionally comprising 1 heteroatom in addition to the nitrogen atom selected from N and O, such as a piperazine, piperidine, morpholine or pyrrolidine ring, the heterocycle being optionally substituted by one or more groups selected from a halogen atom, a $(C_1-C_6)$alkyl group, and oxo(=O).

The compounds of the present invention can be selected particularly from compounds 1 to 44, particularly compounds 1 to 36, described in the examples below, and the pharmaceutically acceptable salts and/or solvates thereof.

The present invention also relates to a compound of formula (I) as defined above, for use as a drug, in particular intended for the treatment of cancer.

The present invention also relates to the use of a compound of formula (I) as defined above, for the manufacture of a drug, in particular intended for the treatment of cancer.

The present invention also relates to a method for treating cancer, comprising the administration to a person in need thereof of an effective dose of a compound of formula (I) as defined above.

The cancer can be more particularly in this case colon cancer, breast cancer, kidney cancer, liver cancer, pancreatic cancer, prostate cancer, glioblastoma, lung cancer, neuroblastoma, inflammatory myofibroblastic tumor, lymphoma, leukemia, myelodysplastic syndrome, myelofibrosis, ovarian cancer, cancer of the head and neck.

The present invention also relates to a pharmaceutical composition comprising at least one compound of formula (I) as defined above, and at least one pharmaceutically acceptable excipient.

The pharmaceutical compositions according to the invention can be formulated in particular for oral administration or for administration by injection (in particular intravenously), said compositions being intended for mammals, including humans.

The active ingredient can be administered in unit dosage forms, mixed with standard pharmaceutical excipients, to animals or to human beings.

The suitable oral unit dosage forms include tablets, capsules, powders, granules and oral solutions or suspensions.

When a solid composition is prepared in tablet form, the principal active ingredient is mixed with a pharmaceutical vehicle such as gelatin, starch, lactose, magnesium stearate, talc, gum arabic or analogues. The tablets can be coated with sucrose or other suitable materials or they can be treated so that they have a prolonged or delayed activity and that they continuously release a predetermined quantity of active ingredient.

A capsule preparation is obtained by mixing the active ingredient with a diluent and pouring the mixture obtained into soft or hard capsules.

A preparation in syrup or elixir form can contain the active ingredient together with a sweetener, an antiseptic, as well as a flavor enhancer and a suitable dye.

The water-dispersible powders or granules can contain the active ingredient mixed with dispersants or wetting agents, or suspending agents, as well as with flavor enhancers or sweeteners.

For administration by injection, one uses aqueous suspensions, isotonic saline solutions or sterile solutions for injection that contain pharmacologically compatible dispersants and/or wetting agents.

The active ingredient can be also formulated in microcapsule form, optionally with one or more additive excipients.

The compounds of the invention as active ingredients can be used at doses between 0.01 mg and 1000 mg per day, given in a single dose once per day or administered in several doses throughout the day, for example twice a day in equal doses. The dose administered per day is advantageously between 5 mg and 500 mg, even more advantageously between 10 mg and 200 mg. It may be necessary to use doses outside these ranges, which would be obvious to the person skilled in the art.

The pharmaceutical compositions according to the invention can further comprise at least one other active ingredient, such as an anti-cancer agent.

The present invention also relates to a pharmaceutical composition comprising:
 (i) at least one compound of formula (I) as defined above, and
 (ii) at least one other active ingredient, such as an anti-cancer agent,
as a combination product for simultaneous, separate or sequential use.

The present invention also relates to a pharmaceutical composition as defined above for use as a drug, particularly intended for the treatment of cancer.

The present invention also relates to a method for treating cancer, comprising the administration to a person in need thereof of an effective dose of a pharmaceutical composition as defined above.

The present invention also relates to the methods for preparing the compounds of formula (I) according to the invention.

The present invention thus relates to a first method for preparing a compound of formula (I) comprising the coupling reaction between:

a compound of the following formula (II):

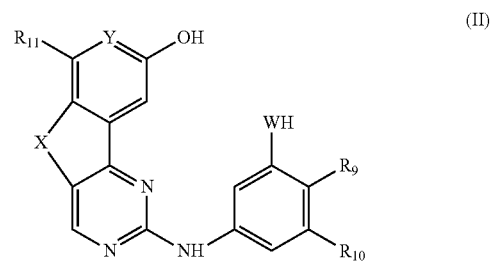

wherein W, X, Y, $R_9$, $R_{10}$ and $R_{11}$ are as defined above, and a compound of the following formula (III):

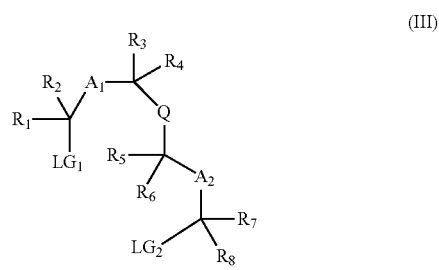

wherein Q, $A_1$, $A_2$ and $R_1$ to $R_8$ are as defined above and $LG_1$ and $LG_2$ each represent, independently of each other, a leaving group.

By "leaving group" is meant, in the meaning of the present invention, a chemical group that can be easily displaced by a nucleophile during a nucleophilic substitution reaction, the nucleophile being in the present case an alcohol or a thiol. Such a leaving group can be more particularly a halogen atom such as a chlorine or bromine atom or a sulfonate. The sulfonate can be in particular an —$OSO_2$—$R_{51}$ group wherein $R_{51}$ represents a ($C_1$-$C_6$)alkyl, aryl, aryl-($C_1$-$C_6$)alkyl or ($C_1$-$C_6$)alkyl-aryl group, said group being optionally substituted by one or more halogen atoms such as fluorine atoms. The sulfonate can be in particular a mesylate (—$OS(O_2)$—$CH_3$), a triflate (—$OS(O)_2$—$CF_3$) or a tosylate (—$OS(O)_2$-(p-Me-$C_6H_4$)).

Groups $LG_1$ and $LG_2$ will represent more particularly a halogen atom such as a bromine.

The coupling (or macrocyclization) reaction will be carried out advantageously in the presence of a base such as potassium carbonate or sodium carbonate. Dimethylformamide can be used as the reaction solvent.

Such a method is illustrated in greater detail in the following Scheme 1.

Scheme 1

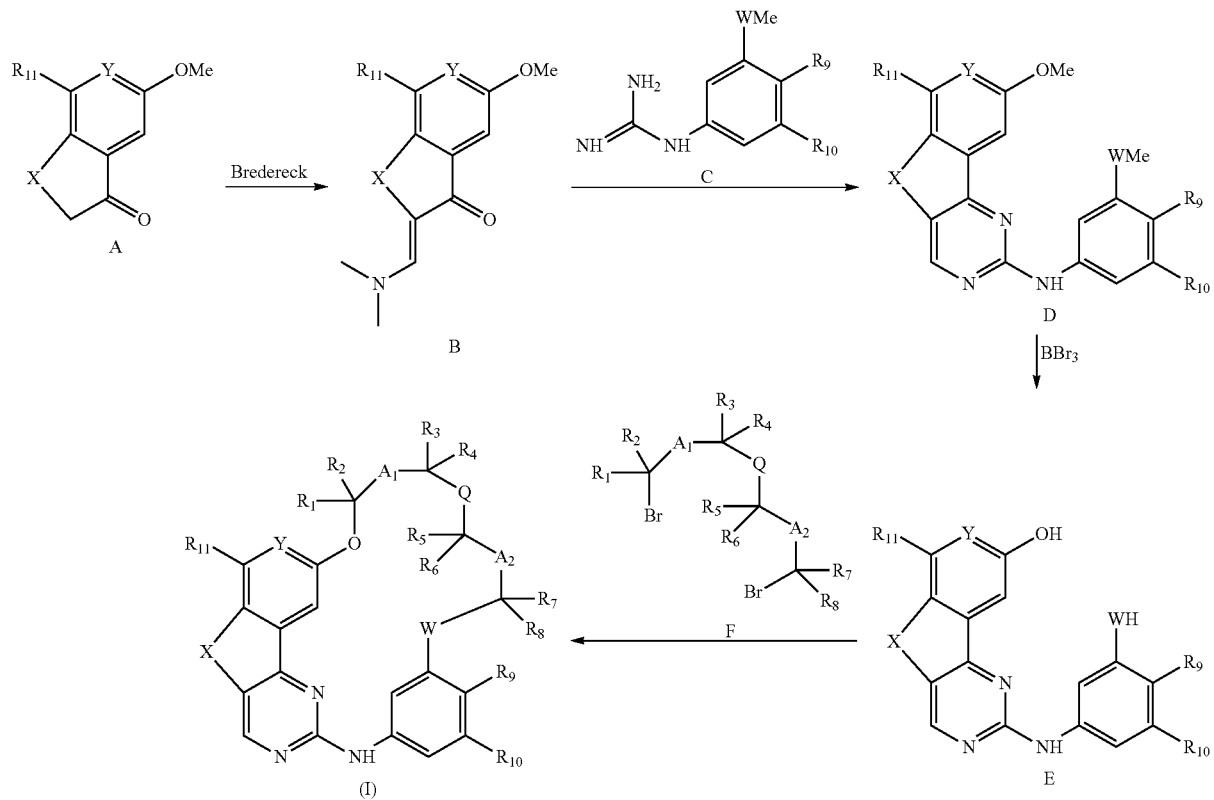

The second step of cyclization between the compound B and the guanidine C according to the following reference (*J. Med. Chem.* 2007, 50, 4516-4527) is typically carried out by heating to a temperature between 20° C. and 200° C. in a polar solvent, such as N—N'-dimethylformamide, and in the presence of an organic base, such as triethylamine or an alcoholate (in particular ($C_1$-$C_6$)alkyl-OM with M=Na, K or Li), or an inorganic base, such as sodium carbonate, potassium carbonate or cesium carbonate or a potassium acetate, or without solvent in a microwave reactor to afford the compound of formula D.

The intermediate of general formula D is transformed into the intermediate of general formula E by a demethylation reaction in the presence of $BBr_3$ in an anhydrous solvent such as dichloromethane at a temperature between −78° C. and 100° C. according to the reference (*J. Med. Chem.* 2008, 51, 4804-4822). The intermediate of general formula E is transformed into the product of general formula (I) by a macrocyclization reaction with the compound F.

The present invention also relates to a second method for preparing a compound of formula (I) wherein $R_9$ and/or $R_{10}$ represents a optionally substituted ($C_1$-$C_6$)alkoxy, optionally substituted ($C_1$-$C_6$)thioalkoxy or $NR_{14}R_{15}$ group or an optionally substituted heterocycle comprising a heteroatom directly attached to the phenyl ring, comprising the coupling between a compound of the following formula (IVa) or (IVb):

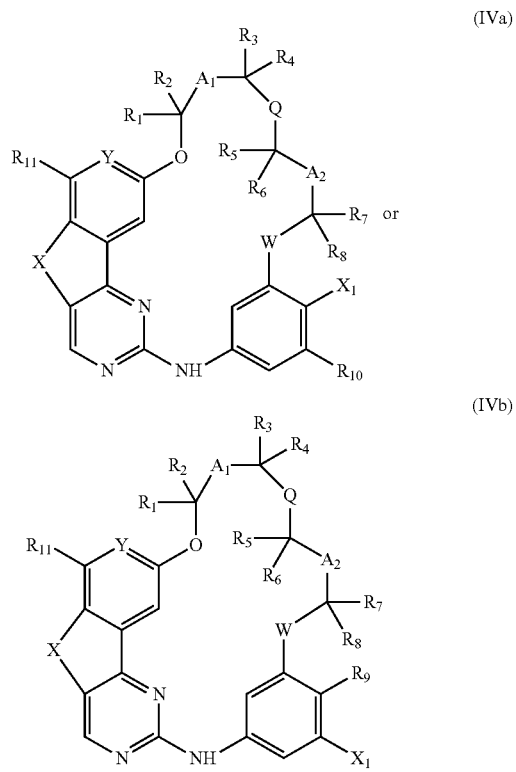

wherein W, X, Y, Q, $A_1$, $A_2$ and $R_1$ to $R_{11}$ are as defined above and $X_1$ represents a halogen atom such as Br, Cl or I, particularly Br, and respectively a compound of formula $R_9H$ or $R_{10}H$ wherein $R_9$ and $R_{10}$ are as defined above.

This reaction can be carried out in the presence of an organic or inorganic base, such as $Et_3N$, $iPr_2NEt$, NaH, pyridine, $Cs_2CO_3$, $Na_2CO_3$ or $K_2CO_3$, optionally in the presence of a salt as catalyst such as KI, $Bu_4NI$, CuI, LiI, $AgBF_4$, $AgClO_4$, $Ag_2CO_3$, KF, $Bu_4NF$ or CsF. The solvent used will be preferably an anhydrous polar solvent such as tetrahydrofuran, dimethylformamide, dimethylsulfoxide, acetone or a mixture thereof. The reaction can advantageously be carried out at a temperature between −20° C. and 140° C. The choice of experimental conditions and of reagents for carrying out this reaction is obvious depending on the nature of the nucleophiles $R_9H$ and $R_{10}H$ and will be carried out according to the methods and techniques well known to the person skilled in the art.

The reaction can also be carried out in a "screw-capped or sealed test tube" heated by thermal energy or microwave energy, particularly at temperatures between 80° C. and 180° C. according to the reference (*J. Org. Chem.* 2009, 74, 5075-5078).

This reaction can also be carried out by catalytic coupling such as described in the reference (*Org. Lett.* 2002, 17, 2885-2888). This reaction is carried out in the presence of a catalytic quantity of a palladium complex such as $(dppf)_2PdCl_2.CH_2Cl_2$. The coupling reaction is carried out advantageously at temperatures between 25° C. and 100° C. The solvent used will be preferably a polar aprotic solvent such as tetrahydrofuran or dioxane.

The present invention also relates to a third method for preparing a compound of formula (I), wherein $R_9$ and/or $R_{10}$ represents an optionally substituted $(C_1-C_6)$alkyl, optionally substituted $(C_2-C_6)$alkenyl or optionally substituted $(C_2-C_6)$alkynyl group, an optionally substituted carbocycle or an optionally substituted heterocycle attached to the phenyl ring by means of a carbon atom, comprising the coupling between a compound of the following formula (Va) or (Vb):

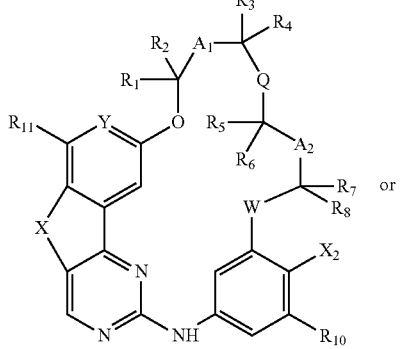

(Va)

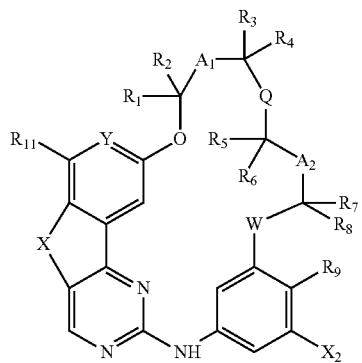

(Vb)

wherein W, X, Y, Q, $A_1$, $A_2$ and $R_1$ to $R_{11}$ are as defined above and $X_2$ represents Br, Cl, I or OTf ($OSO_2CF_3$), and respectively a compound of formula $R_9—BR_{52}R_{53}$ or $R_{10}—BR_{52}R_{53}$ wherein $R_9$ and $R_{10}$ are as defined above and $R_{52}$ and $R_{53}$ represent, independently of each other, an OH, $(C_1-C_6)$alkyl or $(C_1-C_6)$alkoxy group or $R_{52}$ and $R_{53}$ together form an $—X_3—$ or $—O—X_3—O$-chain wherein $X_3$ represents a divalent hydrocarbon group comprising 2 to 15, particularly 2 to 10, carbon atoms.

The reaction conditions for such a coupling are well known to the person skilled in the art as it is a Suzuki coupling.

This reaction is advantageously carried out in the presence of a palladium-based catalyst, for example palladium acetate, tetrakis(triphenylphosphine)palladium(0) or tris(dibenzylideneacetone)dipalladium(0).

An organic or inorganic base can be present, such as an alcoholate (in particular $(C_1-C_6)$alkyl-OM with M=Na, K or Li), NMP (N-methyl-morpholine), $Et_3N$, $iPr_2NEt$, $K_3PO_4$, NaH, $Cs_2CO_3$, $Na_2CO_3$ or $K_2CO_3$.

A polar solvent can be used such as tetrahydrofuran, dimethylformamide, acetonitrile, acetone, methylethylketone, ethanol, dimethyl ether, dioxane, water or a mixture thereof. The reaction can be advantageously carried out at a temperature between 20° C. and 140° C.

The $—BR_{52}R_{53}$ group can be for example a $—B(OH)_2$, $—B((C_1-C_6)alkyl)_2$, $—B(O(C_1-C_6)alkyl)_2$ (e.g. $—B(OiPr)_2$),

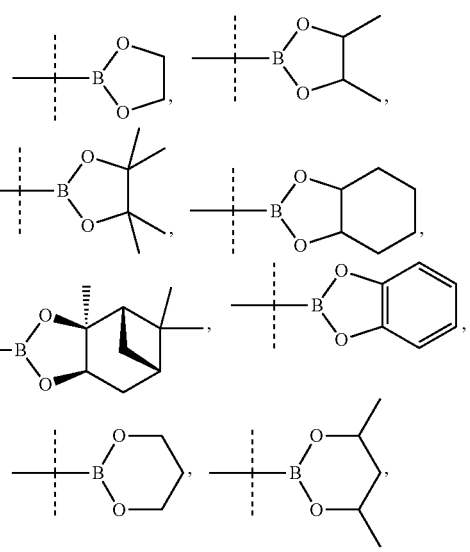

-continued

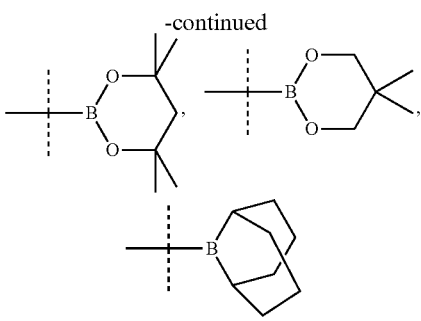

group, etc.

Finally, the present invention relates to a fourth method for preparing a compound of formula (I) wherein $R_9$ and/or $R_{10}$ represents —Z—$(CH_2)_m$—$R_{49}$ wherein Z represents $CH_2$—$CH_2$, CH=CH or C≡C, comprising the following steps:

(1) Sonogashira coupling between a compound of formula (Va) or (Vb) as defined above
and a compound of formula HC≡C—$(CH_2)_m$—$R_{49}$ wherein m and $R_{49}$ are as defined above,
to give a compound of formula (I) wherein $R_9$ or $R_{10}$ represents —C≡C—$(CH_2)_m$—$R_{49}$, and (2) optionally reduction of the alkyne function of the compound of formula (I) obtained in the preceding step to give a compound of formula (I) wherein $R_9$ or $R_{10}$ represents —CH=CH—$(CH_2)_m$—$R_{49}$ or —$(CH_2)_{m+2}$—$R_{49}$.

Step (1):

Sonogashira coupling is a reaction well known to the person skilled in the art who will be able to determine the reaction conditions thereof. It is described particularly in the article by Sonogashira et al. in *Tetrahedron Lett.* 1975, 16, 4467-4470.

This coupling involves a reaction between an acetylene derivative and a halide or an aryl triflate catalyzed by complexes of palladium and copper.

Such a reaction is typically carried out under inert atmosphere, in the presence of a catalytic quantity of a palladium complex (for example $PdCl_2(PPh_3)_2$ or $Pd(PPh_3)_4$), a catalytic quantity of a copper salt (for example CuI), and a base which can be organic, such as triethylamine or DIPEA (diisopropylethylamine), or inorganic, such as sodium carbonate, potassium carbonate or cesium carbonate. The operational conditions generally include reaction temperatures between 20° C. and 45° C., particularly in solvents including dimethylformamide, tetrahydrofuran, dioxane or diethyl ether or a mixture thereof.

Step (2):

The reduction reaction of the triple bond of the alkyne function C≡C to give a double bond CH=CH or a single bond $CH_2$—$CH_2$ is well known to the person skilled in the art who will be able to determine the reaction conditions thereof.

This reduction can be carried out for example by hydrogen in the presence of a catalyst, for example of the palladium on carbon type, particularly in a common ethanol-type solvent, to obtain a single bond $CH_2$—$CH_2$.

The four general methods described above can be supplemented, as need be, by any standard operations described in the literature, known to the person skilled in the art or exemplified in the experimental section, particularly by additional functionalization and/or protection/deprotection reactions.

One or more additional steps of salification and/or of solvation can be carried out at the end of these three methods in order to obtain a pharmaceutically acceptable salt and/or solvate of the compound of formula (I).

The salification step can be carried out under conditions well known to the person skilled in the art, in the presence of a pharmaceutically acceptable acid or base.

When the compound of formula (I) is in solvate form, this solvation has generally taken place in the final step of the method, the solvent of the solvate form being in this case the reaction medium solvent.

The compound of formula (I) obtained by one of these four methods mentioned above can be separated from the reaction medium by methods well known to the person skilled in the art, such as for example by extraction, solvent evaporation or by precipitation and filtration.

The compound of formula (I) can be further purified if necessary by techniques well known to the person skilled in the art, such as by recrystallization if the compound is crystalline, by distillation, by column chromatography on silica gel or by high-performance liquid chromatography (HPLC).

The invention is illustrated by the following non-limiting examples.

EXAMPLES

1. Synthesis of the compounds according to the invention
The following abbreviations were used:
DMSO: Dimethylsulfoxide
HPLC: High-performance liquid chromatography
EI: Electron impact
LAH: Lithium and aluminum hydride ($LiAlH_4$)
LCMS: Liquid chromatography coupled to mass spectrometry
NMR: Nuclear magnetic resonance
1.1. Synthesis of the Intermediates Intermediate 1

1-(4-bromo-3-methoxyphenyl)guanidine

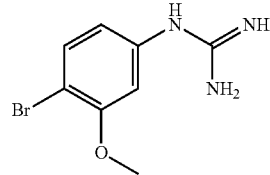

In a 50 mL round-bottom flask are mixed 1 g (4.95 mmol) of 4-bromo-3-methoxyaniline and 3.57 mL of hydrochloric acid. In small portions, 2.91 g (69.3 mmol) of cyanamide is then added. The reaction mixture is heated to 60° C. for 2 hours. After returning to room temperature, the reaction is hydrolyzed by addition of water, basified and extracted with ethyl acetate. The organic phase is dried over sodium sulfate, filtered and concentrated to afford 1.1 g (93%) of 1-(4-bromo-3-methoxyphenyl)guanidine as a yellow solid.

LCMS (EI, m/z): (M+1) 245.08

$^1$H NMR: dH ppm (400 MHz, DMSO): 6.54 (4H, s, NH), 7.27-7.29 (1H, d, $CH_{arom}$), 6.51 (1H, s, $CH_{arom}$), 6.31-6.33 (1H, d, $CH_{arom}$), 3.77 (3H, s, $CH_3$).

Intermediate 2

N,N'-Bis(tert-butoxycarbonyl)-N"-(3-methoxyphenyl) guanidine

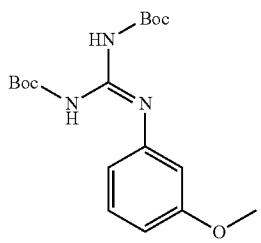 [SMILES: COc1cccc(N=C(NC(=O)OC(C)(C)C)NC(=O)OC(C)(C)C)c1]

To 0.77 g (6.26 mmol) of 3-methoxyaniline in 18 mL of N,N-dimethylformamide are added 2 g (6.89 mmol) of 1,3-bis(tert-butoxycarbonyl)-2-methyl-2-thiopseudourea, 1.915 mL (13.78 mmol) of triethylamine then 1.7 g (6.26 mmol) of mercuric chloride at 0° C. The reaction mixture is stirred at 0° C. for 5 hours then filtered on Celite®. The filtrate is washed with water and extracted with ethyl acetate. The organic phase is dried over sodium sulfate, filtered and concentrated. The residue obtained is purified by chromatography on silica gel (eluent: ethyl acetate/cyclohexane: 50:50 to 100% ethyl acetate) to afford 2.25 g (98%) of N,N'-bis(tert-butoxycarbonyl)-N"-(3-methoxyphenyl) guanidine as a white solid.

LCMS (EI, m/z): (M+1) 366.42

$^1$H NMR: dH ppm (400 MHz, DMSO): 11.37 (1H, s, NH), 9.98 (1H, s, NH), 7.25-7.27 (2H, m, $CH_{arom}$), 7.09-7.11 (1H, m, $CH_{arom}$), 6.72-6.74 (1H, m, $CH_{arom}$), 3.74 (3H, s, $CH_3$), 1.50 (9H, s, $CH_3$), 1.40 (9H, s, $CH_3$).

Intermediate 3

1-(3-methoxyphenyl)guanidine

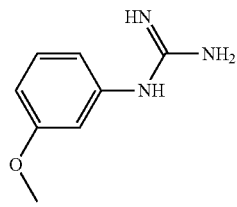

To 2.45 g (6.70 mmol) of N,N'-bis(tert-butoxycarbonyl)-N"-(3-methoxyphenyl)guanidine in 16 mL of dichloromethane is added at 0° C. 16.53 mL (215 mmol) of trifluoroacetic acid. The reaction mixture is stirred at 25° C. for 24 hours then concentrated to afford 1.3 g of 1-(3-methoxyphenyl) guanidine which is used as such, without purification, in the following step.

LCMS (EI, m/z): (M+1) 166.19

Intermediate 4

(E)-2-((dimethylamino)methylene)-7-methoxy-3,4-dihydro naphthalen-1(2H)-one

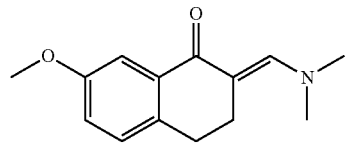

To 7 g (39.7 mmol) of 7-methoxy-3,4-dihydronaphthalen-1(2H)-one is added 79 mL of N,N-dimethylformamide dimethyl acetal (596 mmol). The reaction mixture is refluxed for 15 hours. After evaporation of the solvent under reduced pressure, the residue is purified by chromatography on silica gel (eluent: dichloromethane/AcOEt: 80:20 to 100% AcOEt) to deliver 5.90 g (64%) of (E)-2-((dimethylamino)methylene)-7-methoxy-3,4-dihydronaphthalen-1(2H)-one as a yellow solid.

LCMS (EI, m/z): (M+1) 232.29

$^1$H NMR: dH ppm (400 MHz, DMSO): 7.55 (1H, s, $CH_{arom}$), 7.30-7.31 (1H, d, $CH_{arom}$), 7.14-7.16 (1H, m, $CH_{arom}$), 6.95-6.98 (1H, m, $CH_{arom}$), 3.75 (3H, s, $CH_3$), 3.10 (6H, s, $CH_3$), 2.82-2.85 (2H, t, $CH_2$), 2.67-2.71 (2H, t, $CH_2$).

Intermediate 5

9-methoxy-N-(3-methoxyphenyl)-5,6-dihydrobenzo[h]quinazolin-2-amine

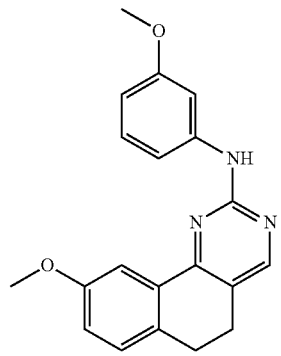 [SMILES: COc1cccc(Nc2ncc3c(n2)-c2cc(OC)ccc2CC3)c1]

To 0.578 g (2.5 mmol) of (E)-2-((dimethylamino)methylene)-7-methoxy-3,4-dihydronaphthalen-1(2H)-one and 0.496 g (3.00 mmol) of 2-(3-methoxyphenyl)guanidine in 25 mL of ethanol is added 1.037 g (7.50 mmol) of potassium carbonate. The reaction mixture is refluxed for 15 hours. After returning to room temperature, the solvent is evaporated and the solid formed is filtered, rinsed with methanol to afford 0.56 g (67%) of 9-methoxy-N-(3-methoxyphenyl)-5,6-dihydrobenzo[h]quinazolin-2-amine as a yellow powder.

LCMS (EI, m/z): (M+1) 334.38

$^1$H NMR: dH ppm (400 MHz, DMSO): 9.54 (1H, s, NH), 8.46 (1H, s, $CH_{arom}$), 7.78-7.79 (1H, d, $CH_{arom}$), 7.70 (1H, s, $CH_{arom}$), 7.14-7.28 (3H, m, $CH_{arom}$), 7.02-7.05 (1H, m, $CH_{arom}$), 6.51-6.54 (1H, m, $CH_{arom}$), 3.84 (3H, s, $CH_3$), 3.76 (3H, s, $CH_3$), 2.78-2.86 (4H, m, $CH_2$).

Intermediate 6

N-(4-bromo-3-methoxyphenyl)-9-methoxy-5,6-dihydrobenzo[h]quinazolin-2-amine

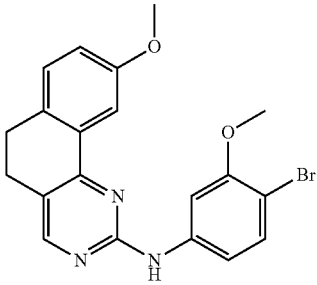 [SMILES: COc1ccc2c(c1)-c1nc(Nc3ccc(Br)c(OC)c3)ncc1CC2]

To 14.19 g (58.1 mmol) of 1-(4-bromo-3-methoxyphenyl) guanidine in ethanol (120 mL) is added 10.34 g (44.7 mmol) of (E)-2-((dimethylamino)methylene)-7-methoxy-3,4-dihydronaphthalen-1(2H)-one. The reaction mixture is refluxed for 36 hours. After returning to room temperature, the solvent is evaporated and the solid formed is filtered, rinsed with methanol to afford 12.90 g (70%) of N-(4-bromo-3-methoxyphenyl)-9-methoxy-5,6-dihydrobenzo[h]quinazolin-2-amine as a yellow powder.

LCMS (EI, m/z): (M+1) 413.28

$^1$H NMR: dH ppm (400 MHz, DMSO): 9.71 (1H, s, NH), 8.43 (1H, s, CH$_{arom}$), 7.82-7.83 (1H, d, CH$_{arom}$), 7.76-7.77 (1H, d, CH$_{arom}$), 7.44-7.46 (1H, d, CH$_{arom}$), 7.38-7.41 (1H, dd, CH$_{arom}$), 7.27-7.30 (1H, d, CH$_{arom}$), 7.04-7.06 (1H, dd, CH$_{arom}$), 3.87 (3H, m, CH3), 3.82 (3H, m, CH3), 2.77-2.87 (4H, m, CH$_2$).

Intermediate 7

2-((3-hydroxyphenyl)amino)-5,6-dihydrobenzo[h]quinazolin-9-ol

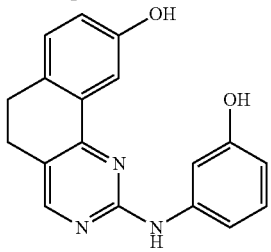 [SMILES: Oc1cccc(Nc2ncc3c(n2)-c2cc(O)ccc2CC3)c1]

To a solution of 300 mg (0.9 mmol) of 9-methoxy-N-(3-methoxyphenyl)-5,6-dihydrobenzo[h]quinazolin-2-amine in 10 mL of dichloromethane is added 0.45 mL of tribromoborane at −78° C. The reaction mixture is then stirred at 45° C. for 5 hours then overnight at room temperature. 2 mL of methanol is added to the reaction mixture at 0° C. which is then heated to 35° C. for 25 minutes. The solid formed is filtered then washed twice with 20 mL of ether to afford 130 mg (47%) of 2-((4-bromo-3-hydroxyphenyl)amino)-5,6-dihydrobenzo[h]quinazolin-9-ol as a yellow powder.

LCMS (EI, m/z): (M+1) 306.33

$^1$H NMR: dH ppm (400 MHz, DMSO): 9.51 (1H, s, NH), 8.35 (1H, s, CH$_{arom}$), 7.63-7.64 (1H, d, CH$_{arom}$), 7.29-7.31 (1H, d, CH$_{arom}$), 7.23-7.24 (1H, d, CH$_{arom}$), 7.14-7.16 (1H, d, CH$_{arom}$), 7.07-7.11 (1H, m, CH$_{arom}$), 6.86-6.89 (1H, d, CH$_{arom}$), 6.39-6.42 (1H, d, CH$_{arom}$), 2.76-2.78 (4H, m, CH$_2$).

Intermediate 8

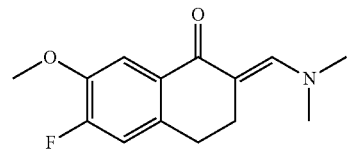

Intermediate 8 was prepared according to the protocol described for the preparation of intermediate 4 starting with 500 mg of 6-fluoro-7-methoxy-3,4-dihydronaphthalen-1(2H)-one and 2.394 mL of N,N-dimethylformamide dimethyl acetal to afford 600 mg (93%) of intermediate 8.

LCMS (EI, m/z): (M+1) 250.28

$^1$H NMR: dH ppm (400 MHz, DMSO): 7.55 (1H, s, CH$_{arom}$), 7.49-7.51 (1H, d, CH$_{arom}$), 7.10-7.13 (1H, d, CH$_{arom}$), 3.84 (3H, s, CH$_3$), 3.10 (6H, s, CH$_3$), 2.84-2.87 (2H, t, CH$_2$), 2.65-2.71 (2H, t, CH$_2$).

Intermediate 9

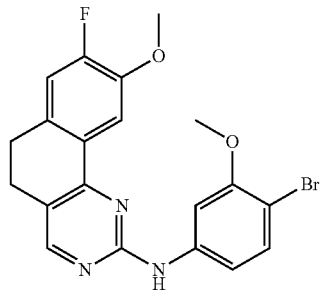 [SMILES: COc1cc2c(cc1F)CCc1cnc(Nc3ccc(Br)c(OC)c3)nc1-2]

Intermediate 9 was prepared according to the protocol described for the preparation of intermediate 5 starting with 600 mg of intermediate 8 and 0.76 g of 1-(4-bromo-3-methoxyphenyl)guanidine to afford 550 mg (53%) of intermediate 9.

LCMS (EI, m/z): (M+1) 431.27

$^1$H NMR: dH ppm (400 MHz, DMSO): 9.70 (1H, s, NH), 8.42 (1H, s, CH$_{arom}$), 7.89-7.92 (1H, d, CH$_{arom}$), 7.66 (1H, s, CH$_{arom}$), 7.45-7.52 (2H, m, CH$_{arom}$), 7.26-7.29 (1H, d, CH$_{arom}$), 3.93 (3H, m, CH$_3$), 3.94 (3H, m, CH$_3$), 2.79-2.85 (4H, m, CH$_2$).

Intermediate 10

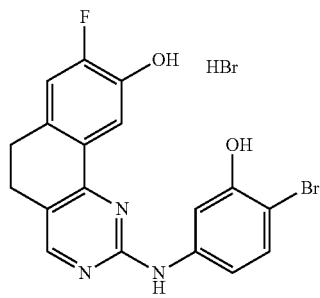 [SMILES: Oc1cc2c(cc1F)CCc1cnc(Nc3ccc(Br)c(O)c3)nc1-2 ; Br]

Intermediate 10 was prepared according to the protocol described for the preparation of intermediate 7 starting with 550 mg of intermediate 9 to afford 600 mg (97%) of intermediate 10.

LCMS (EI, m/z): (M+1) 403.21

$^1$H NMR: dH ppm (400 MHz, DMSO): 9.64 (1H, s, NH), 8.23 (1H, s, CH$_{arom}$), 7.81-7.84 (1H, d, CH$_{arom}$), 7.42-7.43 (1H, d, CH$_{arom}$), 7.33-7.41 (2H, m, CH$_{arom}$), 7.15-7.18 (1H, d, CH$_{arom}$), 2.76-2.79 (4H, m, CH$_2$).

Intermediate 11

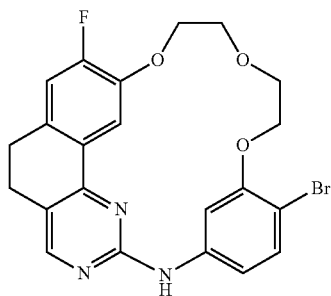 [SMILES: Fc1cc2c3cc1OCCOCCOc1cc(ccc1Br)Nc1ncc(c-3n1)CC2]

Intermediate 11 was prepared according to the protocol described for the preparation of compound 2 starting with 600 mg of intermediate 10 to afford 527 mg of intermediate 11 with a yield of 90%.

LCMS (EI, m/z): (M+1) 473.30

$^1$H NMR: dH ppm (400 MHz, DMSO): 9.81 (1H, s, NH), 8.67 (1H, s, CH$_{arom}$), 8.42 (1H, s, CH$_{arom}$), 8.14-8.17 (1H, d, CH$_{arom}$), 7.41-7.43 (1H, d, CH$_{arom}$), 7.26-7.29 (1H, d, CH$_{arom}$), 6.83-6.85 (1H, d, CH$_{arom}$), 4.26-4.30 (4H, m, CH$_2$), 3.79-3.82 (4H, m, CH$_2$), 2.78-2.82 (4H, m, CH$_2$).

1.2. Synthesis of the Compounds According to the Invention

Compound 1

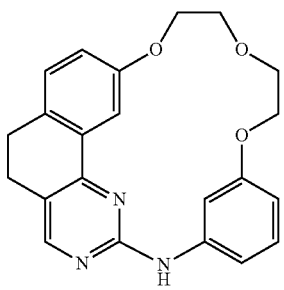 [SMILES: c1cc2cc(c1)OCCOCCOc1ccc3c(c1)-c1nc(ncc1CC3)N2]

To a stirred solution of 0.93 g (2.11 mmol) of 2-((3-hydroxyphenyl)amino)-5,6-dihydrobenzo[h]quinazolin-9-ol in 100 mL of N,N-dimethylformamide is added 135 mg (0.9 mmol) of potassium carbonate then 0.099 g (0.426 mmol) of 1-bromo-2-(2-bromoethoxy)ethane in 10 mL of N,N-dimethylformamide for one hour. The reaction mixture is stirred at 75° C. for 20 hours. After returning to room temperature, the solvent is evaporated, water is added and the solid formed is filtered and dried under vacuum to afford 0.01 g (6%) of compound 1 as a beige powder.

LCMS (EI, m/z): (M+1) 376.42

$^1$H NMR: dH ppm (400 MHz, DMSO): 9.67 (1H, s, NH), 8.71 (1H, s, CH$_{arom}$), 8.42 (1H, s, CH$_{arom}$), 8.07 (1H, s, CH$_{arom}$), 7.24-7.26 (1H, d, CH$_{arom}$), 7.16 (1H, t, CH$_{arom}$), 7.02 (1H, d, CH$_{arom}$), 6.80-6.82 (1H, d, CH$_{arom}$), 6.52 (1H, d, CH$_{arom}$), 4.28 (2H, m, CH$_2$), 4.09 (2H, m, CH$_2$), 3.87-3.92 (4H, m, CH$_2$), 2.67-2.85 (4H, m, CH$_2$).

Compound 2

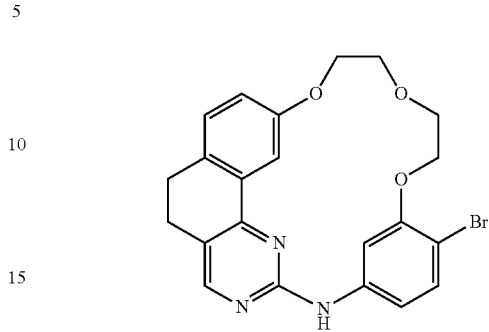

To a stirred solution of 2.615 g (27.2 mmol) of 2-((4-bromo-3-hydroxyphenyl)amino)-5,6-dihydrobenzo[h]quinazolin-9-ol in 362 mL of N,N-dimethylformamide is added 4.7 g (136 mmol) of potassium carbonate then 6.31 g (27.2 mmol) of 1-bromo-2-(2-bromoethoxy)ethane in 123 mL of N,N-dimethylformamide for one hour. The reaction mixture is stirred at 80° C. for 20 hours. After returning to room temperature, the solvent is evaporated, water is added and the solid formed is filtered and dried under vacuum to afford 12.2 g (80%) of compound 2 as a beige powder.

LCMS (EI, m/z): (M+1) 455.31

$^1$H NMR: dH ppm (400 MHz, DMSO): 9.81 (1H, s, NH), 8.71-8.72 (1H, s, CH$_{arom}$), 8.44 (1H, s, CH$_{arom}$), 8.02-8.03 (1H, d, CH$_{arom}$), 7.40-7.43 (1H, d, CH$_{arom}$), 7.26-7.28 (1H, d, CH$_{arom}$), 7.05-7.08 (1H, dd, CH$_{arom}$), 6.88-6.83 (1H, dd, CH$_{arom}$), 4.24-4.27 (4H, m, CH$_2$), 3.75-3.82 (4H, m, CH$_2$), 2.78-2.85 (4H, m, CH$_2$).

Compound 3

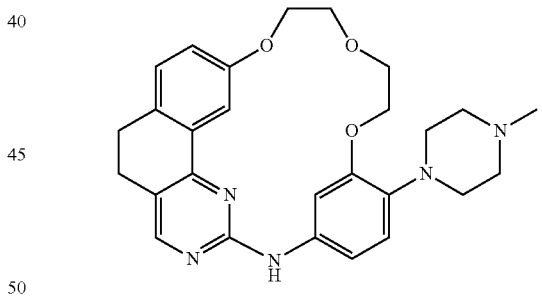

In a 50 mL round-bottom flask are mixed 14 mg (0.029 mmol) of 2-(dicyclohexylphosphino)-2',4',6'-triisopropylbiphenyl, 53 mg (0.058 mmol) of (dppf)$_2$PdCl$_2$.CH$_2$Cl$_2$, 328 mg (0.722 mmol) of compound 2 and 1.01 g (10.11 mmol) of 1-methylpiperazine under argon. 4 mL of tetrahydrofuran and 5.78 mL (5.78 mmol) of lithium bis(trimethylsilyl) amide (LiHMDS) are added at room temperature. The reaction mixture is heated to 80° C. for 1 h 45 min. After returning to room temperature, the reaction is hydrolyzed by slow addition of water at 0° C. and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 35.4 mg (10%) of compound 3 as a yellow solid.

LCMS (EI, m/z): (M+1) 474.56

¹H NMR: dH ppm (400 MHz, DMSO): 9.46 (1H, s, NH), 8.51-8.52 (1H, d, CH$_{arom}$), 8.38 (1H, s, CH$_{arom}$), 8.01-8.02 (1H, d, CH$_{arom}$), 7.25-7.27 (1H, d, CH$_{arom}$), 7.05-7.07 (1H, d, CH$_{arom}$), 6.79-6.85 (2H, m, CH$_{arom}$), 4.23-4.25 (4H, m, CH$_2$), 3.75-3.77 (4H, m, CH$_2$), 2.94 (4H, m, CH$_2$), 2.76-2.86 (4H, m, CH$_2$), 2.45 (4H, m, CH$_2$), 2.21 (3H, s, CH$_3$).

Compound 4

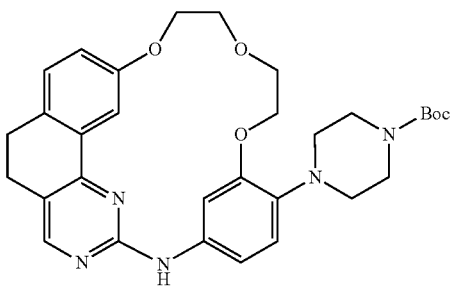 [SMILES: CC(C)(C)OC(=O)N1CCN(c2ccc3cc2OCCOCCOc2ccc4c(c2)-c2nc(ncc2CC4)N3)CC1]

Compound 4 was prepared according to the protocol described for the preparation of compound 3 starting with 0.7 g of compound 2 and 2.29 g of the amine tert-butyl piperazine-1-carboxylate to afford 380 mg (44%) of compound 4.

LCMS (EI, m/z): (M+1) 560.65

¹H NMR: dH ppm (400 MHz, DMSO): 9.48 (1H, s, NH), 8.54-8.55 (1H, d, CH$_{arom}$), 8.39 (1H, s, CH$_{arom}$), 8.02-8.03 (1H, d, CH$_{arom}$), 7.26-7.28 (1H, d, CH$_{arom}$), 7.06-7.08 (1H, dd, CH$_{arom}$), 6.86-6.87 (1H, m, CH$_{arom}$), 6.79-6.82 (1H, dd, CH$_{arom}$), 4.23-4.25 (4H, m, CH$_2$), 3.75-3.81 (4H, m, CH$_2$), 2.46 (4H, m, CH$_2$), 2.77-2.89 (8H, m, CH$_2$), 1.4 (9H, s, CH$_3$).

Compound 5

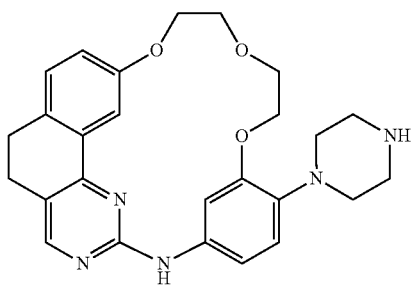 [SMILES: c1cc(N2CCNCC2)c2cc1Nc1ncc3c(n1)-c1cc(ccc1CC3)OCCOCCO2]

To 380 mg (0.679 mmol) of compound 4 is added dropwise 5 mL of a solution of hydrochloric acid in isopropanol (5N). The solution is stirred at 45° C. for 2 h 50 min. The solid formed is filtered then washed twice with 20 mL of water. The solid formed is placed in basic medium and extracted with ethyl acetate. The organic phase is dried over sodium sulfate, filtered and concentrated to afford 168 mg (54%) of compound 5 as a yellow solid.

LCMS (EI, m/z): (M+1) 460.54

¹H NMR: dH ppm (400 MHz, DMSO): 9.45 (1H, s, NH), 8.51-8.52 (1H, d, CH$_{arom}$), 8.38 (1H, s, CH$_{arom}$), 8.02-8.03 (1H, d, CH$_{arom}$), 7.25-7.27 (1H, d, CH$_{arom}$), 7.05-7.08 (1H, dd, CH$_{arom}$), 6.81-6.84 (2H, m, CH$_{arom}$), 4.24 (4H, m, CH$_2$), 3.74-3.78 (4H, m, CH$_2$), 3.76-3.84 (12H, m, CH$_2$).

Compound 6

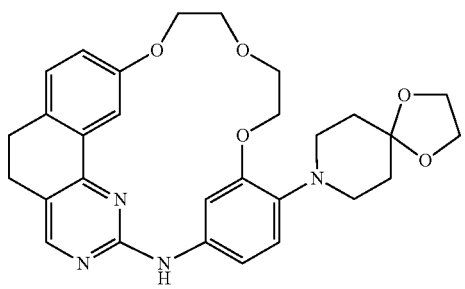 [SMILES: c1cc(N2CCC3(CC2)OCCO3)c2cc1Nc1ncc3c(n1)-c1cc(ccc1CC3)OCCOCCO2]

Compound 6 was prepared according to the protocol described for the preparation of compound 3 starting with 1 g of compound 2 and 1.26 g of the amine 1,4-dioxa-8-azaspiro[4.5]decane to afford 246 mg (22%) of compound 6.

LCMS (EI, m/z): (M+1) 517.58

¹H NMR: dH ppm (400 MHz, DMSO): 9.46 (1H, s, NH), 8.51-8.52 (1H, d, CH$_{arom}$), 8.38 (1H, s, CH$_{arom}$), 8.01-8.02 (1H, d, CH$_{arom}$), 7.25-7.27 (1H, d, CH$_{arom}$), 7.05-7.08 (1H, dd, CH$_{arom}$), 6.80-6.88 (1H, m, CH$_{arom}$), 6.78-6.80 (1H, m, CH$_{arom}$), 4.22-4.26 (4H, m, CH$_2$), 3.90 (4H, s, CH$_2$), 2.74-3.79 (4H, m, CH$_2$), 2.97-3.01 (4H, m, CH$_2$), 2.75-2.85 (4H, m, CH$_2$), 1.73-1.77 (4H, m, CH$_2$).

Compound 7

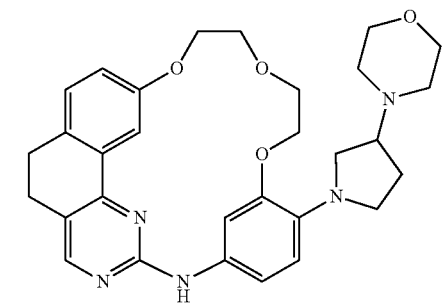 [SMILES: c1cc(N2CCC(N3CCOCC3)C2)c2cc1Nc1ncc3c(n1)-c1cc(ccc1CC3)OCCOCCO2]

Compound 7 was prepared according to the protocol described for the preparation of compound 3 starting with 200 mg of compound 2 and 275 mg of the amine 4-(pyrrolidin-3-yl)morpholine to afford 10 mg (4%) of compound 7.

LCMS (EI, m/z): (M+1) 530.63

¹H NMR: dH ppm (400 MHz, DMSO): 9.45 (1H, s, NH), 8.51 (1H, 5, CH$_{arom}$), 8.38 (1H, s, CH$_{arom}$), 8.01-8.02 (1H, d, CH$_{arom}$), 7.25-7.27 (1H, d, CH$_{arom}$), 7.05-7.07 (1H, dd, CH$_{arom}$), 6.79-6.85 (2H, m, CH$_{arom}$), 4.22-4.25 (4H, m, CH$_2$), 3.78-3.79 (4H, m, CH$_2$), 3.50-3.54 (2H, m, CH$_2$), 2.94 (4H, m, CH$_2$), 2.74-3.86 (4H, m, CH$_2$), 2.43-2.58 (4H, m, CH$_2$), 2.75-2.85 (5H, m, CH$_2$ and CH).

Compound 8

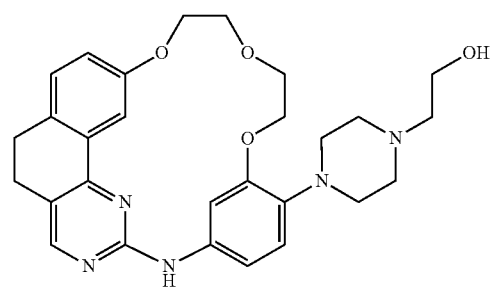 [SMILES: OCCN1CCN(c2ccc3cc2OCCOCCOc2ccc4c(c2)-c2nc(ncc2CC4)N3)CC1]

Compound 8 was prepared according to the protocol described for the preparation of compound 3 starting with 200 mg of compound 2 and 229 mg of the amine 2-(piperazin-1-yl)ethanol to afford 27 mg (11%) of compound 8.

LCMS (EI, m/z): (M+1) 504.59

$^1$H NMR: dH ppm (400 MHz, DMSO): 9.35 (1H, s, NH), 8.45-8.47 (1H, d, CH$_{arom}$), 8.38 (1H, s, CH$_{arom}$), 8.01-8.02 (1H, d, CH$_{arom}$), 7.25-7.27 (1H, d, CH$_{arom}$), 7.04-7.07 (1H, dd, CH$_{arom}$), 6.75-6.77 (1H, dd, CH$_{arom}$), 6.65-6.67 (1H, dd, CH$_{arom}$), 4.02-4.25 (4H, m, CH$_2$), 3.74-3.79 (4H, m, CH$_2$), 3.58-3.61 (4H, m, CH$_2$), 3.10-3.25 (3H, m, CH$_2$), 2.73-2.86 (6H, m, CH$_2$), 2.52 (4H, m, CH$_2$).

Compound 9

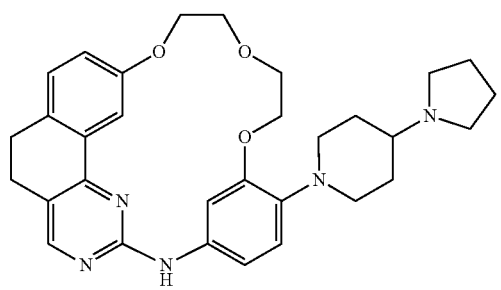 [SMILES: c1cc(N2CCC(N3CCCC3)CC2)c2cc1Nc1ncc3c(n1)-c1cc(ccc1CC3)OCCOCCO2]

Compound 9 was prepared according to the protocol described for the preparation of compound 3 starting with 200 mg of compound 2 and 272 mg of the amine 4-(pyrrolidin-1-yl)piperidine to afford 7.3 mg (3%) of compound 9.

LCMS (EI, m/z): (M+1) 528.66

$^1$H NMR: dH ppm (400 MHz, DMSO): 9.44 (1H, s, NH), 8.52-8.51 (1H, d, CH$_{arom}$), 8.37 (1H, s, CH$_{arom}$), 8.01-8.02 (1H, d, CH$_{arom}$), 7.25-7.27 (1H, d, CH$_{arom}$), 7.05-7.07 (1H, dd, CH$_{arom}$), 6.80-6.86 (2H, m, CH$_{arom}$), 4.22-4.25 (4H, m, CH$_2$), 3.76-3.77 (4H, m, CH$_2$), 2.74-2.86 (4H, m, CH$_2$), 2.46-2.56 (7H, m, CH$_2$), 2.02 (1H, m, CH), 1.89-1.90 (2H, m, CH$_2$), 1.47-1.57 (2H, m, CH$_2$), 1.68 (4H, m, CH$_2$).

Compound 10

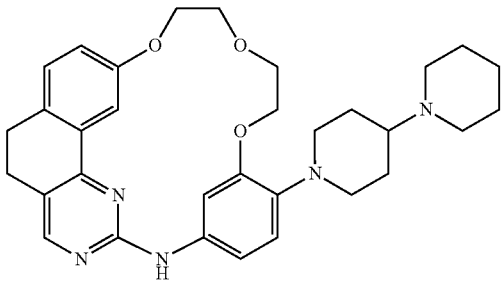 [SMILES: c1cc(N2CCC(N3CCCCC3)CC2)c2cc1Nc1ncc3c(n1)-c1cc(ccc1CC3)OCCOCCO2]

Compound 10 was prepared according to the protocol described for the preparation of compound 3 starting with 200 mg of compound 2 and 296 mg of the amine 1,4'-bipiperidine to afford 23 mg (9%) of compound 10.

LCMS (EI, m/z): (M+1) 542.68

$^1$H NMR: dH ppm (400 MHz, DMSO): 9.44 (1H, s, NH), 8.50-8.51 (1H, d, CH$_{arom}$), 8.37 (1H, s, CH$_{arom}$), 8.01-8.02 (1H, d, CH$_{arom}$), 7.25-7.27 (1H, d, CH$_{arom}$), 7.05-7.07 (1H, dd, CH$_{arom}$), 6.82-6.84 (1H, d, CH$_{arom}$), 6.77-6.79 (1H, dd, CH$_{arom}$), 4.22-4.25 (4H, m, CH$_2$), 3.75-3.79 (4H, m, CH$_2$), 3.35-3.39 (2H, m, CH$_2$), 2.75-2.86 (4H, m, CH$_2$), 2.46-2.56 (6H, m, CH$_2$), 2.27 (1H, m, CH), 1.75-1.80 (2H, m, CH$_2$), 1.35-1.62 (8H, m, CH$_2$).

Compound 11

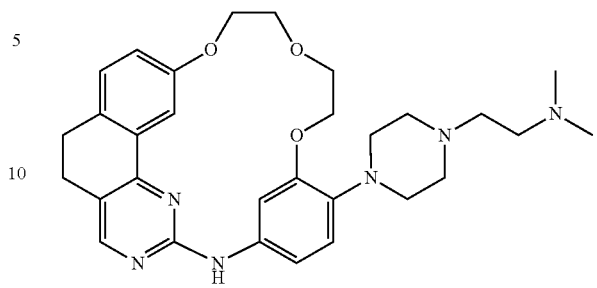

Compound 11 was prepared according to the protocol described for the preparation of compound 3 starting with 200 mg of compound 2 and 277 mg of N,N-dimethyl-2-(piperazin-1-yl)ethanamine to afford 43 mg (19%) of compound 11.

LCMS (EI, m/z): (M+1) 531.66

$^1$H NMR: dH ppm (400 MHz, DMSO): 9.44 (1H, s, NH), 8.50-8.51 (1H, d, CH$_{arom}$), 8.37 (1H, s, CH$_{arom}$), 8.01-8.02 (1H, d, CH$_{arom}$), 7.25-7.27 (1H, d, CH$_{arom}$), 7.05-7.07 (1H, dd, CH$_{arom}$), 6.82-6.84 (1H, d, CH$_{arom}$), 6.77-6.79 (1H, dd, CH$_{arom}$), 4.22-4.25 (4H, m, CH$_2$), 3.75-3.79 (4H, m, CH$_2$), 2.93 (4H, m, CH$_2$), 2.75-2.86 (4H, m, CH$_2$), 2.31-2.47 (8H, m, CH), 2.14 (6H, m, CH$_3$).

Compound 12

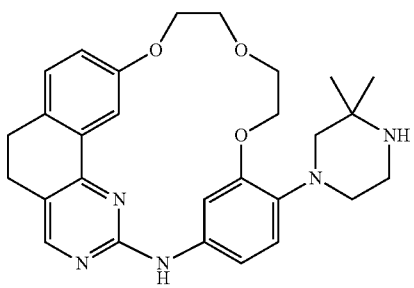 [SMILES: CC1(C)CN(c2ccc3cc2OCCOCCOc2ccc4c(c2)-c2nc(ncc2CC4)N3)CCN1]

To 100 mg (0.17 mmol) of compound 36 is added dropwise 5 mL of a solution of hydrochloric acid (5N) in isopropanol. The solution is stirred at 45° C. for 2 hours. The solid formed is filtered then washed twice with 20 mL of water. The solid formed is placed in basic medium and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 26 mg (31%) of compound 12 as a yellow solid.

LCMS (EI, m/z): (M+1) 488.59

$^1$H NMR: dH ppm (400 MHz, DMSO): 9.45 (1H, s, NH), 8.52 (1H, s, CH$_{arom}$), 8.38 (1H, d, CH$_{arom}$), 8.02-8.03 (1H, d, CH$_{arom}$), 7.26-7.28 (1H, d, CH$_{arom}$), 7.05-7.08 (1H, dd, CH$_{arom}$), 6.80 (2H, s, CH$_{arom}$), 4.22-4.25 (4H, m, CH$_2$), 3.75-3.79 (4H, m, CH$_2$), 2.85-2.87 (4H, m, CH$_2$), 2.76-2.78 (4H, m, CH$_2$), 2.60 (2H, m, CH), 1.12 (6H, s, CH$_3$).

Compound 13

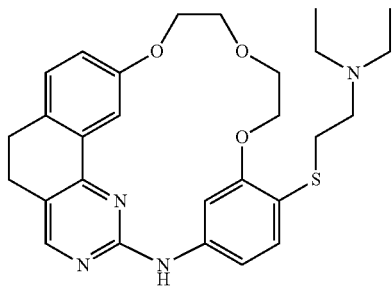 [SMILES: CCN(CC)CCSc1ccc2cc1OCCOCCOc1ccc3c(c1)-c1nc(ncc1CC3)N2]

In a microwave reactor are mixed 200 mg (0.44 mmol) of compound 2, 84 mg (0.44 mmol) of cuprous iodide and 112 mg (0.660 mmol) of (diethylamino)ethanethiol, HCl. The reaction mixture is heated to 200° C. for 45 minutes. After returning to room temperature, water is added and the solid formed is filtered and purified by chromatography on silica gel (eluent: ethyl acetate/methanol/ammonia: 94:4:2) to afford 72 mg (29%) of compound 13 as a yellow solid LCMS (EI, m/z): (M+1) 507.66

$^1$H NMR: dH ppm (400 MHz, DMSO): 9.70 (1H, s, NH), 8.60-8.61 (1H, d, $CH_{arom}$), 8.43 (1H, s, $CH_{arom}$), 8.02-8.03 (1H, d, $CH_{arom}$), 7.26-7.28 (1H, d, $CH_{arom}$), 7.20-7.22 (1H, d, $CH_{arom}$), 7.05-7.06 (1H, dd, $CH_{arom}$), 6.82-6.85 (1H, dd, $CH_{arom}$), 4.23-4.26 (4H, m, $CH_2$), 3.74-3.83 (4H, m, $CH_2$), 2.75-2.88 (6H, m, $CH_2$), 2.45-2.60 (6H, m, $CH_2$), 0.81-0.93 (6H, t, $CH_3$).

Compound 14

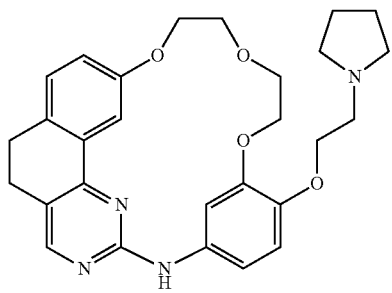 [SMILES: c1cc(OCCN2CCCC2)c2cc1Nc1ncc3c(n1)-c1cc(ccc1CC3)OCCOCCO2]

In a microwave reactor are mixed 200 mg (0.44 mmol) of compound 2, 84 mg (0.44 mmol) of cuprous iodide and 0.515 mL of (hydroxyethyl)pyrrolidine (4.44 mmol). The reaction mixture is heated to 200° C. for 45 minutes. After returning to room temperature, water is added and the solid formed is filtered and purified by chromatography on silica gel (eluent: ethyl acetate/methanol/ammonia: 94:4:2) to afford 16.6 mg (7.5%) of compound 14 as a yellow solid.

LCMS (EI, m/z): (M+1) 489.58

$^1$H NMR: dH ppm (400 MHz, DMSO): 9.47 (1H, s, NH), 8.54 (1H, s, $CH_{arom}$), 8.38 (1H, s, $CH_{arom}$), 8.02 (1H, d, $CH_{arom}$), 7.25-7.27 (1H, d, $CH_{arom}$), 7.04-7.06 (1H, dd, $CH_{arom}$), 6.93-6.95 (1H, d, $CH_{arom}$), 6.80-6.82 (1H, dd, $CH_{arom}$), 4.20-4.26 (4H, m, $CH_2$), 3.73-3.78 (4H, m, $CH_2$), 2.74-2.86 (6H, m, $CH_2$), 2.45-2.58 (6H, m, $CH_2$), 1.69 (4H, m, $CH_3$).

Compound 15

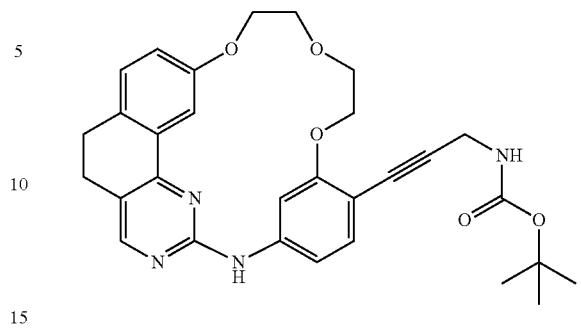

In a 50 mL vial are mixed 2.5 g (5.50 mmol) of compound 2, 0.603 g (1.266 mmol) of 2-(dicyclohexylphosphino)-2',4',6'-triisopropylbiphenyl, 106 mg (0.275 mmol) of bis(benzonitrile)palladium(II) chloride, 1.53 g (9.90 mmol) of tert-butyl prop-2-yn-1-yl-carbamate and 5.38 g (16.51 mmol) of cesium carbonate in 23 mL of N,N-dimethylformamide at room temperature. 2.19 g (6.6 mmol) of tetrabutylammonium bromide is added to the reaction mixture. The reaction mixture is heated to 80° C. for 15 hours. After returning to room temperature, the reaction is hydrolyzed by slow addition of water and extracted with ethyl acetate. The organic phase is dried over sodium sulfate, filtered and concentrated. The residue obtained is purified by chromatography on silica gel (eluent: ethyl acetate/cyclohexane: 60:40) to afford 1.3 g (45%) of compound 15 as a yellow solid.

LCMS (EI, m/z): (M+1) 529.59

$^1$H NMR: dH ppm (400 MHz, DMSO): 9.86 (1H, s, NH), 8.62-8.63 (1H, d, $CH_{arom}$), 8.45 (1H, s, $CH_{arom}$), 8.03-8.04 (1H, d, $CH_{arom}$), 7.32 (1H, t, $CH_{arom}$), 7.27-7.29 (1H, d, $CH_{arom}$), 7.20-7.22 (1H, dd, $CH_{arom}$), 7.06-7.08 (1H, dd, $CH_{arom}$), 6.82-6.84 (1H, dd, $CH_{arom}$), 4.24-4.26 (4H, m, $CH_2$), 3.96-3.98 (2H, m, $CH_2$), 3.76-3.82 (4H, m, $CH_2$), 2.77-2.88 (4H, m, $CH_2$), 1.41 (9H, m, $CH_3$).

Compound 16

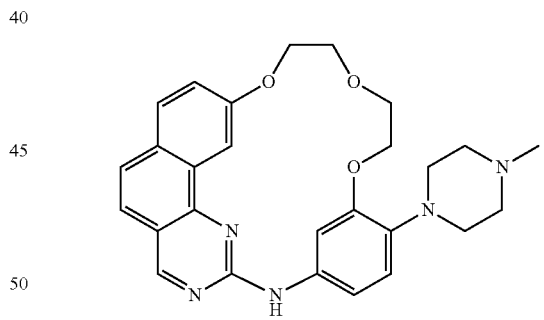

In a 50 mL round-bottom flask are introduced successively 150 mg (0.32 mmol) of compound 3 and 57 mg (0.25 mmol) of 2,3-dichloro-5,6-dicyano-1,4-benzoquinone in 15 mL of chloroform. The reaction mixture is refluxed overnight, the solvent is evaporated and the crude reaction product is purified by preparative HPLC to afford 1.3 mg (0.7%) of compound 16 as a yellow solid.

LCMS (EI, m/z): (M+1) 472.55

$^1$H NMR: dH ppm (400 MHz, DMSO): 9.90 (1H, s, NH), 9.25 (1H, s, $CH_{arom}$), 8.72 (1H, s, $CH_{arom}$), 8.69 ($^1$H, s, $CH_{arom}$), 7.90-7.95 (1H, d, $CH_{arom}$), 7.65-7.70 (2H, m, $CH_{arom}$), 7.40-7.45 (1H, dd, $CH_{arom}$), 6.90-6.95 (2H, m, $CH_{arom}$), 4.40-4.45 (2H, t, $CH_2$), 4.30 (2H, t, $CH_2$), 3.90 (2H, t, $CH_2$), 3.80 (2H, t, $CH_2$), 2.94 (4H, m, $CH_2$), 2.76-2.86 (4H, m, $CH_2$), 2.21 (3H, s, $CH_3$).

Compound 17

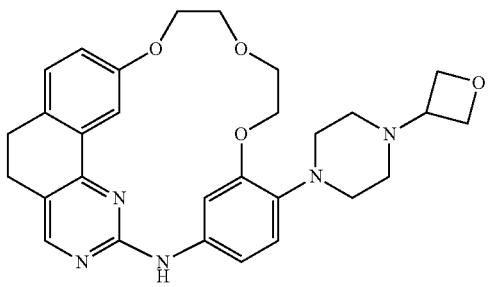 [SMILES: c1cc(N2CCN(C3COC3)CC2)c2cc1Nc1ncc3c(n1)-c1cc(ccc1CC3)OCCOCCO2]

Compound 17 was prepared according to the protocol described for the preparation of compound 3 starting with 200 mg of compound 2 and 250 mg of 1-(oxetan-3-yl)piperazine to afford 58 mg (25%) of compound 17.

LCMS (EI, m/z): (M+1) 516.60

$^1$H NMR: dH ppm (400 MHz, DMSO): 9.47 (1H, s, NH), 8.51-8.52 (1H, s, CH$_{arom}$), 8.38 (1H, s, CH$_{arom}$), 8.01-8.02 (1H, d, CH$_{arom}$), 7.26-7.28 (1H, d, CH$_{arom}$), 7.05-7.07 (1H, dd, CH$_{arom}$), 6.80-6.86 (2H, m, CH$_{arom}$), 4.54-4.57 (2H, m, CH$_2$), 4.45-4.47 (2H, m, CH$_2$), 4.22-4.24 (4H, m, CH$_2$), 3.73-3.78 (4H, m, CH$_2$), 3.43-3.48 (1H, m, CH), 2.97 (4H, m, CH$_2$), 2.82-2.86 (2H, m, CH$_2$), 2.75-2.79 (2H, m, CH$_2$), 2.40 (4H, m, CH$_2$).

Compound 18

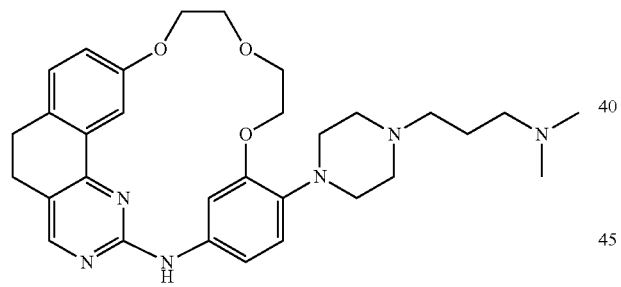

Compound 18 was prepared according to the protocol described for the preparation of compound 3 starting with 200 mg of compound 2 and 302 mg of N,N-dimethyl-3-(piperazin-1-yl)propan-1-amine to afford 32 mg (13%) of compound 18.

LCMS (EI, m/z): (M+1) 545.69

$^1$H NMR: dH ppm (400 MHz, DMSO): 9.46 (1H, s, NH), 8.51-8.52 (1H, s, CH$_{arom}$), 8.38 (1H, s, CH$_{arom}$), 8.01-8.02 (1H, d, CH$_{arom}$), 7.25-7.27 (1H, d, CH$_{arom}$), 7.05-7.07 (1H, dd, CH$_{arom}$), 6.79-6.85 (2H, m, CH$_{arom}$), 4.22-4.26 (4H, m, CH$_2$), 3.74-3.79 (4H, m, CH$_2$), 2.97 (4H, m, CH$_2$), 2.82-2.87 (2H, m, CH$_2$), 2.75-2.79 (2H, m, CH$_2$), 2.40 (4H, m, CH$_2$), 2.30-2.33 (2H, m, CH$_2$), 2.19-2.23 (2H, m, CH$_2$), 2.11 (6H, m, CH$_3$), 1.52-1.60 (2H, m, CH$_2$).

Compound 19

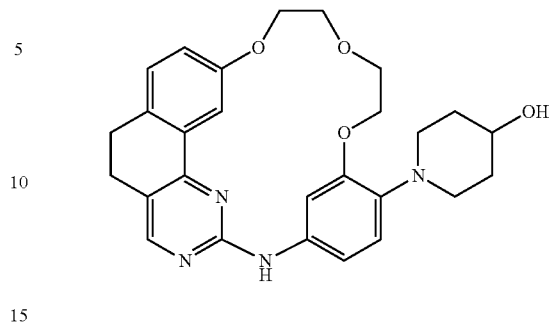

To 100 mg (0.212 mmol) of compound 32 in 1 mL of methanol and 1 mL of THF is added 24 mg (0.63 mmol) of NaBH$_4$ at 0° C. The reaction mixture is stirred at 25° C. for 15 hours. The reaction is hydrolyzed by slow addition of 1N HCl solution and extracted with ethyl acetate. The organic phase is dried over sodium sulfate, filtered and concentrated. The residue obtained is purified by chromatography on silica gel (eluent: ethyl acetate/methanol/ammonia: 90:8:2) to afford 46 mg (42%) of compound 19 as a yellow solid.

LCMS (EI, m/z): (M+1) 475.55

$^1$H NMR: dH ppm (400 MHz, DMSO): 9.45 (1H, s, NH), 8.50-8.51 (1H, d, CH$_{arom}$), 8.37 (1H, s, CH$_{arom}$), 8.01-8.02 (1H, d, CH$_{arom}$), 7.25-7.27 (1H, d, CH$_{arom}$), 7.05-7.07 (1H, dd, CH$_{arom}$), 6.78-6.86 (2H, m, CH$_{arom}$), 4.61-4.62 (1H, d, OH), 4.24 (4H, m, CH$_2$), 3.75-3.79 (4H, m, CH$_2$), 3.55 (1H, m, CH), 3.18-3.21 (2H, m, CH$_2$), 2.76-2.84 (2H, m, CH$_2$), 2.59-2.64 (2H, m, CH$_2$), 1.81-1.85 (2H, m, CH$_2$), 1.49-1.57 (2H, m, CH$_2$).

Compound 20

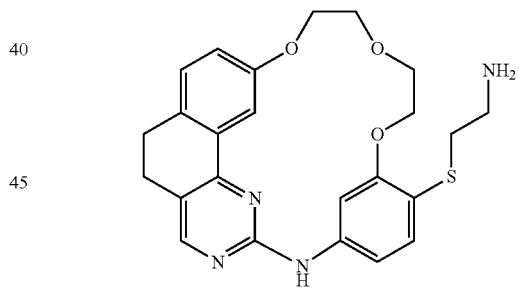

In a microwave reactor are mixed 200 mg (0.44 mmol) of compound 2, 126 mg (0.66 mmol) of cuprous iodide, 287 mg (0.88 mmol) of cesium carbonate and 156 mg (0.880 mmol) of tert-butyl (2-mercaptoethyl)carbamate. The reaction mixture is heated to 200° C. for 45 minutes. After returning to room temperature, water is added and the solid formed is filtered then purified by chromatography on silica gel (eluent: ethyl acetate/methanol/ammonia: 94:4:2) to afford 17 mg (7%) of compound 20 as a yellow solid.

LCMS (EI, m/z): (M+1) 451.55

$^1$H NMR: dH ppm (400 MHz, DMSO): 9.71 (1H, s, NH), 8.60-8.61 (1H, d, CH$_{arom}$), 8.43 (1H, 5, CH$_{arom}$), 8.02-8.03 (1H, d, CH$_{arom}$), 7.22-7.28 (2H, m, CH$_{arom}$), 7.05-7.08 (1H, dd, CH$_{arom}$), 6.83-6.86 (1H, dd, CH$_{arom}$), 4.23-4.26 (4H, m, CH$_2$), 3.80-3.83 (4H, m, CH$_2$), 3.74-3.77 (2H, m, CH$_2$), 2.76-2.84 (6H, m, CH$_2$), 2.66-2.67 (2H, m, CH$_2$).

Compound 21

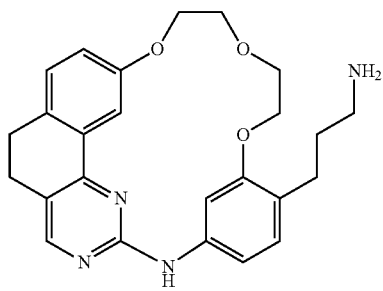 [SMILES: NCCCc1ccc2cc1OCCOCCOc1ccc3c(c1)-c1nc(ncc1CC3)N2]

In a round-bottom flask and under argon, introduce 0.3 g (0.568 mmol) of compound 33 in 50 mL of a mixture of THF/MeOH (1:1). Degas the mixture under argon and under vacuum. Add 6.04 mg (0.057 mmol) of Pd—C. Degas the mixture under argon and under vacuum then place in a round-bottom flask of hydrogen. The reaction mixture is stirred at 25° C. overnight then filtered on silica and rinsed with ethyl acetate then concentrated. The residue is dissolved in 10 mL of a solution of hydrochloric acid in isopropanol (5N). The solution is stirred at 45° C. for 1 hour. The solvent is evaporated and the reaction is hydrolyzed by slow addition of 1N NaOH solution and extracted with ethyl acetate. The organic phase is dried over sodium sulfate, filtered and concentrated. The residue obtained is purified by chromatography on silica gel (eluent: ethyl acetate/methanol/ammonia: 90:8:2) to afford 11.5 mg (7%) of compound 21 as a yellow solid.

LCMS (EI, m/z): (M+1) 433.51

$^1$H NMR: dH ppm (400 MHz, DMSO): 9.53 (1H, s, NH), 8.50 (1H, s, CH$_{arom}$), 8.40 (1H, s, CH$_{arom}$), 8.03 (1H, d, CH$_{arom}$), 7.25-7.28 (1H, m, CH$_{arom}$), 7.00-7.07 (2H, m, CH$_{arom}$), 6.74-6.79 (1H, dd, CH$_{arom}$), 4.18-4.24 (4H, m, CH$_2$), 3.73-3.84 (4H, m, CH$_2$), 2.75-2.85 (4H, m, CH$_2$), 1.59-1.66 (2H, m, CH$_2$), 2.51-2.59 (4H, m, CH$_2$).

Compound 22

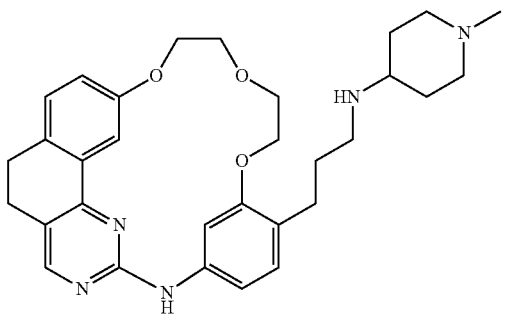 [SMILES: CN1CCC(NCCCc2ccc3cc2OCCOCCOc2ccc4c(c2)-c2nc(ncc2CC4)N3)CC1]

To a solution of 100 mg (0.23 mmol) of compound 21 in 7 mL of 1,2-dichloroethane is added 28 μL (0.23 mmol) of 1-methyl-4-piperidone then 13 μL (0.23 mmol) of acetic acid. To the reaction mixture is added in small fractions 186 mg (0.87 mmol) of sodium triacetoxyborohydride. The reaction mixture is stirred for 16 hours at room temperature. The solvent is then concentrated, the reaction mixture extracted with ethyl acetate and washed using saturated sodium hydroxide solution. The organic phases are combined, dried over magnesium sulfate then concentrated. The residue is purified by chromatography on silica gel (eluent: dichloromethane/methanol/ammonia: 95:4:1) to afford 14 mg (11%) of compound 22 as a yellow solid.

LCMS (EI, m/z): (M+1) 560.67

$^1$H NMR: dH ppm (400 MHz, DMSO): 9.52 (1H, s, NH), 8.50 (1H, s, CH$_{arom}$), 8.40 (1H, s, CH$_{arom}$), 8.02-8.03 (1H, d, CH$_{arom}$), 7.25-7.28 (1H, m, CH$_{arom}$), 7.04-7.07 (1H, d, CH$_{arom}$), 6.99-7.01 (1H, d, CH$_{arom}$), 6.74-6.76 (1H, d, CH$_{arom}$), 4.18-4.23 (4H, m, CH$_2$), 3.75-3.83 (4H, m, CH$_2$), 2.75-2.84 (4H, m, CH$_2$), 2.65-2.67 (2H, m, CH$_2$), 2.45-2.57 (6H, m, CH$_2$), 2.32 (1H, m, CH), 2.10 (3H, m, CH$_3$), 1.81-1.86 (2H, m, CH$_2$), 1.70-1.75 (2H, m, CH$_2$), 1.60-1.64 (2H, m, CH$_2$), 1.15-1.28 (1H, m, CH$_2$).

Compound 23

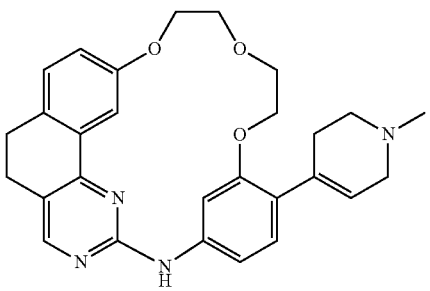 [SMILES: CN1CC=C(c2ccc3cc2OCCOCCOc2ccc4c(c2)-c2nc(ncc2CC4)N3)CC1]

In a 50 mL round-bottom flask is mixed 50 mg (0.09 mmol) of compound 34 in 2 mL of tetrahydrofuran then 0.5 mL (0.5 mmol) of lithium aluminum hydride (LAH) is added at 0° C. The reaction mixture is heated to 85° C. for 5 hours. After returning to room temperature, the reaction is hydrolyzed by addition of sodium sulfate decahydrate then ethyl acetate. A step of filtration on silica then a step of extraction with ethyl acetate follow. The organic phase is dried over sodium sulfate, filtered and concentrated. The residue obtained is purified by chromatography on silica gel (eluent: ethyl acetate/methanol/ammonia: 94:4:2) to afford 15 mg (35%) of compound 23 as a yellow solid.

LCMS (EI, m/z): (M+1) 471.56

$^1$H NMR: dH ppm (400 MHz, DMSO): 9.65 (1H, s, NH), 8.56-8.57 (1H, d, CH$_{arom}$), 8.42 (1H, s, CH$_{arom}$), 8.03-8.04 (1H, s, CH$_{arom}$), 7.26-7.28 (1H, d, CH$_{arom}$), 7.05-7.08 (1H, dd, CH$_{arom}$), 7.01-7.04 (1H, dd, CH$_{arom}$), 6.79-6.82 (1H, dd, CH$_{arom}$), 5.75 (1H, m, CH), 4.14-4.25 (4H, m, CH$_2$), 3.74-3.79 (4H, m, CH$_2$), 2.76-2.86 (4H, m, CH$_2$), 2.99 (2H, m, CH$_2$), 2.45-2.53 (4H, m, CH$_2$), 2.27 (3H, s, CH$_3$).

Compound 24

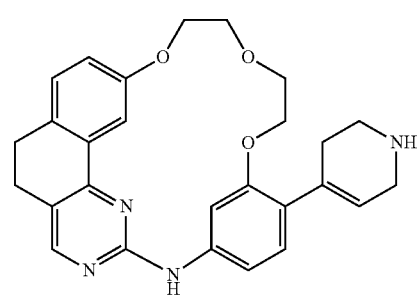 [SMILES: C1=C(c2ccc3cc2OCCOCCOc2ccc4c(c2)-c2nc(ncc2CC4)N3)CCNC1]

To 50 mg (0.09 mmol) of compound 34 is added dropwise 1 mL of a solution of hydrochloric acid (5N) in isopropanol. The solution is stirred at 45° C. for 2 h 50 min. The solid formed is filtered then washed twice with 20 mL of water. The solid formed is placed in basic medium and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 25 mg (51%) of compound 24 as a yellow solid.

LCMS (EI, m/z): (M+1) 457.54

$^1$H NMR: dH ppm (400 MHz, DMSO): 9.56 (1H, s, NH), 8.57 (1H, d, CH$_{arom}$), 8.42 (1H, s, CH$_{arom}$), 8.03-8.04 (1H, s, CH$_{arom}$), 7.26-7.28 (1H, d, CH$_{arom}$), 7.05-7.08 (1H, dd, CH$_{arom}$), 7.01-7.04 (1H, d, CH$_{arom}$), 6.80-6.82 (1H, dd, CH$_{arom}$), 5.78 (1H, m, CH), 4.15-4.24 (4H, m, CH$_2$), 3.75-3.80 (4H, m, CH$_2$), 2.77-2.85 (4H, m, CH$_2$), 2.99 (2H, m, CH$_2$), 2.45-2.53 (4H, m, CH$_2$).

Compound 25

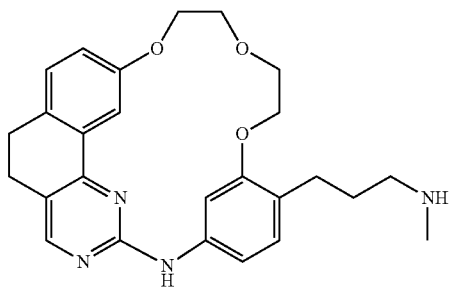 [SMILES: CNCCCc1ccc2cc1OCCOCCOc1ccc3c(c1)-c1nc(ncc1CC3)N2]

In a 50 mL round-bottom flask is mixed 100 mg (0.09 mmol) of compound 21 in its Boc-protected form in 4 mL of tetrahydrofuran, then 0.93 mL (0.93 mmol) of LAH is added at 0° C. The reaction mixture is heated to 85° C. for 5 hours. After returning to room temperature, the reaction is hydrolyzed by addition of sodium sulfate decahydrate then ethyl acetate. A step of filtration and a step of extraction with ethyl acetate follow. The organic phase is dried over sodium sulfate, filtered and concentrated. The residue obtained is purified by chromatography on silica gel (eluent: ethyl acetate/methanol/ammonia: 94:4:2) to afford 10 mg (12%) of compound 25 as a yellow solid.

LCMS (EI, m/z): (M+1) 447.54

$^1$H NMR: dH ppm (400 MHz, DMSO): 9.52 (1H, s, NH), 8.50-8.51 (1H, d, CH$_{arom}$), 8.40 (1H, s, CH$_{arom}$), 8.03-8.04 (1H, s, CH$_{arom}$), 7.25-7.27 (1H, d, CH$_{arom}$), 7.04-7.07 (1H, dd, CH$_{arom}$), 6.99-7.01 (1H, d, CH$_{arom}$), 6.74-6.76 (1H, dd, CH$_{arom}$), 4.18-4.24 (4H, m, CH$_2$), 3.75-3.83 (4H, m, CH$_2$), 2.76-2.84 (4H, m, CH$_2$), 2.43-2.55 (5H, m, CH$_2$), 2.26 (3H, m, CH$_3$).

Compound 26

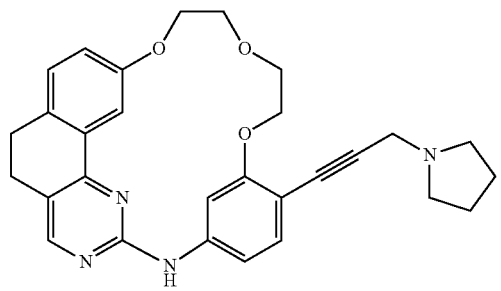 [SMILES: C(#Cc1ccc2cc1OCCOCCOc1ccc3c(c1)-c1nc(ncc1CC3)N2)CN1CCCC1]

In a 10 mL vial are mixed 1 g (2.201 mmol) of compound 2, 0.24 g (0.50 mmol) of 2-(dicyclohexylphosphino)-2',4',6'-triisopropylbiphenyl, 42 mg (0.11 mmol) of benzonitrile palladium(II) chloride, 0.72 g (3.96 mmol) of 1-(prop-2-yn-1-yl)pyrrolidine and 2.15 g (6.60 mmol) of cesium carbonate in 9 mL of dimethylformamide at room temperature. 0.85 g (2.64 mmol) of tetrabutylammonium bromide is added to the reaction mixture. The reaction mixture is heated to 80° C. for 5 hours. After returning to room temperature, the reaction is hydrolyzed by slow addition of water and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 233 mg (21%) of compound 26 as a yellow solid.

LCMS (EI, m/z): (M+1) 483.57

$^1$H NMR: dH ppm (400 MHz, DMSO): 9.85 (1H, s, NH), 8.64 (1H, s, CH$_{arom}$), 8.45 (1H, s, CH$_{arom}$), 8.03 (1H, s, CH$_{arom}$), 7.27-7.29 (1H, d, CH$_{arom}$), 7.21-7.23 (1H, d, CH$_{arom}$), 7.07-7.08 (1H, d, CH$_{arom}$), 6.81-6.83 (1H, d, CH$_{arom}$), 4.24-4.27 (4H, m, CH$_2$), 3.76-3.79 (4H, m, CH$_2$), 3.59 (2H, m, CH$_2$), 2.80-2.83 (4H, m, CH$_2$), 2.50-2.58 (4H, m, CH$_2$), 1.72 (4H, m, CH$_2$).

Compound 27

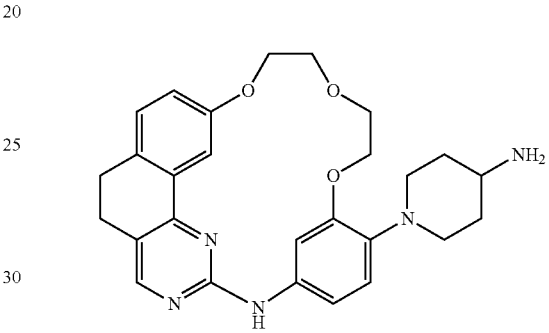

To a solution of 100 mg (0.23 mmol) of compound 32 in 2.5 mL of methanol are added 0.7 g of 4 A molecular sieve and 100 mg (2.30 mmol) of ammonium acetate. The reaction mixture is stirred for 20 minutes at room temperature then 116 mg (1.84 mmol) of sodium cyanoborohydride is added. The reaction mixture is stirred for 16 hours at 60° C. The solvent is then concentrated, the reaction mixture extracted with ethyl acetate and washed using saturated sodium hydroxide solution. The organic phases are combined, dried over magnesium sulfate then concentrated. The residue is purified by chromatography on silica gel (eluent: ethyl acetate/methanol/ammonia: 95:4:1) to afford 20 mg (17%) of compound 27 as a yellow solid.

LCMS (EI, m/z): (M+1) 474.57

$^1$H NMR: dH ppm (400 MHz, DMSO): 9.44 (1H, s, NH), 8.50 (1H, s, CH$_{arom}$), 8.37 (1H, s, CH$_{arom}$), 8.01-8.03 (1H, d, CH$_{arom}$), 7.25-7.27 (1H, d, CH$_{arom}$), 7.05-7.09 (1H, dd, CH$_{arom}$), 6.77-6.85 (2H, m, CH$_{arom}$), 4.22-4.25 (4H, m, CH$_2$), 3.74-3.82 (4H, m, CH$_2$), 3.24-3.29 (2H, m, NH$_2$), 2.74-2.86 (4H, m, CH$_2$), 2.48-2.86 (6H, m, CH$_2$), 1.75-1.80 (2H, m, CH$_2$), 1.35-1.44 (1H, m, CH).

Compound 28

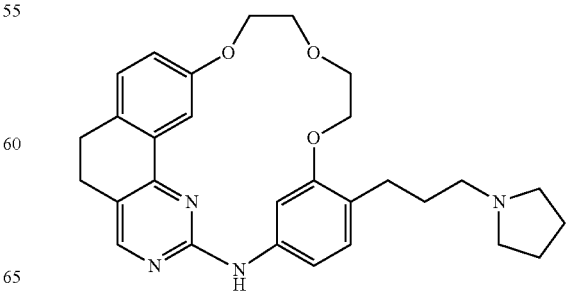

In a round-bottom flask and under argon, introduce 0.20 g (0.42 mmol) of compound 26 in 50 mL of a mixture of THF/MeOH (1:1). Degas the mixture under argon and under vacuum. Add 4.56 mg (0.043 mmol) of Pd—C. Degas the mixture under argon and under vacuum then place in a round-bottom flask of hydrogen. The reaction mixture is stirred at 25° C. overnight then filtered on silica and rinsed with ethyl acetate then concentrated. The residue obtained is purified by chromatography on silica gel (eluent: ethyl acetate/methanol/ammonia: 90:8:2) to afford 71 mg (34%) of compound 28 as a yellow solid.

LCMS (EI, m/z): (M+1) 487.61

$^1$H NMR: dH ppm (400 MHz, DMSO): 9.52 (1H, s, NH), 8.50 (1H, s, CH$_{arom}$), 8.40 (1H, s, CH$_{arom}$), 8.02-8.03 (1H, d, CH$_{arom}$), 7.25-7.27 (1H, d, CH$_{arom}$), 7.04-7.07 (1H, dd, CH$_{arom}$), 6.99-7.01 (1H, m, CH$_{arom}$), 6.74-6.76 (1H, d, CH$_{arom}$), 4.18-4.23 (4H, m, CH$_2$), 3.75-3.82 (4H, m, CH$_2$), 2.76-2.88 (4H, m, CH$_2$), 2.32-2.39 (8H, m, CH$_2$), 1.62-1.70 (6H, m, CH$_2$).

Compound 29

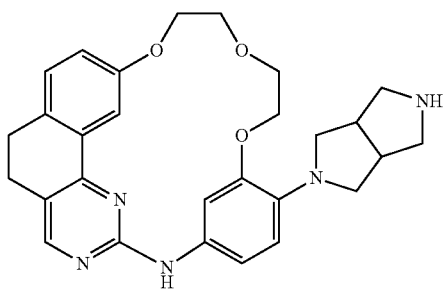 [SMILES: c1cc(N2CC3CNCC3C2)c2cc1Nc1ncc3c(n1)-c1cc(ccc1CC3)OCCOCCO2]

To 40 mg (0.07 mmol) of compound 35 is added dropwise 1 mL of a solution of hydrochloric acid (5N) in isopropanol. The solution is stirred at 45° C. for 2 h 50 min. The solid formed is filtered then washed twice with 20 mL of water. The solid formed is placed in basic medium and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 11 mg (33%) of compound 29 as a yellow solid.

LCMS (EI, m/z): (M+1) 486.58

$^1$H NMR: dH ppm (400 MHz, DMSO): 9.40 (1H, s, NH), 8.50-8.51 (1H, d, CH$_{arom}$), 8.36 (1H, s, CH$_{arom}$), 8.02-8.03 (1H, d, CH$_{arom}$), 7.25-7.27 (1H, d, CH$_{arom}$), 7.05-7.07 (1H, dd, CH$_{arom}$), 6.70-6.79 (2H, m, CH$_{arom}$), 4.14-4.25 (4H, m, CH$_2$), 3.74-3.80 (4H, m, CH$_2$), 3.09-3.13 (2H, m, CH$_2$), 2.91-2.97 (4H, m, CH$_2$), 2.73-2.84 (4H, m, CH$_2$), 2.66 (2H, m, CH$_2$), 2.50-2.55 (2H, m, CH$_2$).

Compound 30

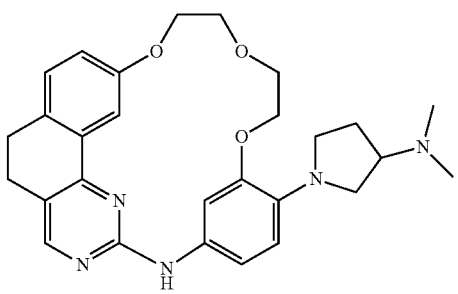 [SMILES: CN(C)C1CCN(c2ccc3cc2OCCOCCOc2ccc4c(c2)-c2nc(ncc2CC4)N3)C1]

Compound 30 was prepared according to the protocol described for the preparation of compound 3 starting with 100 mg of compound 2 and 352 mg of N,N-dimethylpyrrolidin-3-amine to afford 2.4 mg (2.4%) of compound 30.

LCMS (EI, m/z): (M+1) 488.59

$^1$H NMR: dH ppm (400 MHz, DMSO): 9.35 (1H, s, NH), 8.47-8.48 (1H, d, CH$_{arom}$), 8.35 (1H, s, CH$_{arom}$), 8.01-8.02 (1H, d, CH$_{arom}$), 7.24-7.25 (1H, d, CH$_{arom}$), 7.04-7.06 (1H, dd, CH$_{arom}$), 6.75-6.77 (1H, dd, CH$_{arom}$), 6.64-6.66 (1H, d, CH$_{arom}$), 4.05-4.27 (4H, m, CH$_2$), 3.73-3.79 (4H, m, CH$_2$), 3.10-3.23 (3H, m, CH and CH$_2$), 2.69-2.84 (4H, m, CH$_2$), 2.17 (6H, m, CH$_3$), 1.99-2.05 (2H, m, CH$_2$), 1.66-1.73 (2H, m, CH$_2$).

Compound 31

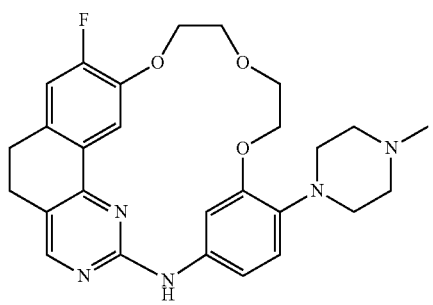 [SMILES: CN1CCN(c2ccc3cc2OCCOCCOc2cc4c(cc2F)CCc2cnc(nc2-4)N3)CC1]

Compound 31 was prepared according to the protocol described for the preparation of compound 3 starting with 300 mg of intermediate 11 and 127 mg of 1-methylpiperazine to afford 37 mg (11%) of compound 31.

LCMS (EI, m/z): (M+1) 492.56

$^1$H NMR: dH ppm (400 MHz, DMSO): 9.47 (1H, s, NH), 8.49-8.50 (1H, d, CH$_{arom}$), 8.36 (1H, s, CH$_{arom}$), 8.13-8.16 (1H, d, CH$_{arom}$), 7.25-7.28 (1H, d, CH$_{arom}$), 6.80-6.86 (2H, m, CH$_{arom}$), 4.23-4.29 (4H, m, CH$_2$), 3.75 (4H, m, CH$_2$), 2.94 (4H, m, CH$_2$), 2.74-2.87 (4H, m, CH$_2$), 2.45 (4H, m, CH$_2$), 2.21 (3H, s, CH$_3$).

Compound 32

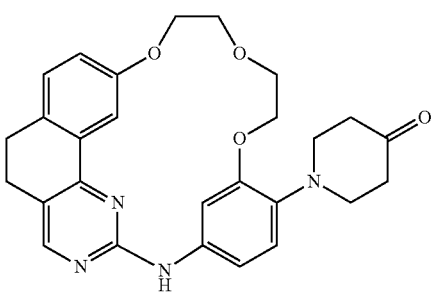 [SMILES: O=C1CCN(c2ccc3cc2OCCOCCOc2ccc4c(c2)-c2nc(ncc2CC4)N3)CC1]

To 246 mg (0.476 mmol) of compound 6 is added dropwise 3.6 mL of a solution of hydrochloric acid in isopropanol (5N). The solution is stirred at 100° C. for 12 hours. The solid formed is placed in basic medium and extracted with ethyl acetate. The organic phase is dried over sodium sulfate, filtered and concentrated to afford 209 mg (93%) of compound 32 as a yellow solid.

LCMS (EI, m/z): (M+1) 573.53

Compound 33

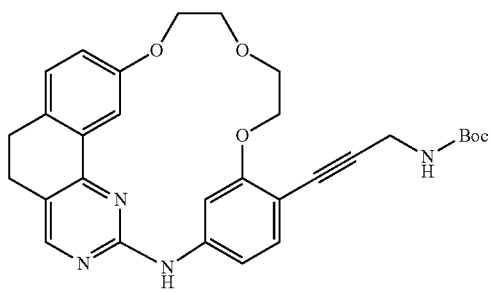 [SMILES: CC(C)(C)OC(=O)NCC#Cc1ccc2cc1OCCOCCOc1ccc3c(c1)-c1nc(ncc1CC3)N2]

In a 10 mL vial are mixed 2.5 g (5.5 mmol) of compound 2, 0.60 g (1.26 mmol) of 2-(dicyclohexylphosphino)-2',4',6'-triisopropylbiphenyl, 106 mg (0.27 mmol) of benzonitrile palladium(II) chloride, 1.53 g (9.90 mmol) of prop-2-ynyl-carbamic acid tert-butyl ester and 5.38 g (16.5 mmol) of cesium carbonate in 24 mL of dimethylformamide at room temperature. 2.12 g (6.60 mmol) of tetrabutylammonium bromide is added to the reaction mixture. The reaction mixture is heated to 80° C. for 5 hours. After returning to room temperature, the reaction is hydrolyzed by slow addition of water and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 1.3 g (45%) of compound 33 as a yellow solid.

LCMS (EI, m/z): (M+1) 529.59

$^1$H NMR: dH ppm (400 MHz, DMSO): 9.86 (1H, s, NH), 8.62-8.63 (1H, d, CH$_{arom}$), 8.45 (1H, s, CH$_{arom}$), 8.03-8.04 (1H, d, CH$_{arom}$), 7.25 (1H, t, NH), 7.27-7.29 (1H, d, CH$_{arom}$), 7.20-7.22 (1H, d, CH$_{arom}$), 7.06-7.08 (1H, dd, CH$_{arom}$), 6.82-6.84 (1H, dd, CH$_{arom}$), 4.25-4.29 (4H, m, CH$_2$), 3.96-3.98 (2H, m, CH$_2$), 3.76-3.81 (4H, m, CH$_2$), 2.79-2.86 (4H, m, CH$_2$), 1.41 (9H, s, CH$_3$).

Compound 34

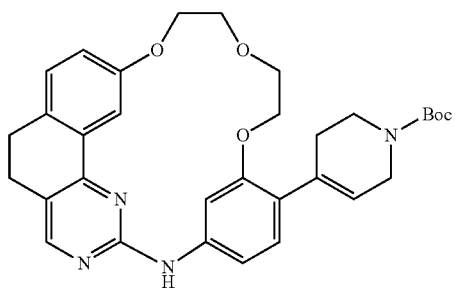 [SMILES: CC(C)(C)OC(=O)N1CC=C(c2ccc3cc2OCCOCCOc2ccc4c(c2)-c2nc(ncc2CC4)N3)CC1]

In a microwave reactor are mixed 463 mg (1.01 mmol) of compound 2, 0.3 g (0.970 mmol) of N-Boc-1,2,3,6-tetrahydropyridine-4-boronic acid pinacol ester and 0.056 g (0.049 mmol) of tetrakis(triphenylphosphine)palladium(0) in 8 mL of tetrahydrofuran. The reaction mixture is stirred at room temperature for 10 minutes then 0.25 g (2.426 mmol) of sodium carbonate dissolved in 1 mL of water is added at room temperature. The reaction mixture is heated to 150° C. for 20 minutes. After returning to room temperature, ethyl acetate is added and the organic phase is washed with saturated sodium chloride solution, dried over magnesium sulfate and filtered. The filtrate is evaporated and the residue purified by silica column chromatography using Compan-ion® (eluent: dichloromethane/methanol/ammonia: 95:4:1) to afford 87 mg (12%) of compound 34 as a yellow solid LCMS (EI, m/z): (M+1) 557.65

$^1$H NMR: dH ppm (400 MHz, DMSO): 9.67 (1H, s, NH), 8.57 (1H, s, CH$_{arom}$), 8.42 (1H, s, CH$_{arom}$), 8.03- (1H, s, CH$_{arom}$), 7.26-7.28 (1H, m, CH$_{arom}$), 7.03-7.06 (1H, m, CH$_{arom}$), 7.01-7.04 (1H, dd, CH$_{arom}$), 6.79-6.82 (1H, dd, CH$_{arom}$), 5.76 (1H, m, CH), 4.16-4.24 (4H, m, CH$_2$), 3.74-3.79 (4H, m, CH$_2$), 2.76-2.88 (4H, m, CH$_2$), 2.99 (2H, m, CH$_2$), 2.45-2.53 (4H, m, CH$_2$), 1.42 (9H, s, CH$_3$).

Compound 35

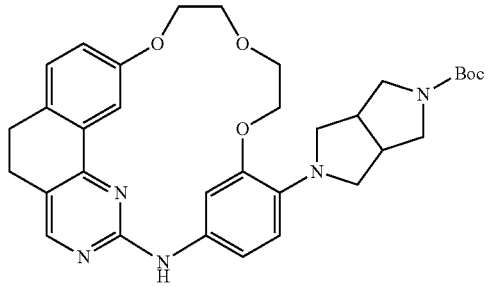 [SMILES: CC(C)(C)OC(=O)N1CC2CN(c3ccc4cc3OCCOCCOc3ccc5c(c3)-c3nc(ncc3CC5)N4)CC2C1]

Compound 35 was prepared according to the protocol described for the preparation of compound 3 starting with 400 mg of compound 2 and 748 mg of tert-butyl hexahydropyrrolo[3,4-c]pyrrole-2(1H)-carboxylate to afford 200 mg (38%) of compound 35.

LCMS (EI, m/z): (M+1) 586.69

Compound 36

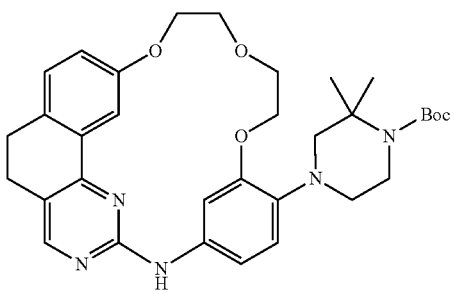 [SMILES: CC(C)(C)OC(=O)N1CCN(c2ccc3cc2OCCOCCOc2ccc4c(c2)-c2nc(ncc2CC4)N3)CC1(C)C]

Compound 36 was prepared according to the protocol described for the preparation of compound 3 starting with 200 mg of compound 2 and 442 mg of tert-butyl 2,2-dimethylpiperazine-1-carboxylate to afford 100 mg (12%) of compound 36.

LCMS (EI, m/z): (M+1) 586.69

Compound 37

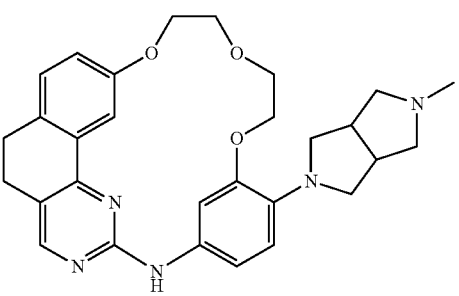 [SMILES: CN1CC2CN(c3ccc4cc3OCCOCCOc3ccc5c(c3)-c3nc(ncc3CC5)N4)CC2C1]

In a 50 mL round-bottom flask are mixed 68 mg (0.11 mmol) of compound 35 in 2.47 mL of THF and 0.58 mL of a 1M solution of LAH in THF (0.58 mmol) at 0° C. The reaction mixture is heated to 85° C. for 3 hours. After returning to room temperature, the reaction is hydrolyzed by addition of sodium sulfate decahydrate then with ethyl acetate. The mixture is filtered on silica and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 14 mg (23%) of compound 37 as a yellow solid.

LCMS (EI, m/z): (M+1): 500.60

$^1$H NMR: dH ppm (400 MHz, DMSO): 9.41 (1H, s, NH), 8.51-8.52 (1H, d, CH$_{arom}$), 8.37 (1H, s, CH$_{arom}$), 8.02-8.03 (1H, d, CH$_{arom}$), 7.25-7.27 (1H, d, CH$_{arom}$), 7.05-7.08 (1H, dd, CH$_{arom}$), 6.76-6.79 (1H, dd, CH$_{arom}$), 6.70-6.72 (1H, d, CH$_{arom}$), 4.16-4.25 (4H, m, CH$_2$), 3.74-3.80 (4H, m, CH$_2$), 3.11-3.15 (2H, m, CH$_2$), 2.91-2.95 (2H, m, CH$_2$), 2.82-2.86 (2H, m, CH$_2$), 2.71-2.78 (4H, m, CH$_2$), 2.61-2.66 (2H, m, CH$_2$), 2.24-2.26 (2H, m, CH), 2.21 (3H, m, CH$_3$).

Compound 38

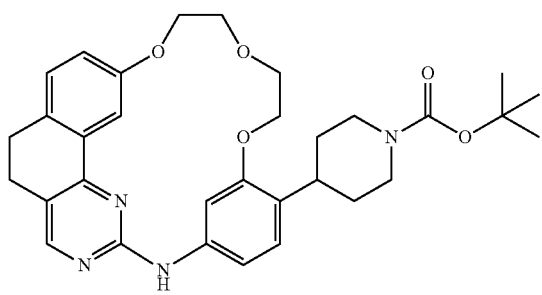 [SMILES: CC(C)(C)OC(=O)N1CCC(c2ccc3cc2OCCOCCOc2ccc4c(c2)-c2nc(ncc2CC4)N3)CC1]

In a round-bottom flask and under argon, introduce 0.49 g (0.89 mmol) of compound 34 in 50 mL of a mixture of 1,4-dioxane/ethanol (345 mL/25 mL). Degas the mixture again under argon and under vacuum. Add 3.15 g (2.96 mmol) of Pd—C. Repeat the degassing of the mixture under argon and under vacuum then place in a round-bottom flask of hydrogen. The reaction mixture is stirred at 25° C. overnight, filtered on silica, rinsed with ethyl acetate then concentrated to afford 300 mg (60%) of compound 38 as a yellow oil. LCMS (EI, m/z): (M+1) 559.66

Compound 39

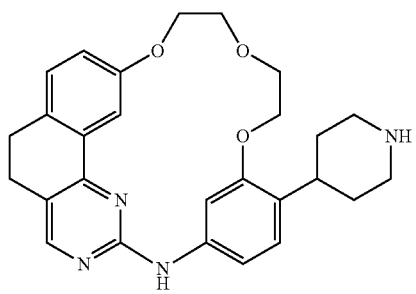 [SMILES: c1cc(C2CCNCC2)c2cc1Nc1ncc3c(n1)-c1cc(ccc1CC3)OCCOCCO2]

To 300 mg (0.53 mmol) of compound 38 is added dropwise 1 mL of a solution of hydrochloric acid (5N) in isopropanol. The solution is stirred at 45° C. for 3 hours. The solvent is evaporated. The solid formed is placed in basic medium and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 29 mg (11%) of compound 39 as a yellow solid.

LCMS (EI, m/z): (M+1) 459.55.

$^1$H NMR: dH ppm (400 MHz, DMSO): 9.56 (1H, s, NH), 8.50 (1H, d, CH$_{arom}$), 8.40 (1H, s, CH$_{arom}$), 8.03-8.04 (1H, s, CH$_{arom}$), 7.26-7.28 (1H, d, CH$_{arom}$), 7.03-7.08 (2H, m, CH$_{arom}$), 6.79-6.82 (1H, dd, CH$_{arom}$), 4.15-4.24 (4H, m, CH$_2$), 3.74-3.80 (5H, m, CH$_2$ and CH), 2.99-3.02 (2H, m, CH$_2$), 2.77-2.89 (4H, m, CH$_2$), 2.99 (2H, m, CH$_2$), 1.50 (4H, m, CH$_2$).

Compound 40

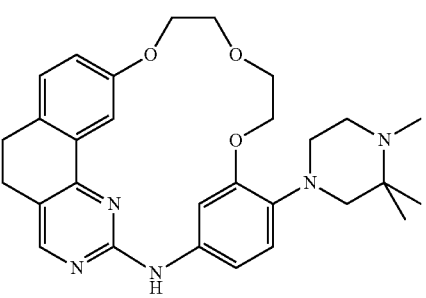 [SMILES: CN1CCN(c2ccc3cc2OCCOCCOc2ccc4c(c2)-c2nc(ncc2CC4)N3)CC1(C)C]

In a 50 mL round-bottom flask are mixed 100 mg (0.17 mmol) of compound 36 in 3.62 mL of THF and 0.85 mL of a 1M solution of LAH in THF (0.85 mmol) at 0° C. The reaction mixture is heated to 85° C. for 5 hours. After returning to room temperature, the reaction is hydrolyzed by addition of sodium sulfate decahydrate then with ethyl acetate. The mixture is filtered on silica and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 8.10 mg (10%) of compound 40 as a yellow solid.

LCMS (EI, m/z): (M+1) 502.62

$^1$H NMR: dH ppm (400 MHz, MeOH): 8.58 (1H, s, CH$_{arom}$), 8.25 (1H, s, CH$_{arom}$), 8.14 (1H, s, CH$_{arom}$), 7.20-7.22 (1H, d, CH$_{arom}$), 7.03-7.04 (1H, dd, CH$_{arom}$), 6.87-6.89 (1H, d, CH$_{arom}$), 6.68-6.71 (1H, dd, CH$_{arom}$), 4.27-4.34 (4H, m, CH$_2$), 3.81-3.88 (4H, m, CH$_2$), 2.88 (2H, s, CH$_2$), 2.27-2.87 (8H, m, CH$_2$), 2.28 (3H, s, CH$_3$), 1.17 (6H, s, CH$_3$).

Compound 41

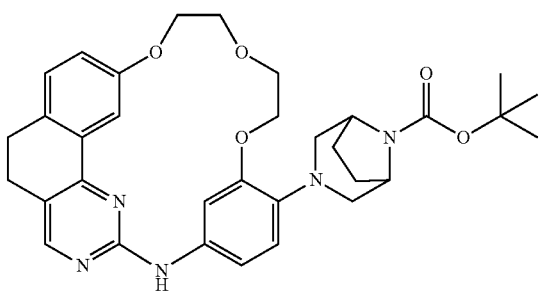 [SMILES: CC(C)(C)OC(=O)N1C2CCC1CN(c1ccc3cc1OCCOCCOc1ccc4c(c1)-c1nc(ncc1CC4)N3)C2]

Compound 41 was prepared according to the protocol described for the preparation of compound 3 starting with 0.37 g of compound 2 and 0.34 g of the amine tert-butyl (1R,5S)-3,8-diazabicyclo[3.2.1]octane-8-carboxylate.

LCMS (EI, m/z): (M+1) 586.69

Compound 42

To 477 mg (0.81 mmol) of compound 41 is added dropwise 15 mL of a solution of hydrochloric acid (5N) in isopropanol. The solution is stirred at 45° C. for 1 h 30 min. The solvent is evaporated and the solid formed is placed in basic medium then extracted with ethyl acetate. The organic phase is dried over sodium sulfate, filtered and concentrated. The residue thus obtained is purified by chromatography on silica gel (eluent: ethyl acetate/methanol/ammonia: 94:4:2) to afford 98 mg (25%) of compound 42 as a yellow solid.

LCMS (EI, m/z): (M+1) 486.57

$^1$H NMR: dH ppm (400 MHz, DMSO): 9.39 (1H, s, NH), 8.50 (1H, d, $CH_{arom}$), 8.36 (1H, s, $CH_{arom}$), 8.02-8.03 (1H, d, $CH_{arom}$), 7.25-7.27 (1H, d, $CH_{arom}$), 7.05-7.08 (1H, dd, $CH_{arom}$), 6.74 (2H, m, $CH_{arom}$), 4.23-4.25 (4H, m, $CH_2$), 3.86 (2H, m, $CH_2$), 3.74-3.79 (4H, m, $CH_2$), 2.94-2.97 (2H, m, $CH_2$), 2.73-2.86 (4H, m, $CH_2$), 2.54-2.57 (2H, m, $CH_2$ and CH), 1.79 (4H, m, $CH_2$).

Compound 43

Compound 43 was prepared according to the protocol described for the preparation of compound 3 starting with 0.40 g of compound 2 and 0.34 g of the amine tert-butyl (1S,4S)-2,5-diazabicyclo[2.2.1]heptane-2-carboxylate. Compound 43 thus obtained was used as such.

LCMS (EI, m/z): (M+1) 572.66

Compound 44

To 200 mg (0.35 mmol) of compound 43 is added dropwise 5 mL of a solution of hydrochloric acid (5N) in isopropanol. The solution is stirred at 45° C. for 1 h 15 min. The solvent is evaporated and the solid formed is placed in basic medium and extracted with ethyl acetate. The organic phase is dried over sodium sulfate, filtered and concentrated. The residue obtained is purified by chromatography on silica gel (eluent: ethyl acetate/methanol/ammonia: 94:4:2) to afford 16 mg (9%) of compound 44 as a yellow solid.

LCMS (EI, m/z): (M+1) 472.55

$^1$H NMR: dH ppm (400 MHz, DMSO) 9.31 (1H, s, NH), 8.44-8.45 (1H, d, $CH_{arom}$), 8.34 (1H, s, $CH_{arom}$), 8.01-8.02 (1H, d, $CH_{arom}$), 7.25-7.27 (1H, d, $CH_{arom}$), 7.04-7.06 (1H, dd, $CH_{arom}$), 6.73-6.75 (1H, dd, $CH_{arom}$), 6.56-6.58 (1H, d, $CH_{arom}$), 4.01-4.26 (4H, m, $CH_2$), 3.99-3.01 (1H, m, CH), 3.74-3.79 (4H, m, $CH_2$), 3.60-3.63 (1H, m, CH), 3.49 (1H, m, CH), 2.99-3.02 (1H, m, CH), 2.80-2.85 (4H, m, $CH_2$), 2.72-2.77 (2H, m, $CH_2$), 1.54-1.74 (2H, m, $CH_2$).

2. Biological Activity of the Compounds According to the Invention

The following abbreviations were used:

ATP: Adenosine-5'-triphosphate

IMDM: Iscove's Modified Dulbecco's Medium

PSFG: Penicillin Streptomycin FunGizone

RPMI: Roswell Park Memorial Institute medium

FCS: Fetal calf serum

Measurement of the In Vitro Inhibitory Activities of the Compounds According to the Invention:

FLT3 (#PV3182), JAK2 (#PV4210) and JAK3 (#PV3855) recombinant enzymes were purchased from Life Technologies. FLT3-ITD (#0778-0000-1) and FLT3$^{D835Y}$ (#14-610) proteins were purchased from ProQinase and Merck Millipore, respectively. All the tests were carried out in 384-well plates. The principle of these binding tests is based on the LanthaScreen® TR-FRET methodology from Life Technologies.

FLT3 Tests.

The reaction mixture (15 μL total volume) contains the following compounds: 15 nM FLT3, FLT3-ITD or FLT3$^{D835Y}$, 3 nM kinase tracer 236 (Life Technologies, #PV5592) and 6 nM LanthaScreen® anti-GST antibody coupled to a europium chelate (Life Technologies, #PV5594) for FLT3-ITD and FLT3$^{D835Y}$ or 6 nM LanthaScreen® anti-His antibody coupled to a europium chelate (Life Technologies, #PV5596) for FLT3.

JAK Tests.

The reaction mixture (15 μL total volume) contains the following compounds: 15 nM JAK2 or JAK3, 150 nM kinase tracer 236 (Life Technologies, #PV5592) for JAK2 or 3 nM for JAK3 and 6 nM LanthaScreen® anti-GST antibody coupled to a europium chelate (Life Technologies, #PV5594) for both enzymes.

The compounds are evaluated at 8 different concentrations prepared by making dilutions from a starting 10 mM stock solution in dimethylsulfoxide (DMSO) (Sigma, #D8418). The final DMSO concentration in the test is 1%. The reaction is carried out at 25° C. for 1 hour and detected on the EnVision® reader (Perkin Elmer) according to the recommendations of the supplier, Life Technologies.

The results are presented (Table 1) as the concentration values of the compound at which 50% of the kinase activity is inhibited, IC$_{50}$ (μM), generated using the PRISM software (GraphPad).

TABLE 1

Inhibition (IC$_{50}$ (µM)) of FLT3, FLT3 ID, FLT3 D835Y, JAK2 and JAK3 enzymes by the compounds according to the invention (ND = not determined).

| Compound | FLT3 | FLT3-ITD | FLT3$^{D835Y}$ | JAK2 | JAK3 |
|---|---|---|---|---|---|
| 3 | 0.0025 | 0.00014 | 0.003 | 0.0175 | 0.054 |
| 5 | 0.0044 | 0.0013 | 0.00066 | 0.013 | 0.030 |
| 7 | 0.018 | 0.0064 | 0.0072 | 0.0400 | 0.120 |
| 10 | 0.006 | 0.0013 | 0.0011 | 0.0077 | 0.060 |
| 14 | 0.007 | 0.002 | 0.0032 | 0.034 | 0.070 |
| 19 | 0.0036 | 0.0024 | 0.0053 | 0.020 | 0.030 |
| 23 | 0.0045 | 0.0017 | 0.0045 | 0.130 | 0.110 |
| 29 | 0.00370 | 0.000790 | 0.00190 | 0.0115 | 0.0180 |
| 30 | 0.0032 | 0.001 | 0.0032 | 0.010 | 0.0180 |
| 40 | 0.0019 | 0.00051 | 0.0010 | 0.00725 | 0.0176 |
| 42 | 0.0032 | 0.0011 | ND | 0.00670 | 0.0130 |
| 44 | 0.0052 | 0.0015 | ND | 0.0335 | 0.035 |

The compounds according to the invention have a strong inhibitory activity on both FLT3 enzymes (wild or mutated form) and JAK2 and 3 enzymes.

In Vitro Measurement of the Antiproliferative Activity of the Compounds According to the Invention:

Cell Lines.

The characteristics of the cell lines used are as follows (Table 2):

TABLE 2

Characteristics of the cell lines used.

| Cell lines | Supplier | Tumor origin | Oncogene expressed | Basal culture medium | Seeding (Cell density/well) |
|---|---|---|---|---|---|
| MV4-11 | DSMZ | Acute myeloid leukemia | FLT3-ITD | IMDM, 10% FCS, PSFG | 0.4 · 10$^5$ cells/well (100 µL) |
| MOLM-13 | DSMZ | Acute myeloid leukemia | FLT3-ITD | RPMI 1640, 15% FCS, PSFG | 0.3 · 10$^5$ cells/well (100 µL) |

Measurement of Antiproliferative Activity.

MV4-11 and MOLM-13 cell lines are cultured in the culture medium specified in Table 2 above and according to the supplier's recommendations. The tests are carried out in 96-well plates. The cells are divided in two at D0. At D1, they are seeded and treated with the compounds at various concentrations and incubated for 72 h at 37° C. and 5% CO$_2$. The dilution of the compounds from stock solutions in DMSO (Sigma, #D8418) was made semi-logarithmically for a final concentration in the culture medium of 0.1%. At day 4, cell viability is evaluated by assaying the ATP released by the living cells using the ATPLite® kit (Perkin Elmer, #6016947). The EC$_{50}$ values (concentration of the compound necessary to obtain 50% of the maximum effect) are calculated using curve-fitting software. The results in the form of EC$_{50}$ values are presented in Table 3.

TABLE 3

Cytotoxicity of the compounds according to the invention (in M) on MV411 and MOLM13 cell lines.

| | cell line FLT3-ITD | |
|---|---|---|
| Compound | MV411 | MOLM13 |
| 3 | 2.80E−09 | 5.60E−09 |
| 5 | 7.20E−09 | 1.80E−09 |
| 7 | 4.00E−08 | 3.40E−08 |
| 10 | 6.50E−09 | 6.00E−09 |
| 14 | 9.20E−09 | 4.50E−09 |
| 19 | 1.20E−08 | 1.34E−08 |
| 23 | 2.00E−08 | 6.60E−09 |
| 29 | 7.60E−09 | 1.50E−08 |
| 30 | 1.20E−08 | 1.50E−08 |
| 40 | 2.10E−08 | 2.00E−08 |
| 42 | 3.00E−09 | 7.00E−09 |
| 44 | 1.00E−08 | 8.80E−09 |

The invention claimed is:
1. A compound of the following general formula (I):

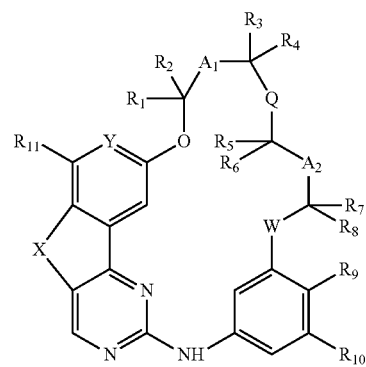

or a pharmaceutically acceptable salt and/or solvate thereof, wherein:
W represents an oxygen or sulfur atom,
X represents a saturated or unsaturated hydrocarbon chain comprising 1 to 3 carbon atoms, optionally substituted by one or more groups selected from a halogen atom, a (C$_1$-C$_6$)alkyl, oxo, OH and (C$_1$-C$_6$)alkoxy group, one or more carbon atoms of said chain being optionally each replaced, independently of each other, by an oxygen or sulfur atom,
Y represents a nitrogen atom or a CRy group wherein Ry represents a hydrogen atom, a halogen atom, a (C$_1$-C$_6$) alkyl, (C$_1$-C$_6$)haloalkyl, (C$_1$-C$_6$)alkoxy, (C$_1$-C$_6$)haloalkoxy, OH, CN, NO$_2$, NR$_{12}$R$_{13}$, CO$_2$H or CO$_2$((C$_1$-C$_6$)alkyl) group,
Q represents a single, double or triple bond, an oxygen or sulfur atom, or a (C$_1$-C$_6$)alkyl, S(O) or S(O)$_2$ group,
A$_1$ and A$_2$ represent, independently of each other, a single bond or a (C$_1$-C$_6$)alkyl group optionally substituted by an OH group, or A$_1$ and A$_2$ form with Q and the carbon atoms attached to Q an optionally substituted monocyclic carbocycle or heterocycle,
R$_1$, R$_2$, R$_3$, R$_4$, R$_5$, R$_6$, R$_7$, and R$_8$ represent, independently of each other, a hydrogen atom or a (C$_1$-C$_6$)alkyl group,
R$_9$ and R$_{10}$ represent, independently of each other, a hydrogen atom, a halogen atom, an optionally substituted $(C_1-C_6)$alkyl, optionally substituted $(C_2-C_6)$alkenyl, optionally substituted $(C_2-C_6)$alkynyl, optionally substituted $(C_1-C_6)$alkoxy, optionally substituted $(C_1-C_6)$thioalkoxy, CN, NO$_2$, NR$_{14}$R$_{15}$, OH, SH, CO$_2$R$_{54}$, CONR$_{55}$R$_{56}$ group, an optionally substituted carbocycle or an optionally substituted heterocycle, R$_{11}$ represents a hydrogen atom, a halogen atom, or a $(C_1-C_6)$alkyl, $(C_1-C_6)$haloalkyl, $(C_1-C_6)$alkoxy or $(C_1-C_6)$haloalkoxy group, and R$_{12}$, R$_{13}$, R$_{14}$, R$_{15}$, R$_{54}$, R$_{55}$ and R$_{56}$ represent, independently of each other, a hydrogen atom or an optionally substituted $(C_1-C_6)$alkyl, optionally substituted $(C_2-C_6)$alkenyl, or optionally substituted $(C_2-C_6)$alkynyl group, or R$_{12}$ and R$_{13}$, and/or R$_{14}$ and R$_{15}$ and/or R$_{55}$ and R$_{56}$, independently of each other, form with the nitrogen atom that bears them an optionally substituted heterocycle.

2. The compound according to claim 1, wherein X represents a CH$_2$—CH$_2$ or CH═CH chain.

3. The compound according to claim 1, wherein Y represents a CRy group wherein Ry represents a hydrogen atom or a halogen atom.

4. The compound according to claim 1, wherein W and Q each represent, independently of each other, O or S, and A$_1$ and A$_2$ each represent a single bond.

5. The compound according to claim 1, wherein W and Q each represent an oxygen atom, A$_1$ and A$_2$ each represent a single bond and R$_1$, R$_2$, R$_3$, R$_4$, R$_5$, R$_6$, R$_7$ and R$_8$ each represent a hydrogen atom.

6. The compound according to claim 1, wherein R$_{11}$ represents a hydrogen atom.

7. The compound according to claim 1, wherein R$_9$ and R$_{10}$ represent, independently of each other, a hydrogen atom, a halogen atom or a $(C_1-C_6)$alkyl, $(C_2-C_6)$alkenyl, $(C_2-C_6)$alkynyl, $(C_1-C_6)$alkoxy, $(C_1-C_6)$thioalkoxy, $(C_1-C_6)$alkylamino, di$((C_1-C_6)$alkyl)amino or heterocycle group, said group being optionally substituted by one or more substituents selected from:

a halogen atom, a $(C_1-C_6)$alkyl group optionally substituted by one or more groups selected from a halogen atom, OR$_{16}$, SR$_{17}$ and NR$_{18}$R$_{19}$, oxo (═O), CN, NO$_2$, OR$_{20}$, SR$_{21}$, NR$_{22}$R$_{23}$, C(O)R$_{24}$, CO$_2$R$_{25}$, OC(O)R$_{26}$, S(O)R$_{27}$, SO$_2$R$_{28}$, NR$_{29}$C(O)R$_{30}$, C(O)NR$_{31}$R$_{32}$, NR$_{33}$CO$_2$R$_{34}$, OC(O)NR$_{35}$R$_{36}$, NR$_{37}$CONR$_{38}$R$_{39}$ and OCO$_2$R$_{40}$ groups, a carbocycle optionally substituted by one or more groups selected from a halogen atom, a $(C_1-C_6)$alkyl group, oxo (═O), OR$_{41}$, SR$_{42}$ and NR$_{43}$R$_{44}$, a heterocycle optionally substituted by one or more groups selected from a halogen atom, a $(C_1-C_6)$alkyl group, oxo (═O), OR$_{45}$, SR$_{46}$ and NR$_{47}$R$_{48}$, and an —O(CH$_2$)$_n$O— group wherein n represents an integer between 1 and 5, wherein:

R$_{16}$ to R$_{48}$ represent, independently of each other, a hydrogen atom, a $(C_1-C_6)$alkyl, aryl, aryl-$(C_1-C_6)$alkyl, heterocycle or heterocycle-$(C_1-C_6)$alkyl group, the aryl ring of these groups being optionally substituted by one or more groups selected from a halogen atom and a $(C_1-C_6)$alkyl group, and the heterocyclic ring of these groups being optionally substituted by one or more groups selected from a halogen atom, a $(C_1-C_6)$alkyl group, and oxo(═O), or R$_{22}$ and R$_{23}$, R$_{31}$ and R$_{32}$, R$_{35}$ and R$_{36}$, R$_{38}$ and R$_{39}$, R$_{43}$ and R$_{44}$, and/or R$_{47}$ and R$_{48}$ form together, with the nitrogen atom that bears them, a nitrogen containing heterocycle optionally substituted by one or more groups selected from a halogen atom, a $(C_1-C_6)$alkyl group, and oxo(═O).

8. The compound according to claim 1, wherein R$_9$ and R$_{10}$ represent, independently of each other:

a hydrogen or halogen atom, a —Z—(CH$_2$)$_m$—R$_{49}$ group wherein Z represents a single bond, CH$_2$—CH$_2$, CH═CH, O, S or NR$_{50}$; m represents an integer between 1 and 6; R$_{50}$ represents a hydrogen atom or a $(C_1-C_6)$alkyl group; and R$_{49}$ represents a halogen atom, OR$_{20}$, NR$_{22}$R$_{23}$, C(O)R$_{24}$, CO$_2$R$_{25}$, OC(O)R$_{26}$, NR$_{29}$C(O)R$_{30}$, C(O)NR$_{31}$R$_{32}$, NR$_{33}$CO$_2$R$_{34}$, OC(O)NR$_{35}$R$_{36}$, NR$_{37}$CONR$_{38}$R$_{39}$ or OCO$_2$R$_{40}$, or a monocyclic or bicyclic heterocycle, each ring having 5, 6 or 7 members, comprising 1 or 2 heteroatoms selected from N and O, optionally substituted by one or more substituents selected from:

a halogen atom, a $(C_1-C_6)$alkyl group optionally substituted by one or more groups selected from a halogen atom, OR$_{16}$, NR$_{18}$R$_{19}$, a C$_3$ to C$_6$ monocyclic carbocycle and a 3- to 6-membered monocyclic heterocycle oxo (═O), OR$_{20}$, NR$_{22}$R$_{23}$, C(O)R$_{24}$, CO$_2$R$_{25}$, OC(O)R$_{26}$, NR$_{29}$C(O)R$_{30}$, C(O)NR$_{31}$R$_{32}$, NR$_{33}$CO$_2$R$_{34}$, OC(O)NR$_{35}$R$_{36}$, NR$_{37}$CONR$_{38}$R$_{39}$ or OCO$_2$R$_{40}$ groups, a C$_3$ to C$_6$ carbocycle optionally substituted by one or more groups selected from a halogen atom, a $(C_1-C_6)$alkyl group, oxo (═O), OR$_{41}$ and NR$_{43}$R$_{44}$, a 3- to 6-membered heterocycle comprising 1 or 2 heteroatoms selected from N and O, optionally substituted by one or more groups selected from a halogen atom, a $(C_1-C_6)$alkyl group, oxo (═O), OR$_{45}$ and NR$_{47}$R$_{48}$, and an —O(CH$_2$)$_n$O— group wherein n represents an integer equal to 2 or 3, wherein:

R$_{16}$, R$_{18}$ to R$_{20}$, R$_{22}$ to R$_{26}$, R$_{29}$ to R$_{41}$, R$_{43}$ to R$_{45}$ and R$_{47}$ to R$_{48}$ represent, independently of each other, a hydrogen atom, a $(C_1-C_6)$alkyl, aryl, aryl-$(C_1-C_6)$alkyl, heterocycle or heterocycle-$(C_1-C_6)$alkyl group, the aryl ring of these groups being a phenyl group and being optionally substituted by one or more groups selected from a halogen atom and a $(C_1-C_6)$alkyl group, and the heterocyclic ring of these groups being a 3- to 6-membered heterocycle comprising 1 or 2 heteroatoms selected from N and O, and being optionally substituted by one or more groups selected from a halogen atom, a $(C_1-C_6)$alkyl group and oxo(═O), or R$_{22}$ and R$_{23}$, R$_{31}$ and R$_{32}$, R$_{35}$ and R$_{36}$, R$_{38}$ and R$_{39}$, R$_{43}$ and R$_{44}$, and/or R$_{47}$ and R$_{48}$ form together, with the nitrogen atom that bears them, a 5- or 6-membered nitrogen containing heterocycle, optionally comprising 1 heteroatom in addition to the nitrogen atom selected from N and O, the heterocycle being optionally substituted by one or more groups selected from a halogen atom, a $(C_1-C_6)$alkyl group, and oxo(═O).

9. The compound according to claim 1, wherein R$_{10}$ represents a hydrogen atom.

10. The compound according to claim 1, wherein it is a compound of the following formula (Ib):

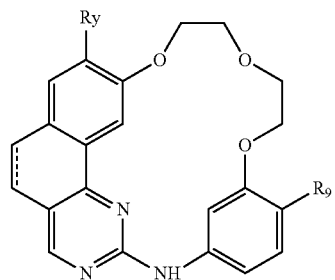

(Ib)

or a pharmaceutically acceptable salt and/or solvate thereof, wherein:

- - - represents a single bond or a double bond,

Ry represents a hydrogen atom, a halogen atom, a ($C_1$-$C_6$)alkyl or ($C_1$-$C_6$)haloalkyl group, and $R_9$ represents a saturated monocyclic or bicyclic nitrogen containing heterocycle, each ring of which comprises 5 or 6 members, optionally comprising 1 heteroatom selected from N and O in addition to the nitrogen atom, the nitrogen containing heterocycle being attached to the rest of the molecule by its nitrogen atom and being optionally substituted by one or more sub stituents selected from:

a halogen atom, a ($C_1$-$C_6$)alkyl group optionally substituted by one or more groups selected from a halogen atom, $OR_{16}$ and $NR_{18}R_{19}$, oxo (=O), $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ and $OCO_2R_{40}$ groups, a $C_3$ to $C_6$ carbocycle optionally substituted by one or more groups selected from a halogen atom, a ($C_1$-$C_6$)alkyl group, oxo (=O), $OR_{41}$ and $NR_{43}R_{44}$, a 3- to 6-membered heterocycle comprising 1 or 2 heteroatoms selected from N and O, optionally substituted by one or more groups selected from a halogen atom, a ($C_1$-$C_6$)alkyl group, oxo (=O), $OR_{45}$ and $NR_{47}R_{48}$, and an —$(CH_2)_nO$— group wherein n represents an integer equal to 2 or 3 (the two oxygens of this group being attached to the same atom or to two different atoms, wherein:

$R_{16}$, $R_{18}$ to $R_{20}$, $R_{22}$, $R_{23}$, $R_{25}$, $R_{31}$ to $R_{41}$, $R_{43}$ to $R_{45}$, $R_{47}$ and $R_{48}$ represent, independently of each other, a hydrogen atom, a ($C_1$-$C_6$)alkyl, aryl, or aryl-($C_1$-$C_6$)alkyl group, the aryl ring of these groups being optionally substituted by one or more groups selected from a halogen atom and a ($C_1$-$C_6$)alkyl group, or $R_{22}$ and $R_{23}$, Rn and $R_{32}$, $R_{35}$ and $R_{36}$, $R_{38}$ and $R_{39}$, and/or $R_{47}$ and $R_{48}$ form together, with the nitrogen atom that bears them, a 5- or 6-membered nitrogen containing heterocycle optionally comprising 1 heteroatom in addition to the nitrogen atom selected from N and O, the heterocycle being optionally substituted by one or more groups selected from a halogen atom, a ($C_1$-$C_6$)alkyl group, and oxo(=O).

11. The compound according to claim 1, wherein it is selected from the following compounds:

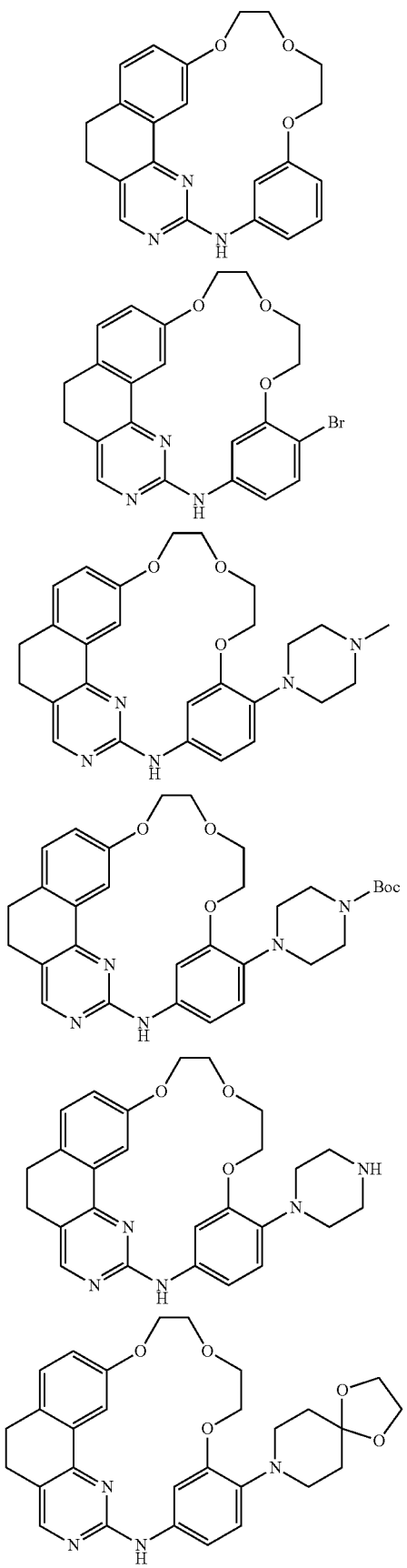

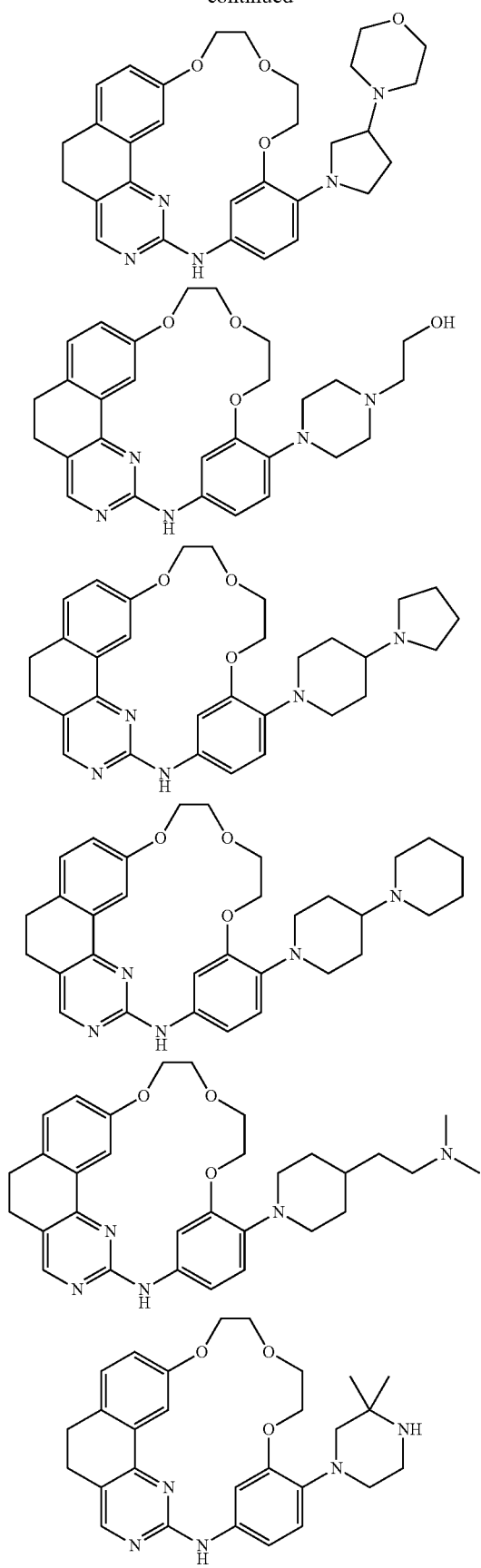
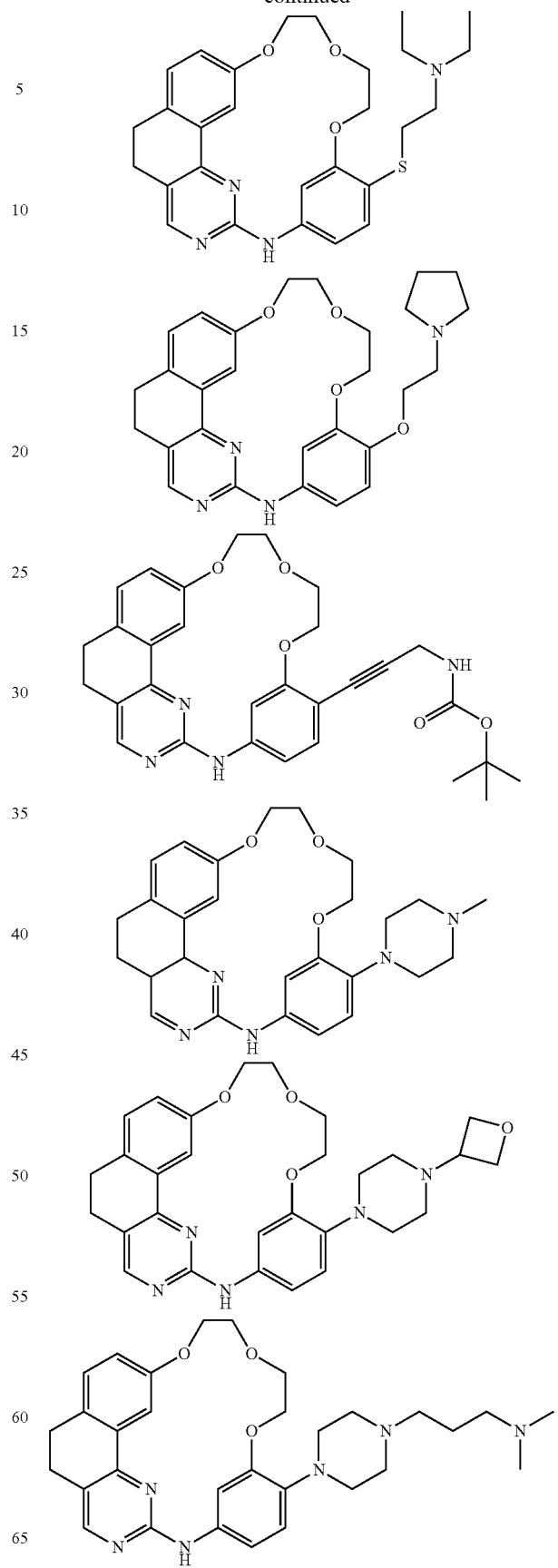

-continued
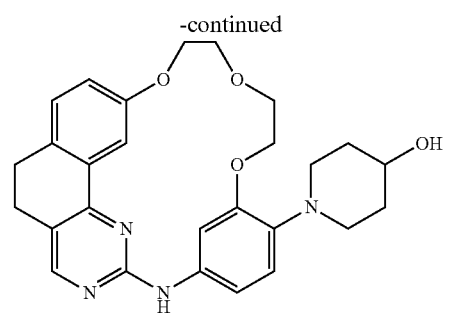
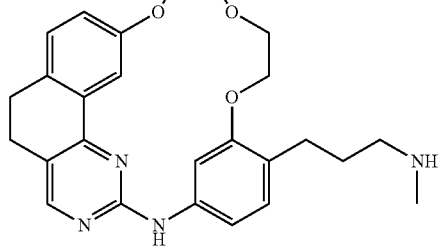
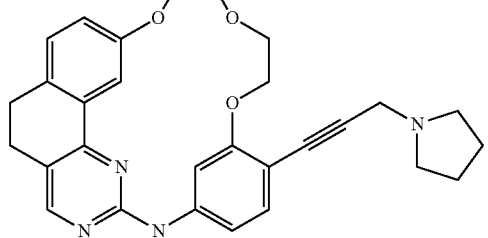
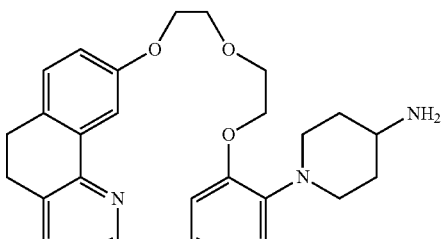
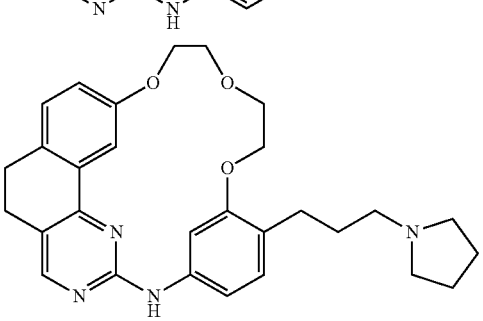
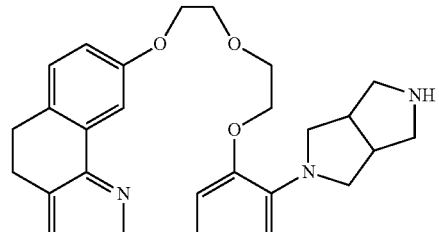
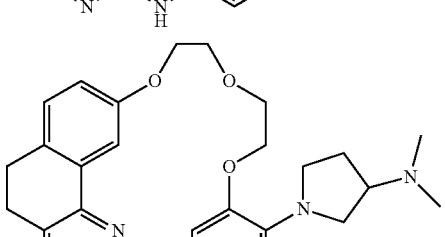

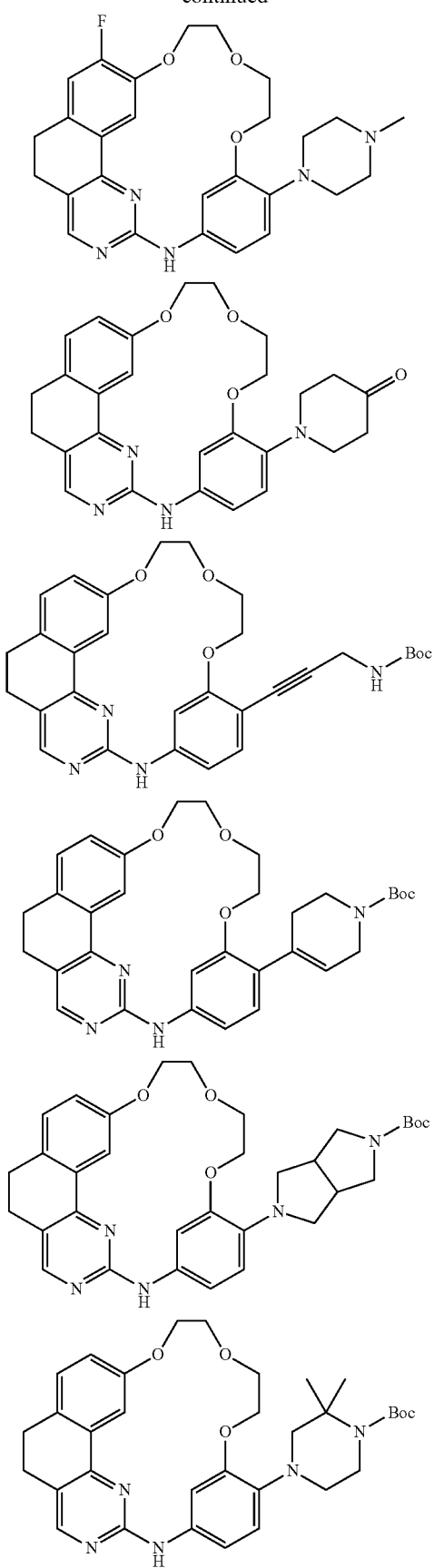
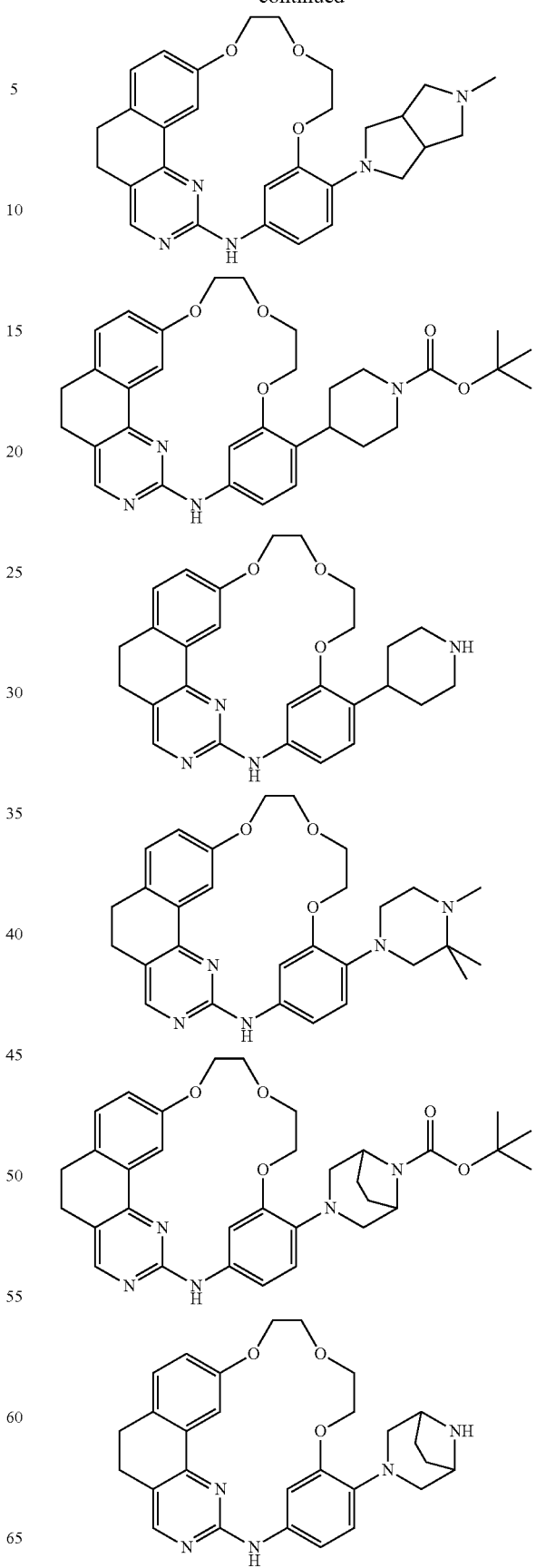

-continued

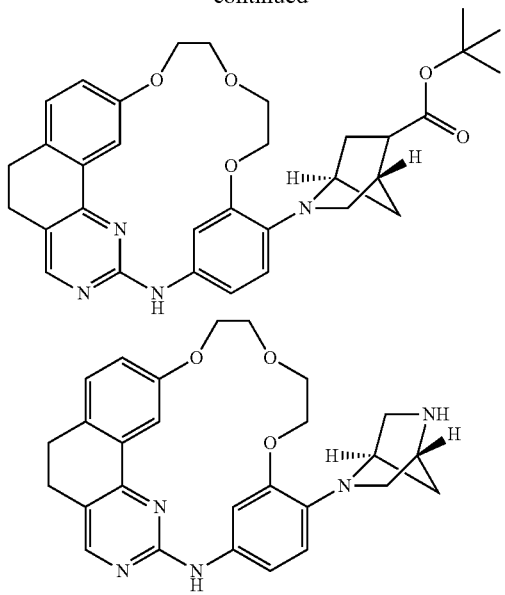

or a pharmaceutically acceptable salt and/or solvate thereof.

12. A pharmaceutical composition comprising at least one compound according to claim 1 and at least one pharmaceutically acceptable excipient.

13. A method for preparing a compound according to claim 1 comprising the coupling reaction between:
a compound of the following formula (II):

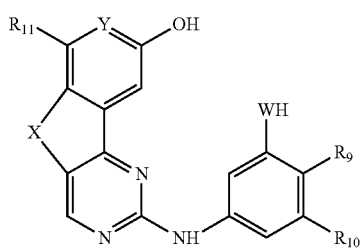

and
a compound of the following formula (III):

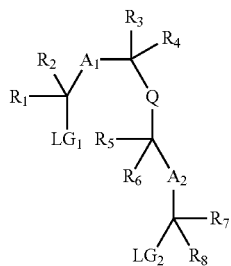

wherein $LG_1$ and $LG_2$ each represent, independently of each other, a leaving group.

14. A method for preparing a compound according to claim 1, wherein $R_9$ or $R_{10}$ represents an optionally substituted $(C_1\text{-}C_6)$alkoxy, optionally substituted $(C_1\text{-}C_6)$thioalkoxy or $NR_{14}R_{15}$ group or an optionally substituted heterocycle comprising a heteroatom directly attached to the phenyl ring, comprising the coupling between a compound of the following formula (IVa) or (IVb):

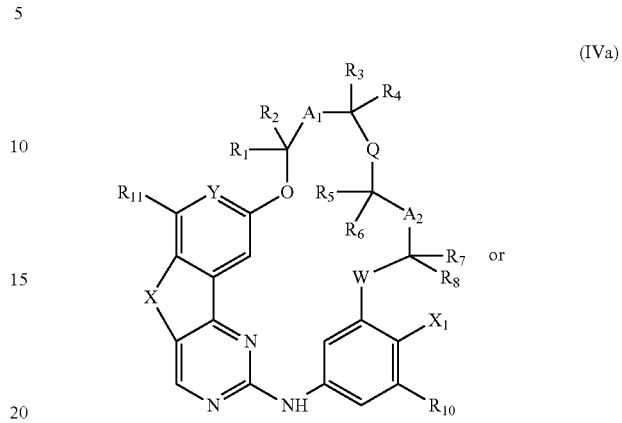

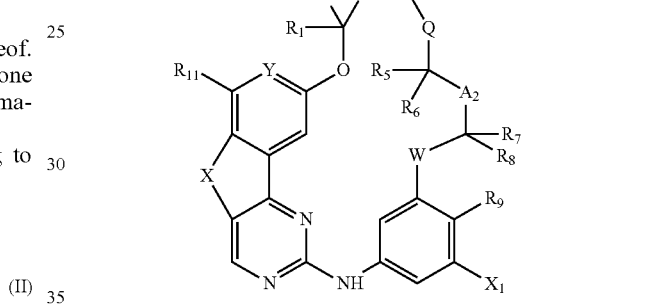

wherein $X_1$ represents a halogen atom,
and respectively a compound of formula $R_9H$ or $R_{10}H$ wherein $R_9$ and $R_{10}$ are as defined above.

15. A method for preparing a compound according to claim 1, wherein $R_9$ and/or $R_{10}$ represents an optionally substituted $(C_1\text{-}C_6)$alkyl, optionally substituted $(C_2\text{-}C_6)$alkenyl or optionally substituted $(C_2\text{-}C_6)$alkynyl group, an optionally substituted carbocycle or an optionally substituted heterocycle attached to the phenyl ring by means of a carbon atom, comprising the coupling between a compound of the following formula (Va) or (Vb):

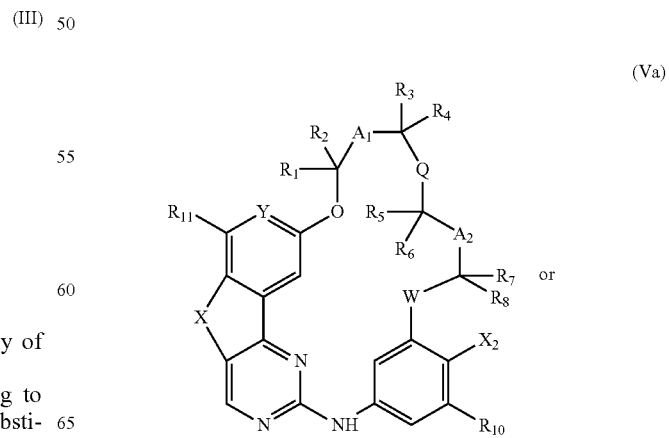

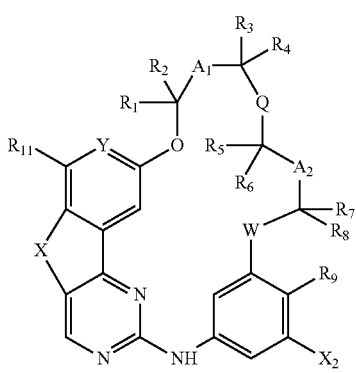

(Vb)

wherein $X_2$ represents Br, Cl, I or OTf, and respectively a compound of formula $R_9$—$BR_{52}R_{53}$ or $R_{10}$—$BR_{52}R_{53}$ wherein $R_9$ and $R_{10}$ are as defined above and $R_{52}$ and $R_{53}$ represent, independently of each other, an OH, $(C_1$-$C_6)$alkyl or $(C_1$-$C_6)$alkoxy group or $R_{52}$ and $R_{53}$ together form an —$X_3$— or —O—$X_3$—O— chain wherein $X_3$ represents a divalent hydrocarbon group comprising 2 to 15 carbon atoms.

16. A method for preparing a compound according to claim 8, wherein $R_9$ and/or $R_{10}$ represents a —Z—$(CH_2)_m$—$R_{49}$ group wherein Z represents $CH_2$—$CH_2$, CH=CH or C≡C, comprising the following steps:
(1) Sonogashira coupling between a compound of the following formula (Va) or (Vb):

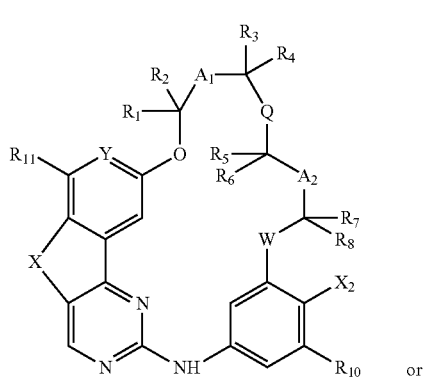

wherein $X_2$ represents Br, Cl, I or OTf,
and a compound of formula HC≡C—$(CH_2)_m$—$R_{49}$ wherein m and $R_{49}$ are as defined in claim 8, to give a compound of formula (I) wherein $R_9$ or $R_{10}$ represents —C≡C—$(CH_2)_m$—$R_{49}$, and
(2) optionally reduction of the alkyne function of the compound of formula (I) obtained in the preceding step to give a compound of formula (I) wherein $R_9$ or $R_{10}$ represents —CH=CH—$(CH_2)_m$—$R_{49}$ or —$(CH_2)_{m+2}$—$R_{49}$.

17. The compound according to claim 8, wherein $R_9$ and $R_{10}$ represent, independently of each other:
a hydrogen or halogen atom,
a —Z—$(CH_2)_m$—$R_{49}$ group wherein Z represents a single bond, $CH_2$—$CH_2$, CH=CH, C≡C, O, S or $NR_{50}$; m represents an integer between 1 and 4; $R_{50}$ represents a hydrogen atom or a $(C_1$-$C_6)$alkyl group; and $R_{49}$ represents $OR_{20}$), $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ or $OCO_2R_{40}$, or
a monocyclic or bicyclic heterocycle, each ring having 5 or 6 members, comprising 1 or 2 heteroatoms selected from N and O, saturated or containing a double bond, optionally substituted by one or more substituents selected from:
a halogen atom,
a $(C_1$-$C_6)$alkyl group optionally substituted by one or more groups selected from a halogen atom, $OR_{16}$, $NR_{18}R_{19}$, a $C_3$ to $C_6$ saturated monocyclic carbocycle and a 3- to 6-membered saturated monocyclic heterocycle,
oxo (=O), $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ or $OCO_2R_{40}$ groups,
a $C_3$ to $C_6$ carbocycle optionally substituted by one or more groups selected from a halogen atom, a $(C_1$-$C_6)$alkyl group, oxo (=O), $OR_{41}$ and $NR_{43}R_{44}$,
a saturated or unsaturated 3- to 6-membered heterocycle, comprising 1 or 2 heteroatoms selected from N and O, optionally substituted by one or more groups selected from a halogen atom, a $(C_1$-$C_6)$alkyl group, oxo (=O), $OR_{45}$ and $NR_{47}R_{48}$, and
an —$(CH_2)_n$O— group wherein n represents an integer equal to 2 or 3,
wherein:
$R_{16}$, $R_{18}$ to $R_{20}$, $R_{22}$ to $R_{23}$, $R_{25}$, $R_{31}$ to $R_{41}$, $R_{43}$ to $R_{45}$ and $R_{47}$ to $R_{48}$ represent, independently of each other, a hydrogen atom, a $(C_1$-$C_6)$alkyl, aryl, aryl-$(C_1$-$C_6)$alkyl, heterocycle or heterocycle-$(C_1$-$C_6)$alkyl group,
the aryl ring of these groups being a phenyl group and being optionally substituted by one or more groups selected from a halogen atom and a $(C_1$-$C_6)$alkyl group, and
the heterocyclic ring of these groups being a 5- or 6-membered heterocycle comprising 1 or 2 heteroatoms selected from N and O, and being optionally substituted by one or more groups selected from a halogen atom, a $(C_1$-$C_6)$alkyl group and oxo(=O), or
$R_{22}$ and $R_{23}$, $R_{31}$ and $R_{32}$, $R_{35}$ and $R_{36}$, $R_{38}$ and $R_{39}$, $R_{43}$ and $R_{44}$, and/or $R_{47}$ and $R_{48}$ form together, with the nitrogen atom that bears them, a saturated 5- or 6-membered nitrogen containing heterocycle, optionally comprising 1 heteroatom in addition to the nitrogen atom selected from N and O, the heterocycle being optionally substituted by one or more groups selected from a halogen atom, a $(C_1$-$C_6)$alkyl group, and oxo(=O).

18. The compound according to claim 17, wherein $R_9$ and $R_{10}$ represent, independently of each other:
- a hydrogen or halogen atom,
- a —Z—$(CH_2)_m$—$R_{49}$ group wherein $R_{49}$ represents $NR_{22}R_{23}$, $NR_{33}CO_2R_{34}$, or $NR_{37}CONR_{38}R_{39}$, or
- a monocyclic or bicyclic heterocycle, each ring having 5 or 6 members, comprising 1 or 2 heteroatoms selected from N and O, saturated or containing a double bond, optionally substituted by one or more substituents selected from:
  - a halogen atom,
  - a $(C_1$-$C_6)$alkyl group optionally substituted by one or more groups selected from a halogen atom, $OR_{16}$ and $NR_{18}R_{19}$,
  - oxo (=O), $OR_{20}$, $NR_{22}R_{23}$, $CO_2R_{25}$, $C(O)NR_{31}R_{32}$, $NR_{33}CO_2R_{34}$, $OC(O)NR_{35}R_{36}$, $NR_{37}CONR_{38}R_{39}$ or $OCO_2R_{40}$ groups,
  - a $C_3$ to $C_6$ carbocycle optionally substituted by one or more groups selected from a halogen atom, a $(C_1$-$C_6)$alkyl group, oxo (=O), $OR_{41}$ and $NR_{43}R_{44}$,
  - a saturated 3- to 6-membered heterocycle comprising 1 or 2 heteroatoms selected from N and O, optionally substituted by one or more groups selected from a halogen atom, a $(C_1$-$C_6)$alkyl group, oxo (=O), $OR_{45}$ and $NR_{47}R_{48}$, and
  - an —$O(CH_2)_n$O— group wherein n represents an integer equal to 2 or 3, wherein:
- $R_{16}$, $R_{18}$ to $R_{20}$, $R_{22}$ to $R_{23}$, $R_{25}$, $R_{29}$ to $R_{40}$, $R_{41}$, $R_{43}$ to $R_{45}$ and $R_{47}$ to $R_{48}$ represent, independently of each other, a hydrogen atom, a $(C_1$-$C_6)$alkyl, aryl, aryl-$(C_1$-$C_6)$alkyl, heterocycle or heterocycle-$(C_1$-$C_6)$ alkyl group,
  - the aryl ring of these groups being a phenyl group and being optionally substituted by one or more groups selected from a halogen atom and a $(C_1$-$C_6)$alkyl group, and
  - the heterocyclic ring of these groups being a 5- or 6-membered, heterocycle comprising 1 or 2 heteroatoms selected from N and O, and being optionally substituted by one or more groups selected from a halogen atom, a $(C_1$-$C_6)$alkyl group and oxo(=O), or
- $R_{22}$ and $R_{23}$, $R_{31}$ and $R_{32}$, $R_{35}$ and $R_{36}$, $R_{38}$ and $R_{39}$, $R_{43}$ and $R_{44}$, and/or $R_{47}$ and $R_{48}$ form together, with the nitrogen atom that bears them, a heterocycle selected from piperazine, piperidine, morpholine and pyrrolidine, optionally substituted by one or more groups selected from a halogen atom, a $(C_1$-$C_6)$alkyl group, and oxo(=O).

19. The compound according to claim 10, wherein:
- ≡≡≡ represents a single bond,
- Ry represents a hydrogen atom or a halogen atom, and
- $R_9$ represents a heterocycle selected from piperazine, 2,5-diazabicyclo[4.2.0]octane, 3,8-diazabicyclo[3.2.1]octane, 2,5-diazabicyclo[2.2.1]heptane, piperidine, morpholine, perhydropyrrolo[3,4-c]pyrrole and pyrrolidine, attached to the rest of the molecule by its nitrogen atom and optionally substituted by one or more substituents selected from:
  - a halogen atom,
  - a $(C_1$-$C_6)$alkyl group optionally substituted by one or more groups selected from a halogen atom, $OR_{16}$ and $NR_{18}R_{19}$,
  - oxo (=O), $OR_{20}$, $NR_{22}R_{23}$, $CO_2R_{25}$, $C(O)NR_{31}R_{32}$, $NR_{33}CO_2R_{34}$, $OC(O)NR_{38}R_{36}$, $NR_{37}CONR_{38}R_{39}$ and $OCO_2R_{40}$ groups,
  - a $C_3$ to $C_6$ carbocycle optionally substituted by one or more groups selected from a halogen atom, a $(C_1$-$C_6)$alkyl group, oxo (=O), $OR_{41}$ and $NR_{43}R_{44}$,
  - a saturated 3- to 6-membered heterocycle comprising 1 or 2 heteroatoms selected from N and O, optionally substituted by one or more groups selected from a halogen atom, a $(C_1$-$C_6)$alkyl group, oxo (=O), $OR_{45}$ and $NR_{47}R_{48}$, and
  - an —$O(CH_2)_n$O— group wherein n represents an integer equal to 2 or 3, the two oxygens of this group being attached to the same carbon atom to form a cyclic acetal, wherein:
- $R_{16}$ to $R_{18}$, $R_{20}$, $R_{22}$, $R_{23}$, $R_{25}$, $R_{31}$ to $R_{41}$, $R_{43}$ to $R_{45}$, $R_{47}$ and $R_{48}$ represent, independently of each other, a hydrogen atom or a $(C_1$-$C_6)$alkyl group,
  - the aryl ring of these groups being a phenyl group and being optionally substituted by one or more groups selected from a halogen atom and a $(C_1$-$C_6)$alkyl group, or
- $R_{22}$ and $R_{23}$, $R_{31}$ and $R_{32}$, $R_{35}$ and $R_{36}$, $R_{38}$ and $R_{39}$, $R_{43}$ and $R_{44}$, and/or $R_{47}$ and $R_{48}$ form together, with the nitrogen atom that bears them, a heterocycle selected from piperazine, piperidine, morpholine and pyrrolidine, optionally substituted by one or more groups selected from a halogen atom, a $(C_1$-$C_6)$alkyl group, and oxo(=O).

20. A method for the treatment of leukemia comprising the administration to a person in need thereof of an effective dose of a compound according to claim 1.

* * * * *